(12) United States Patent
Hopper

(10) Patent No.: US 11,709,175 B2
(45) Date of Patent: Jul. 25, 2023

(54) DIAGNOSTIC TEST SYSTEM AND METHOD UTILIZING A CLOSURE/SAMPLE DISPENSING MECHANISM TO DISPENSE A SAMPLE SUBVOLUME FOR TESTING

(71) Applicant: AXXIN PTY LTD, Fairfield (AU)

(72) Inventor: William R. Hopper, East Ivanhoe (AU)

(73) Assignee: AXXIN PTY LTD, Fairfield (AU)

( * ) Notice: Subject to any disclaimer, the term of this patent is extended or adjusted under 35 U.S.C. 154(b) by 541 days.

(21) Appl. No.: 16/650,125

(22) PCT Filed: Sep. 21, 2018

(86) PCT No.: PCT/AU2018/051044
§ 371 (c)(1),
(2) Date: Mar. 24, 2020

(87) PCT Pub. No.: WO2019/060950
PCT Pub. Date: Apr. 4, 2019

(65) Prior Publication Data
US 2020/0278368 A1    Sep. 3, 2020

(30) Foreign Application Priority Data
Sep. 27, 2017   (AU) ................................ 2017903919

(51) Int. Cl.
*G01N 35/10*    (2006.01)
*C12N 1/06*    (2006.01)
(Continued)

(52) U.S. Cl.
CPC ............ *G01N 35/1009* (2013.01); *C12N 1/06* (2013.01); *C12Q 1/686* (2013.01); *G01N 1/28* (2013.01);
(Continued)

(58) Field of Classification Search
CPC .... G01N 35/1009; G01N 1/28; G01N 21/763; G01N 35/1079; G01N 35/0098;
(Continued)

(56) References Cited

U.S. PATENT DOCUMENTS 3,715,189 A  *  2/1973  Nighohossian ......... B01L 3/502
422/430
3,913,562 A  *  10/1975  Moore ............... A61B 10/0096
435/307.1
(Continued)

FOREIGN PATENT DOCUMENTS

AU    2013202899 A1    5/2013
EP    1059523 B1    7/2007
(Continued)

OTHER PUBLICATIONS

Cikos et al.; Transformation of real-time PCR fluorescence data to target gene quantity; Analytical Biochemistry; 384(1); pp. 1-10; Jan. 1, 2009.
(Continued)

*Primary Examiner* — Arlen Soderquist
(74) *Attorney, Agent, or Firm* — Shay Glenn LLP

(57) ABSTRACT

A diagnostic test system, including: a diagnostic test assembly and a diagnostic test apparatus to perform a test on a biological or environmental sample; the diagnostic test assembly includes: a sample preparation reservoir to receive the sample into a sample preparation fluid, such that a swab carrying the sample can be used to stir the preparation fluid and to wash the swab; a sample dispensing mechanism for insertion into the sample preparation reservoir; a closure to seal the sample preparation reservoir; at least one diagnostic test reservoir coupled to the sample preparation reservoir; and at least one seal between the sample preparation reservoir and the diagnostic test reservoir to prevent fluid movement between the respective reservoirs; wherein the sample
(Continued)

dispensing mechanism is operable to disrupt the seal to allow sample fluid to enter the diagnostic test reservoir from the sample preparation reservoir, and to dispense a predetermined amount of fluid.

28 Claims, 38 Drawing Sheets

(51) Int. Cl.
    *C12Q 1/68*     (2018.01)
    *G01N 1/28*     (2006.01)
    *G01N 35/00*     (2006.01)
    *C12Q 1/686*     (2018.01)
    *G01N 21/76*     (2006.01)

(52) U.S. Cl.
    CPC ....... *G01N 21/763* (2013.01); *G01N 35/0098* (2013.01); *G01N 2035/00277* (2013.01); *G01N 2035/00346* (2013.01); *Y02A 90/10* (2018.01)

(58) Field of Classification Search
    CPC ... G01N 35/0099; B01L 3/5029; B01L 3/502; C12Q 1/686; C12N 1/06; Y02A 90/10
    USPC .......................................... 436/63; 435/283.1
    See application file for complete search history.

(56) References Cited

U.S. PATENT DOCUMENTS

| | | | | |
|---|---|---|---|---|
| 4,150,950 | A * | 4/1979 | Takeguchi | B01L 3/5082 600/572 |
| 4,196,167 | A * | 4/1980 | Olsen | B01L 3/505 600/572 |
| 4,234,540 | A | 11/1980 | Ginsberg et al. | |
| 4,250,266 | A | 2/1981 | Wade | |
| 4,353,868 | A * | 10/1982 | Joslin | C12M 33/02 435/304.2 |
| 4,376,634 | A * | 3/1983 | Prior | G01N 33/579 600/572 |
| 4,580,577 | A | 4/1986 | O'Brien | A61B 10/0051 422/430 |
| 4,770,853 | A * | 9/1988 | Bernstein | G01N 33/5302 435/287.7 |
| 4,903,708 | A * | 2/1990 | Saint-Amand | A61F 15/001 600/572 |
| 4,912,034 | A | 3/1990 | Kalra et al. | |
| 5,152,965 | A | 10/1992 | Fisk et al. | |
| 5,169,789 | A * | 12/1992 | Bernstein | G01N 33/5302 436/524 |
| 5,266,266 | A * | 11/1993 | Nason | A61B 10/0096 604/3 |
| 5,435,970 | A | 7/1995 | Mamenta et al. | |
| 5,658,531 | A * | 8/1997 | Cope | G01N 21/0303 422/430 |
| 5,827,675 | A * | 10/1998 | Skiffington | C12Q 1/00 435/287.7 |
| 5,917,592 | A * | 6/1999 | Skiffington | G01N 21/76 356/244 |
| 5,955,351 | A | 9/1999 | Gerdes et al. | |
| 5,965,453 | A * | 10/1999 | Skiffington | C12Q 1/66 435/287.7 |
| 6,153,425 | A * | 11/2000 | Kozwich | B01L 3/5082 435/306.1 |
| 6,171,870 | B1 | 1/2001 | Freitag | |
| 6,197,598 | B1 | 3/2001 | Schrier et al. | |
| 6,524,530 | B1 * | 2/2003 | Igarashi | G01N 1/02 435/304.2 |
| 6,599,712 | B1 * | 7/2003 | Sakakibara | C12Q 1/008 435/8 |
| 6,641,782 | B1 * | 11/2003 | Mauchan | G01N 21/76 422/52 |
| 7,238,520 | B2 | 7/2007 | Brown et al. | |
| 8,476,064 | B2 * | 7/2013 | Salter | G01N 33/9446 435/307.1 |
| 8,895,296 | B2 | 11/2014 | Sano et al. | |
| 9,145,581 | B1 * | 9/2015 | Lai | B01L 3/523 |
| 9,757,095 | B2 | 9/2017 | Terbrueggen et al. | |
| 9,932,629 | B2 | 4/2018 | Hopper | |
| 10,428,375 | B2 | 10/2019 | Hopper | |
| 10,463,290 | B2 | 11/2019 | Hopper et al. | |
| 2001/0039415 | A1 | 11/2001 | Francischelli et al. | |
| 2002/0001539 | A1 * | 1/2002 | DiCesare | B01L 3/5029 422/174 |
| 2002/0031768 | A1 | 3/2002 | McMillan et al. | |
| 2002/0085958 | A1 * | 7/2002 | Nemcek | B01L 3/502715 422/400 |
| 2003/0129738 | A1 | 7/2003 | Sorenson | |
| 2003/0170686 | A1 | 9/2003 | Hoet et al. | |
| 2004/0161788 | A1 | 8/2004 | Chen et al. | |
| 2004/0265173 | A1 | 12/2004 | Matsumoto et al. | |
| 2005/0033196 | A1 | 2/2005 | Alroy | |
| 2005/0142031 | A1 | 6/2005 | Wickstead et al. | |
| 2005/0180891 | A1 | 8/2005 | Webster et al. | |
| 2006/0030790 | A1 | 2/2006 | Braig et al. | |
| 2006/0135953 | A1 | 6/2006 | Kania et al. | |
| 2006/0166367 | A1 * | 7/2006 | Satoh | G01N 33/52 436/86 |
| 2006/0188392 | A1 | 8/2006 | Tanaka et al. | |
| 2006/0223172 | A1 | 10/2006 | Bedingham et al. | |
| 2006/0270027 | A1 | 11/2006 | Shaw et al. | |
| 2006/0275852 | A1 | 12/2006 | Montagu et al. | |
| 2006/0275922 | A1 | 12/2006 | Gould et al. | |
| 2006/0292035 | A1 | 12/2006 | Gould et al. | |
| 2007/0184492 | A1 | 8/2007 | Wang et al. | |
| 2008/0020380 | A1 | 1/2008 | Patno et al. | |
| 2008/0166820 | A1 | 7/2008 | Gould et al. | |
| 2008/0199851 | A1 * | 8/2008 | Egan | B01L 3/5029 435/5 |
| 2008/0260581 | A1 * | 10/2008 | Rosman | B01L 3/5029 422/68.1 |
| 2008/0287308 | A1 | 11/2008 | Hubbell et al. | |
| 2009/0024016 | A1 | 1/2009 | Zhang et al. | |
| 2009/0181388 | A1 | 7/2009 | You et al. | |
| 2009/0204997 | A1 | 8/2009 | Xu et al. | |
| 2009/0298051 | A1 * | 12/2009 | Salter | C12Q 1/10 435/5 |
| 2010/0070190 | A1 | 3/2010 | Lerner | |
| 2010/0077843 | A1 * | 4/2010 | Doraisamy | B01L 3/5029 73/864.01 |
| 2010/0192706 | A1 * | 8/2010 | Fairs | B01L 3/502 73/863.23 |
| 2010/0285578 | A1 * | 11/2010 | Selden | B01L 3/502715 536/25.4 |
| 2011/0039261 | A1 | 2/2011 | Hillebrand et al. | |
| 2011/0236879 | A1 * | 9/2011 | Egan | G01N 33/56983 435/5 |
| 2011/0256531 | A1 * | 10/2011 | Rajagopal | C12Q 1/04 435/7.1 |
| 2011/0283818 | A1 | 11/2011 | Kramer | |
| 2012/0076693 | A1 | 3/2012 | Hopper | |
| 2012/0094281 | A1 * | 4/2012 | Rajagopal | C12Q 1/04 435/7.1 |
| 2013/0029324 | A1 * | 1/2013 | Rajagopal | B01L 3/502 435/8 |
| 2013/0309679 | A1 | 11/2013 | Ismagilov et al. | |
| 2014/0004548 | A1 | 1/2014 | Gordon et al. | |
| 2014/0072960 | A1 * | 3/2014 | Lansing | G01N 33/5302 435/7.1 |
| 2014/0194305 | A1 | 7/2014 | Kayyem et al. | |
| 2015/0024436 | A1 | 1/2015 | Eberhart et al. | |
| 2015/0157381 | A1 | 6/2015 | Ashton et al. | |
| 2015/0190805 | A1 | 7/2015 | Etheredge et al. | |
| 2016/0029897 | A1 | 2/2016 | Fojtik | |
| 2016/0051235 | A1 | 2/2016 | Wan et al. | |
| 2016/0258849 | A1 | 9/2016 | Murayama et al. | |
| 2017/0014182 | A1 | 1/2017 | Razavi et al. | |
| 2017/0176302 | A1 | 6/2017 | Bearinger et al. | |
| 2018/0193831 | A1 | 7/2018 | Hopper | |

(56) References Cited

U.S. PATENT DOCUMENTS

| | | | |
|---|---|---|---|
| 2019/0030527 A1* | 1/2019 | Walsh | C12Q 1/24 |
| 2019/0083975 A1* | 3/2019 | Mitra | C12Q 1/6844 |
| 2019/0376129 A1 | 12/2019 | Hopper | |

FOREIGN PATENT DOCUMENTS

| | | | | |
|---|---|---|---|---|
| EP | 2123360 | A1 | | 11/2009 |
| EP | 2163999 | A2 | | 3/2010 |
| FR | 2590673 | A1 | | 5/1987 |
| JP | H08-43294 | A | | 2/1996 |
| JP | 2005300164 | A | | 10/2005 |
| JP | 2016518588 | A | | 6/2016 |
| JP | 2016158557 | A | | 9/2016 |
| JP | 2016214174 | A | | 12/2016 |
| WO | WO92/08986 | A1 | | 5/1992 |
| WO | 97/23596 | | * | 7/1997 |
| WO | 98/27196 | | * | 6/1998 |
| WO | 99/31218 | | * | 6/1999 |
| WO | WO99/57561 | A2 | | 11/1999 |
| WO | 00/60348 | | * | 10/2000 |
| WO | WO-0065022 | A1 | * 11/2000 | B01L 3/5029 |
| WO | WO2004/011148 | A2 | | 2/2004 |
| WO | WO2005/045408 | A1 | | 5/2005 |
| WO | WO2005/118772 | A1 | | 12/2005 |
| WO | WO2006/047777 | A2 | | 5/2006 |
| WO | WO2007/005077 | A1 | | 1/2007 |
| WO | WO2007/106579 | A2 | | 9/2007 |
| WO | WO2008/005248 | A2 | | 1/2008 |
| WO | WO 2009/011869 | A1 | | 1/2009 |
| WO | WO 2009/132268 | A1 | | 10/2009 |
| WO | WO2010/030686 | A1 | | 3/2010 |
| WO | WO2010/104478 | A1 | | 9/2010 |
| WO | WO2013/113054 | A1 | | 8/2013 |
| WO | WO2014/000037 | A1 | | 1/2014 |
| WO | WO2014/100732 | A1 | | 6/2014 |
| WO | WO2015/084458 | A2 | | 6/2015 |
| WO | WO2017/011862 | A1 | | 1/2017 |
| WO | WO2017/062892 | A1 | | 4/2017 |
| WO | WO2021/053460 | A2 | | 3/2021 |

OTHER PUBLICATIONS

Durtschi et al.; Evaluation of quantification methods for real-time PCR minor groove binding hybridization probe assays; Analytical Biochemistry; 361(1); pp. 55-64; Jan. 4, 2007.

European Leukemia Network; Imatinib testing for CML; 7 pages; retrieved from the internet (https://www.eutos.org/content/molecular_monitoring/information/pcr_testing/index_eng.html); on Apr. 4, 2018.

Gubala et al.; Point of care diagnostics: status and future; Analytical Chemistry; 84(2); pp. 487-515; Jan. 2012.

Liu et al.; Progress curve analysis of qRT-PCR reactions using the logistic growth equation; Biotechnology Progress; 27(5); pp. 1407-1414; Sep. 15, 2011.

Pipper et al.; Clockwork PCR including sample preparation; Angew. Chem. Int. Ed.; 47(21); pp. 3900-3904; Apr. 15, 2008.

Roche Diagnostics GMBH; LightCycler 480 instrument Operator's Manual, Software version 1.5; © 2008; 8 pages; Oct. 15, 2014; retrieved from the internet (http://pedrovate.files.wordpress.com/2013/08/lightcyclerc2ae-480-instrument-operators-rnanual.pdf).

Wikipedia; Immunoassay; 4 pages; Feb. 24, 2015; retrieved from the internet (http://en.wikiopedia.org/wiki/Immunoassay).

Wikipedia; Lateral flow test; 4 pages; Feb. 24, 2015; retrieved from the internet (http:en.wikipedia.org/wiki/Lateral__flow__test).

Wikipedia; Polymerase chain reaction; 13 pages; Oct. 15, 2014; retrieved from the internet (http://en.wikipedia.org/wiki/Polymerase__chain__reaction).

Wikipedia; Variants of PCR; 11 pages; Oct. 15, 2014; retrieved from the internet (http://en.wikipedia.org/wiki/Variants__of_PCR#Isothermal__ampiification__methods).

Zhang et al.; Micropumps, microvalves, and micromixers within pcr microfludic chips: Advances and trends; Biotechnology Advances; 25(5); pp. 483-514; Sep. 1, 2007.

Cone et al.; Protocol for Ultraviolet Irradiation of Surfaces to Reduce PCR Contamination; PCR Methods and Applications; Genome Research; 3(3); pp. 515-517; Dec. 1, 1993.

* cited by examiner

Fig. 12
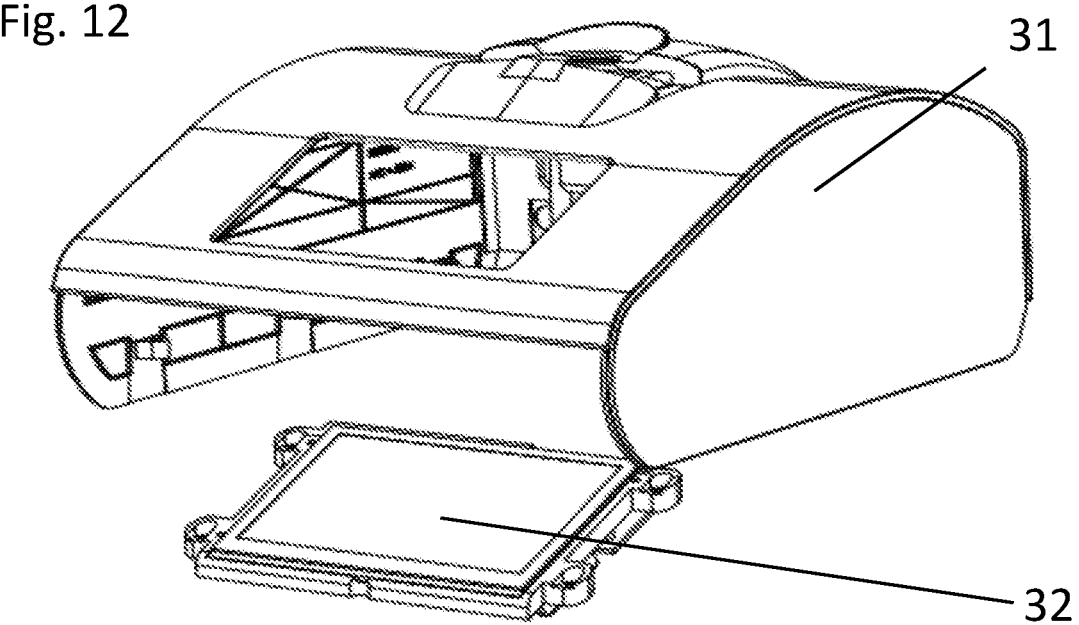
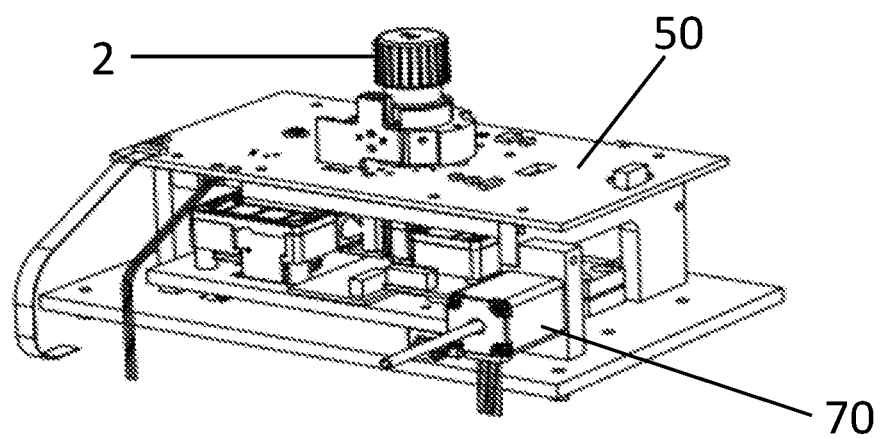
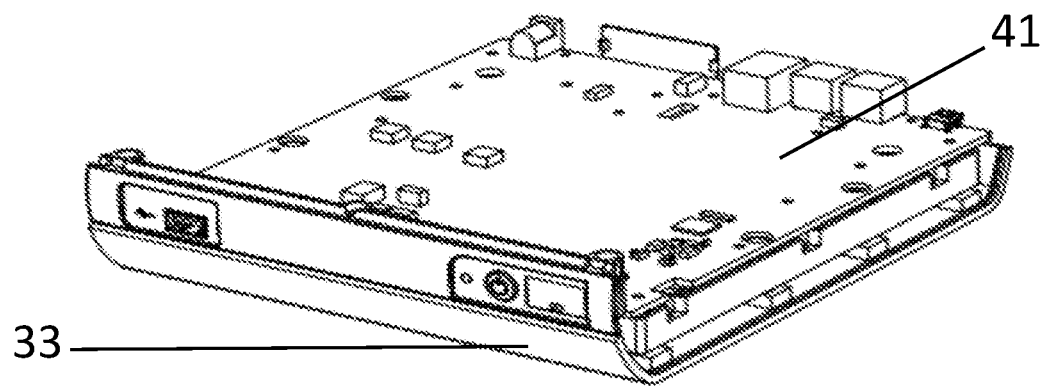

Fig. 34
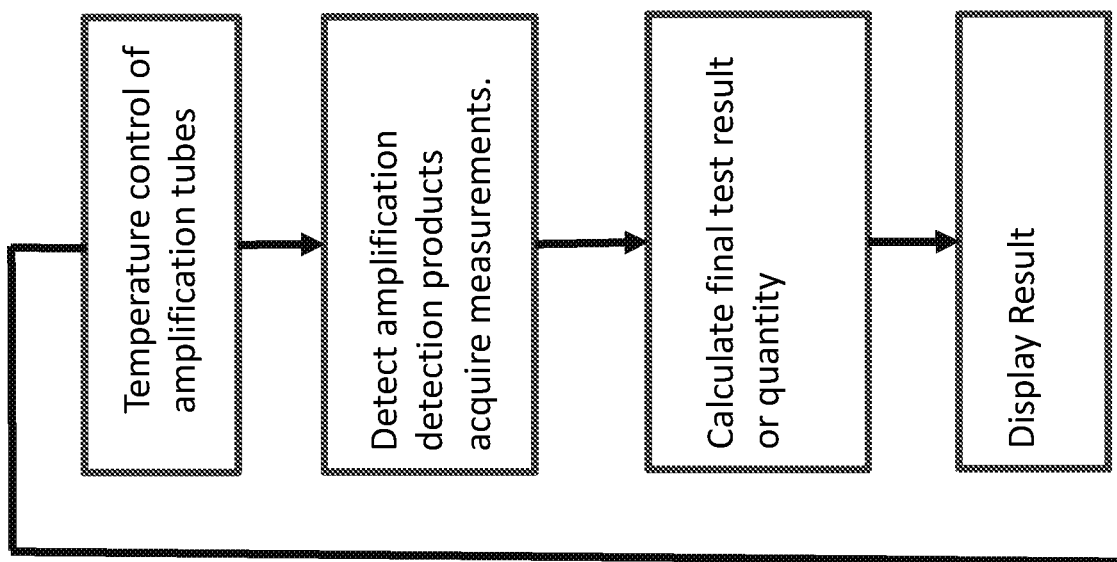
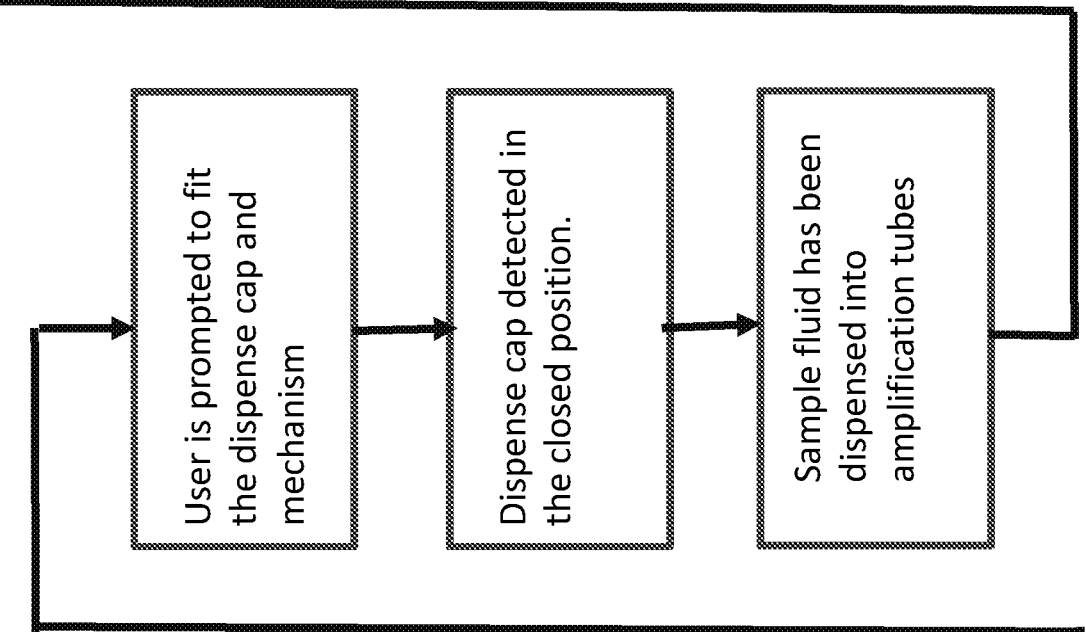
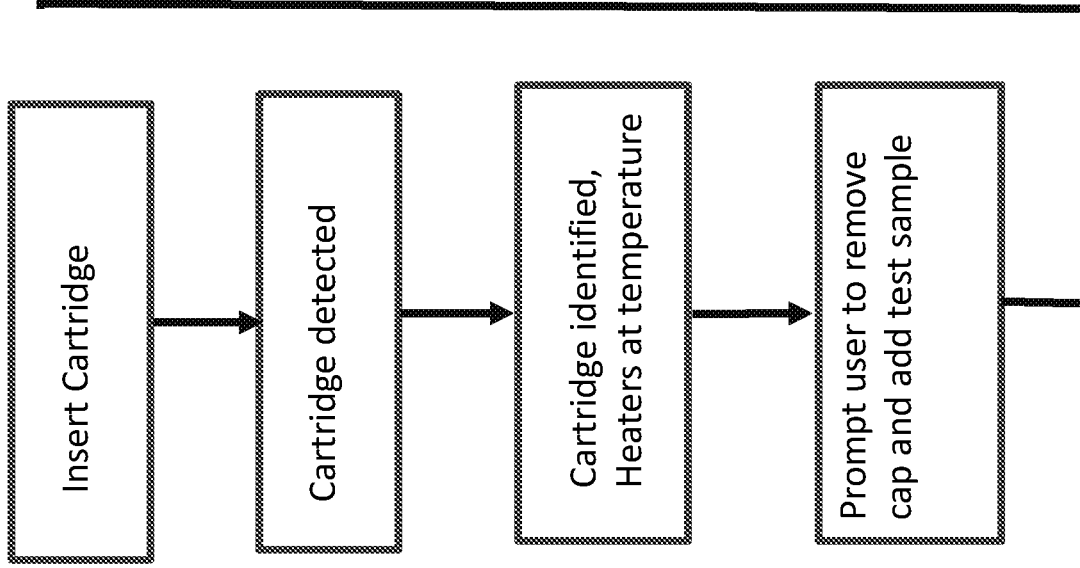

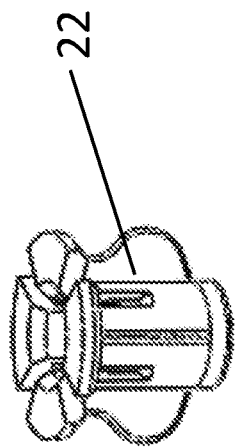
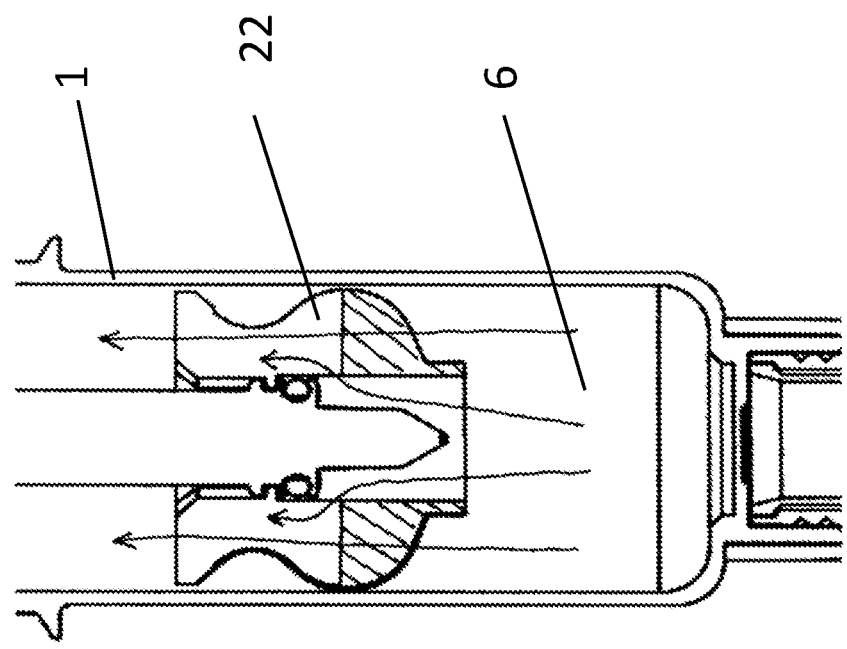

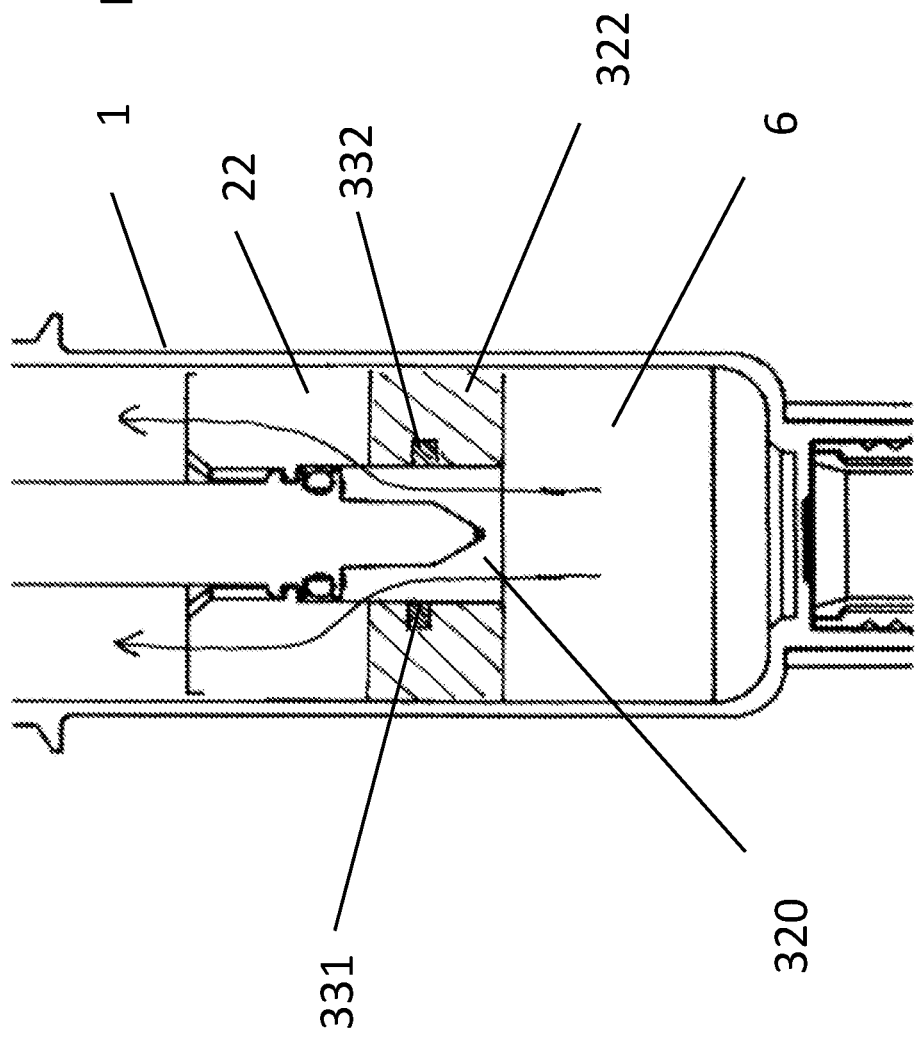

DIAGNOSTIC TEST SYSTEM AND METHOD UTILIZING A CLOSURE/SAMPLE DISPENSING MECHANISM TO DISPENSE A SAMPLE SUBVOLUME FOR TESTING

TECHNICAL FIELD

The present invention relates to a diagnostic test system and method for performing diagnostic tests or analysis of biological samples to aid in environmental, agricultural, scientific, veterinary or medical diagnosis based on detection of the presence or absence of one or more specific analytes in a sample and/or determining their quantities in the sample. The analyte may be detected using methods of molecular DNA amplification and detection of specific genetic markers, for example.

BACKGROUND

The amplification of nucleic acids is important in many fields, including medical, biomedical, environmental, veterinary and food safety testing. In general, nucleic acids are amplified by one of two methods: polymerase chain reaction (PCR) or isothermal amplification, both of which are described below.

Polymerase Chain Reaction (PCR)

As described in the Wikipedia[1] at http://en.wikipedia.org/wiki/Polymerase_chain_reaction:

[1] The Wikipedia text quoted herein is released under CC-BY-SA, see http://creativecommons.org/licenses/by-sa/3.0.

"The polymerase chain reaction (PCR) is a scientific technique in molecular biology to amplify a single or a few copies of a piece of DNA across several orders of magnitude, generating thousands to millions of copies of a particular DNA sequence.

Developed in 1983 by Kary Mullis, PCR is now a common and often indispensable technique used in medical and biological research labs for a variety of applications. These include DNA cloning for sequencing, DNA-based phylogeny, or functional analysis of genes; the diagnosis of hereditary diseases; the identification of genetic fingerprints (used in forensic sciences and paternity testing); and the detection and diagnosis of infectious diseases. In 1993, Mullis was awarded the Nobel Prize in Chemistry along with Michael Smith for his work on PCR.

The method relies on thermal cycling, consisting of cycles of repeated heating and cooling of the reaction for DNA melting and enzymatic replication of the DNA. Primers (short DNA fragments) containing sequences complementary to the target region along with a DNA polymerase (after which the method is named) are key components to enable selective and repeated amplification. As PCR progresses, the DNA generated is itself used as a template for replication, setting in motion a chain reaction in which the DNA template is exponentially amplified. PCR can be extensively modified to perform a wide array of genetic manipulations.

Almost all PCR applications employ a heat-stable DNA polymerase, such as Taq polymerase, an enzyme originally isolated from the bacterium *Thermus aquaticus*. This DNA polymerase enzymatically assembles a new DNA strand from DNA building-blocks, the nucleotides, by using single-stranded DNA as a template and DNA oligonucleotides (also called DNA primers), which are required for initiation of DNA synthesis. The vast majority of PCR methods use thermal cycling, i.e., alternately heating and cooling the PCR sample to a defined series of temperature steps. These thermal cycling steps are necessary first to physically separate the two strands in a DNA double helix at a high temperature in a process called DNA melting. At a lower temperature, each strand is then used as the template in DNA synthesis by the DNA polymerase to selectively amplify the target DNA. The selectivity of PCR results from the use of primers that are complementary to the DNA region targeted for amplification under specific thermal cycling conditions.

PCR Principles and Procedure

PCR is used to amplify a specific region of a DNA strand (the DNA target). Most PCR methods typically amplify DNA fragments of up to ~10 kilo base pairs (kb), although some techniques allow for amplification of fragments up to 40 kb in size.

A basic PCR set up requires several components and reagents. These components include:

DNA template that contains the DNA region (target) to be amplified.

Two primers that are complementary to the 3' (three prime) ends of each of the sense and anti-sense strand of the DNA target.

Taq polymerase or another DNA polymerase with a temperature optimum at around 70° C.

Deoxynucleoside triphosphates (dNTPs; nucleotides containing triphosphate groups), the building-blocks from which the DNA polymerase synthesizes a new DNA strand.

Buffer solution, providing a suitable chemical environment for optimum activity and stability of the DNA polymerase.

Divalent cations, magnesium or manganese ions; generally $Mg^{2+}$ is used, but $Mn^{2+}$ can be utilized for PCR-mediated DNA mutagenesis, as higher $Mn^{2+}$ concentration increases the error rate during DNA synthesis.

Monovalent cation potassium ions.

The PCR is commonly carried out in a reaction volume of 10-200 μl in small reaction tubes (0.2-0.5 ml volumes) in a thermal cycler. The thermal cycler heats and cools the reaction tubes to achieve the temperatures required at each step of the reaction (see below). Many modern thermal cyclers make use of the Peltier effect, which permits both heating and cooling of the block holding the PCR tubes simply by reversing the electric current. Thin-walled reaction tubes permit favourable thermal conductivity to allow for rapid thermal equilibration. Most thermal cyclers have heated lids to prevent condensation at the top of the reaction tube. Older thermocyclers lacking a heated lid require a layer of oil on top of the reaction mixture or a ball of wax inside the tube.

Procedure

Typically, PCR consists of a series of 20-40 repeated temperature changes, called cycles, with each cycle commonly consisting of 2-3 discrete temperature steps, usually three . . . . The cycling is often preceded by a single temperature step (called hold) at a high temperature (>90° C.), and followed by one hold at the end for final product extension or brief storage. The temperatures used and the length of time they are applied in each cycle depend on a variety of parameters. These include the enzyme used for DNA synthesis, the concentration of divalent ions and dNTPs in the reaction, and the melting temperature (Tm) of the primers.

Initialization step: This step consists of heating the reaction to a temperature of 94-96° C. (or 98° C. if extremely thermostable polymerases are used), which is held for 1-9 minutes. It is only required for DNA polymerases that require heat activation by hot-start PCR.

Denaturation step: This step is the first regular cycling event and consists of heating the reaction to 94-98° C. for 20-30 seconds. It causes DNA melting of the DNA template by disrupting the hydrogen bonds between complementary bases, yielding single-stranded DNA molecules.

Annealing step: The reaction temperature is lowered to 50-65° C. for 20-40 seconds allowing annealing of the primers to the single-stranded DNA template. Typically the annealing temperature is about 3-5 degrees Celsius below the Tm of the primers used. Stable DNA-DNA hydrogen bonds are only formed when the primer sequence very closely matches the template sequence. The polymerase binds to the primer-template hybrid and begins DNA synthesis.

Extension/elongation step: The temperature at this step depends on the DNA polymerase used; Taq polymerase has its optimum activity temperature at 75-80° C., and commonly a temperature of 72° C. is used with this enzyme. At this step the DNA polymerase synthesizes a new DNA strand complementary to the DNA template strand by adding dNTPs that are complementary to the template in 5' to 3' direction, condensing the 5'-phosphate group of the dNTPs with the 3'-hydroxyl group at the end of the nascent (extending) DNA strand. The extension time depends both on the DNA polymerase used and on the length of the DNA fragment to be amplified. As a rule-of-thumb, at its optimum temperature, the DNA polymerase will polymerize a thousand bases per minute. Under optimum conditions, i.e., if there are no limitations due to limiting substrates or reagents, at each extension step, the amount of DNA target is doubled, leading to exponential (geometric) amplification of the specific DNA fragment.

Final elongation: This single step is occasionally performed at a temperature of 70-74° C. for 5-15 minutes after the last PCR cycle to ensure that any remaining single-stranded DNA is fully extended.

Final hold: This step at 4-15° C. for an indefinite time may be employed for short-term storage of the reaction.

PCR Stages

The PCR process can be divided into three stages:

Exponential amplification: At every cycle, the amount of product is doubled (assuming 100% reaction efficiency). The reaction is very sensitive: only minute quantities of DNA need to be present.

Leveling off stage: The reaction slows as the DNA polymerase loses activity and as consumption of reagents such as dNTPs and primers causes them to become limiting.

Plateau: No more product accumulates due to exhaustion of reagents and enzyme.

PCR Optimization

In practice, PCR can fail for various reasons, in part due to its sensitivity to contamination causing amplification of spurious DNA products. Because of this, a number of techniques and procedures have been developed for optimizing PCR conditions. Contamination with extraneous DNA is addressed with lab protocols and procedures that separate pre-PCR mixtures from potential DNA contaminants. This usually involves spatial separation of PCR-setup areas from areas for analysis or purification of PCR products, use of disposable plasticware, and thoroughly cleaning the work surface between reaction setups. Primer-design techniques are important in improving PCR product yield and in avoiding the formation of spurious products, and the usage of alternate buffer components or polymerase enzymes can help with amplification of long or otherwise problematic regions of DNA. Addition of reagents, such as formamide, in buffer systems may increase the specificity and yield of PCR.

Amplification and Quantification of DNA

Because PCR amplifies the regions of DNA that it targets, PCR can be used to analyse extremely small amounts of sample. This is often critical for forensic analysis, when only a trace amount of DNA is available as evidence. PCR may also be used in the analysis of ancient DNA that is tens of thousands of years old. These PCR-based techniques have been successfully used on animals, such as a forty-thousand-year-old mammoth, and also on human DNA, in applications ranging from the analysis of Egyptian mummies to the identification of a Russian tsar. Quantitative PCR methods allow the estimation of the amount of a given sequence present in a sample—a technique often applied to quantitatively determine levels of gene expression. Real-time PCR is an established tool for DNA quantification that measures the accumulation of DNA product after each round of PCR amplification.

PCR in Diagnosis of Diseases

PCR permits early diagnosis of malignant diseases such as leukemia and lymphomas, which is currently the highest-developed in cancer research and is already being used routinely. (See the studies cited in the EUTOS For CML study article at http://www.eutos.org/content/molecular_monitoring/information/per_testing/, especially notes 10-13.) PCR assays can be performed directly on genomic DNA samples to detect translocation-specific malignant cells at a sensitivity that is at least 10,000-fold higher than that of other methods.

PCR also permits identification of non-cultivatable or slow-growing microorganisms such as mycobacteria, anaerobic bacteria, or viruses from tissue culture assays and animal models. The basis for PCR diagnostic applications in microbiology is the detection of infectious agents and the discrimination of non-pathogenic from pathogenic strains by virtue of specific genes.

Viral DNA can likewise be detected by PCR. The primers used need to be specific to the targeted sequences in the DNA of a virus, and the PCR can be used for diagnostic analyses or DNA sequencing of the viral genome. The high sensitivity of PCR permits virus detection soon after infection and even before the onset of disease. Such early detection may give physicians a significant lead in treatment. The amount of virus ("viral load") in a patient can also be quantified by PCR-based DNA quantitation techniques (see below).

Isothermal Amplification Methods

As described in the Wikipedia[1] at http://en.wikipedia.org/wiki/Variants_of_PCR#Isothermal_amplification_methods:

"Some DNA amplification protocols have been developed that may be used alternatively to PCR:

Helicase-dependent amplification is similar to traditional PCR, but uses a constant temperature rather than cycling through denaturation and annealing/extension steps. DNA Helicase, an enzyme that unwinds DNA, is used in place of thermal denaturation.

PAN-AC also uses isothermal conditions for amplification, and may be used to analyze living cells.

Nicking Enzyme Amplification Reaction referred to as NEAR, is isothermal, replicating DNA at a constant temperature using a polymerase and nicking enzyme.

Recombinase Polymerase Amplification (RPA). The method uses a recombinase to specifically pair primers with double-stranded DNA on the basis of homology, thus directing DNA synthesis from defined DNA sequences present in the sample. Presence of the target sequence initiates DNA amplification, and no thermal or chemical melting of DNA is required. The reaction progresses rapidly and results in specific DNA amplification from just a few target copies to detectable levels typically within 5-10 minutes. The entire reaction system is stable as a dried formulation and does not need refrigeration. RPA can be used to replace PCR (Polymerase Chain Reaction) in a variety of laboratory applications and users can design their own assays.

Detection of Genetic Targets within a Test Sample.

After DNA amplification there will be a large number of copies of the target genetic sequences in the test solution. In a diagnostic test assay, specific markers can be designed that will link to the target sequences, and once bonded provide an optical signal or optical change that can be detected external to the test tube. This optical signal may be a change in the colour and/or opacity of the sample as measured by a change in the optical absorption of the sample at specific optical wavelengths. The output signal may also be by way of direct light output from the sample, where the marker, when activated by target bonding event, triggers release of bioluminescence light output. The optical detection output may also be by a change in the fluorescence of the solution, which may be from a fluorescence marker beacon. In this case, each marker molecule is configured with a florescence quencher in close proximity to a fluorescence atom or arrangement of atoms. This marker molecule is configured such that when it selectively binds to a target DNA sequence in the test solution, the quencher and fluorophore are separated and a strong fluorescence signal can then be detected by the action of the fluorophore. In this arrangement, the overall florescence intensity of the target solution is indicative of the relative amount of target generic material in the test solution. This signal can then be used to form the basis of a diagnostic test to determine the presence or absence and the relative quantity of the target material in the sample under test.

Control Channel and Multiplexing.

Within a single test well, it is possible to have several different markers present that will provide an optical output based on bonding to several different target genetic DNA sequences. In this case several different sensors are used or a sensor with more than one selective output is used. For example, in a two channel system, two different fluorescence markers may be employed, and these will be detected by two different fluorescence sensors configured to detect emissions in respective frequency ranges specific to the respective fluorescence markers to allow the channels to be discriminated.

This approach can be used to provide a control channel where the test assay chemistry is configured such that the control target should always be present if the test process is run correctly. In this case, the output of the control channel is used to confirm that the test process has been run correctly by the system, and to confirm that test results obtained by other channels measured by the system are valid.

This approach can be also used to test for more than one target genetic sequence within each test well as a multiplexed test.

Multiple test wells may be used, with each well running differently configured amplification chemistry and a different set of target markers. Control channels may operate in one or more wells and cover tests operated other wells in the test. By this arrangement a number of tests can be conducted on a single sample as a different approach to multiplexing.

Prior art diagnostic test systems and apparatuses, in particular nucleic acid amplification and detection instruments, are typically large, complex and costly, and require sample preparation steps that must be conducted independently of the instrument. These preparation steps typically require a trained technical operator, and this operator and the test preparation environment can be exposed to hazardous samples such as body fluids and infectious agents, and the process is at risk from incorrect manual operations, including spills and incorrect reagent additions.

The resulting test sample must then be accurately subsampled and transferred by a manual transfer step, typically a skilled pipetting operation. This approach requires a trained technical operator and a number of separate tubes and transfer devices, all of which will be contaminated by the sample and must be correctly handled and disposed of individually.

In these prior art approaches, the test sample is not sealed from the environment during the process of sample preparation and transfer into test tubes in the test instrument. This exposure to the sample can present infection agent risks to users and others, and can also contaminate the test instrument and test area, resulting in incorrect diagnostic results in subsequent tests.

It is desired to provide a diagnostic test system and method that alleviate one or more difficulties of the prior art, or that at least provide a useful alternative.

SUMMARY

In accordance with some embodiments of the present invention, there is provided a diagnostic test system, including:
  a diagnostic test assembly; and
  a diagnostic test apparatus to receive and interact with the diagnostic test assembly to perform a diagnostic test on a biological or environmental sample therein;
  wherein the diagnostic test assembly includes:
  a sample preparation reservoir to receive the biological or environmental sample into a sample preparation fluid contained in the sample preparation reservoir for preparation of a sample fluid therefrom, the sample preparation reservoir initially providing an open volume free of obstructions such that a swab carrying the biological or environmental sample can be used to stir the sample preparation fluid in the sample preparation reservoir and to wash the biological or environmental sample from the swab into the sample preparation fluid;
  a sample dispensing mechanism for insertion into the sample preparation reservoir after receipt of the biological or environmental sample therein;
  a closure to seal the sample preparation reservoir after receipt of the biological or environmental sample and the sample dispensing mechanism therein;
  at least one diagnostic test reservoir coupled to the sample preparation reservoir; and
  at least one seal between the sample preparation reservoir and the at least one diagnostic test reservoir to prevent fluid movement between the sample preparation reservoir and the at least one diagnostic test reservoir;
  wherein the sample dispensing mechanism is operable to disrupt the at least one seal to allow sample fluid to enter the at least one diagnostic test reservoir from the sample preparation reservoir, and to dispense a predetermined sub-volume of the sample fluid from the sample preparation reservoir into the at least one diagnostic test reservoir for diagnostic testing and detection therein while preventing further fluid movement between the sample preparation reservoir and the at least one diagnostic test reservoir.

In some embodiments, the sample dispensing mechanism is attached to the closure so that an act of applying the closure to the sample preparation reservoir also effects the insertion of the sample dispensing mechanism into the sample preparation reservoir.

In some embodiments, a single action by a user causes the sample dispensing mechanism to disrupt the at least one seal and to dispense the sample fluid from the sample preparation reservoir into the at least one diagnostic test reservoir.

In some embodiments, the single action by the user is a sustained screwing action applied to the closure relative to the sample preparation reservoir, wherein the screwing action causes operation of the sample dispensing mechanism and seals the sample preparation reservoir.

In some embodiments, the diagnostic test apparatus is configured to determine completion of the operation of the sample dispensing mechanism and, responsive to the determination, to proceed with diagnostic testing of the contents of the at least one diagnostic test reservoir.

In some embodiments, the closure includes a screw thread, and the diagnostic test apparatus includes at least one sensing component configured to determine a degree of rotation and/or thread progression of the closure, and the diagnostic test apparatus is configured to prompt a user to complete the closure operation if the at least one sensing component has determined that the closure operation is incomplete; and to automatically progress to a next stage of diagnostic testing if the closure operation has been determined as being complete.

In some embodiments, the diagnostic test assembly includes a second closure that seals the sample preparation fluid within the sample preparation reservoir prior to use, and that is removed to allow the biological or environmental sample to be added to the sample preparation fluid contained in the sample preparation reservoir.

In some embodiments, the sample dispensing mechanism includes:
  a dispensing chamber that forms a second seal against the at least one seal to trap the predetermined sub-volume of the sample fluid within the dispensing chamber;
  a piercing member that disrupts the at least one seal by forming at least one opening therein; and
  a plunger mechanism that forms a sliding seal with an internal surface of the dispensing chamber, wherein the sliding seal is configured to slide along the internal surface of the dispensing chamber to dispense the predetermined sub-volume of the sample fluid therefrom, through the at least one opening, and into the at least one diagnostic test reservoir.

In some embodiments, the dispensing chamber includes an outer surface having mutually spaced chamber locating features extending therefrom and configured to align the dispensing chamber centrally of the sample preparation reservoir and allow sample fluid to flow between the chamber locating features as the sample dispensing mechanism is inserted into the sample preparation reservoir.

In some embodiments, the sample dispensing mechanism is configured so that a single action performed by a user causes two stages of operation of the sample dispensing mechanism, including a first stage of operation that traps the predetermined sub-volume of the sample fluid within the dispensing chamber, and a second stage of operation wherein the sample fluid is dispensed from the dispensing chamber.

In some embodiments, the sample dispensing mechanism includes a force sequencing component that is reconfigured or broken to allow the second stage of operation.

In some embodiments, the force sequencing component includes a breakable component that is configured to break to allow operation of the sample dispensing mechanism to proceed from the first stage of operation to the second stage of operation.

In some embodiments, the force sequencing component includes a collapsible or crushable spacer that presses against and causes the dispensing chamber to seal in the first stage of operation, and in the second stage of operation is collapsed or crushed to maintain the seal, perform the perforation action, and operate the plunger to dispense the sample fluid from the dispensing chamber.

In some embodiments, the dispensing chamber is initially configured so that, as the sample dispensing mechanism is inserted into the sample preparation reservoir, the sample fluid is forced to flow around the outside of the dispensing chamber before it can flow into the dispensing chamber, wherein the fluid that flows around the outside of the dispensing chamber is caused to flow through a filter or porous filler material that retains and/or traps particles and debris and/or incorporates biological or chemical components that bind to or capture components of the sample fluid that may otherwise inhibit or interfere with the diagnostic test or amplification process.

In some embodiments, the sample preparation reservoir includes magnetic particles with the sample preparation fluid, the surface of the magnetic particles being coated or functionalised to bind with and capture at least one predetermined target species of the biological or environmental sample when the magnetic particles are mixed within the sample fluid, and the sample dispensing mechanism is configured so that, as the sample dispensing mechanism is inserted into the sample preparation reservoir, the sample fluid is forced to flow through the dispensing chamber, and one or more magnets are located in close proximity to the inside surface of the dispensing chamber so that magnetic particles contained within the sample fluid and have captured target species are attracted to and held against the internal surface of the dispensing chamber, such that the plunger mechanism that forms a sliding seal with the internal surface of the dispensing chamber collects the magnetic particles held against the internal surface and dispenses them into the at least one diagnostic test reservoir to provide an increased concentration of the at least one predetermined target species in the predetermined sub-volume of the sample fluid dispenses into the at least one diagnostic test reservoir.

In some embodiments, at least one of the closure and the sample preparation reservoir is configured to prevent or at least inhibit removal of the closure from the sample preparation reservoir so that the fluids remain sealed within the diagnostic test assembly.

In some embodiments, the at least one diagnostic test reservoir includes at least two diagnostic test reservoirs.

In some embodiments, the diagnostic test reservoirs contain different diagnostic test and/or detection reagents selected to perform respective different diagnostic tests and/or to detect respective different target entities.

In some embodiments, the sample preparation reservoir contains reagents for sample preparation including cell lysis, and at least one of the diagnostic test reservoirs is configured for nucleic acid amplification and binding of specific markers to enable an optical output that can be measured by the diagnostic test apparatus to determine a corresponding diagnostic test result.

In some embodiments, the at least one diagnostic test reservoir includes at least one diagnostic test reservoir that is transparent to enable a corresponding test result to be observed visually as a change in emission and/or absorption at one or more specific wavelengths and/or turbidity within the corresponding at least one diagnostic test reservoir.

In some embodiments, at least one of the at least one diagnostic test reservoirs is transparent, and the diagnostic test apparatus is configured to determine a test result in the at least one diagnostic test reservoir by detecting or measuring a change in emission and/or absorption at one or more wavelengths within the at least one diagnostic test reservoir, wherein the diagnostic test apparatus is optionally configured to illuminate the at least one diagnostic test reservoir to enhance or produce the detecting or measuring.

In some embodiments, the diagnostic test apparatus and the diagnostic test assembly include respective alignment and support features configured for mutual engagement to ensure that the diagnostic test assembly is received in a predetermined alignment with respect to the diagnostic test apparatus and to maintain the alignment when the closure is applied to the sample preparation reservoir after receipt of the biological or environmental sample and the sample dispensing mechanism therein.

In some embodiments, the diagnostic test apparatus includes one or more components configured to apply a changing and/or moving magnetic field to the diagnostic test assembly to cause corresponding movements of magnetic particles within at least one of the sample preparation reservoir and the at least one diagnostic test reservoir, and thereby cause mixing of the sample and sample preparation fluid therein.

In some embodiments, the diagnostic test apparatus and the diagnostic test assembly are configured to allow the diagnostic test apparatus to independently control the temperatures of the sample preparation reservoir and the at least one diagnostic test reservoir.

In some embodiments, the diagnostic test apparatus includes one or more image sensors configured to generate image data representing one or more images of at least a portion of the diagnostic test assembly, wherein the images represent at least one of:
(i) fluid distribution within at least one of the at least one diagnostic test reservoir and the sample preparation reservoir, and the diagnostic test apparatus is configured to process the image data to monitor dispensing of the sample fluid, and to proceed to a next stage of diagnostic testing if the monitoring has determined that the dispensing is complete; and
(ii) a fluid volume contained within the at least one diagnostic test reservoir, and the diagnostic test apparatus is configured to process the image data to allow compensation for the volume tolerances in the dispensed fluid to allow for improved test result determination.

In some embodiments, the diagnostic test apparatus includes one or more optical sensors mounted to a translation stage under control of a controller of the diagnostic test apparatus so that the optical sensors can measure optical absorption or emission or fluorescence from one or more selected diagnostic test reservoirs of the diagnostic test assembly.

In some embodiments, the diagnostic test apparatus includes at least one ultra violet (UV) emission source to denature samples contained within the diagnostic test assembly following a diagnostic test to inhibit contamination in the event of sample fluid escaping from the diagnostic test assembly.

In accordance with some embodiments of the present invention, there is provided a diagnostic test method, including the steps of:
placing a diagnostic test assembly into a receiving port of a diagnostic test apparatus configured to perform a diagnostic test on a biological or environmental sample therein;
adding the biological or environmental sample into a sample preparation fluid contained in a sample preparation reservoir of the diagnostic test assembly for preparation of a sample fluid therein;
after the adding step, inserting a sample dispensing mechanism into the sample preparation reservoir and applying a closure thereto;
operating the sample dispensing mechanism to disrupt at least one seal between the sample preparation reservoir and at least one diagnostic test reservoir of the diagnostic test apparatus to allow sample fluid to enter the at least one diagnostic test reservoir from the sample preparation reservoir, and to dispense a predetermined sub-volume of the sample fluid from the sample preparation reservoir into the at least one diagnostic test reservoir for diagnostic testing and detection therein while preventing further fluid movement between the sample preparation reservoir and the at least one diagnostic test reservoir.

In some embodiments, the sample dispensing mechanism is attached to the closure so that the applying of the closure to the sample preparation reservoir also effects the insertion of the sample dispensing mechanism into the sample preparation reservoir.

In some embodiments, a single action by a user causes the operation of the sample dispensing mechanism, the single action being a sustained screwing action applied to the closure relative to the sample preparation reservoir, wherein the screwing action causes operation of the sample dispensing mechanism and seals the sample preparation reservoir.

Also described herein is a diagnostic test instrument or apparatus, including:
an instrument housing with an access port to accept a plastic cartridge assembly.
A sensor or switch to detect the insertion or presence of the cartridge inserted into the apparatus.
controller electronics and associated internal electronics, microprocessor and memory to run a software program and save data for future recall and use.
Electrical interface connectors for connection of USB, serial or Ethernet connected peripherals interfaces and external memory devices.
embedded software to provide functions to sequence processing of the instrument, the cartridge and acquire diagnostic test measurements for interpretation determination of test outcome.
a temperature controlled sample chamber heater block to provide heating and temperature control of the upper sample chamber section of the cartridge assembly.
a temperature controlled heater block to provide heating and temperature control of the upper contact specific amplification test wells in an inserted cartridge where this block can apply controlled temperatures including temperature cycling to fluids within the cartridge wells.

Sensors to detect and provide measurement of optical absorption, fluorescence or bioluminescence characteristics of the reagents and added sample fluid reactions within the test wells during the course of the test running and at the completion of the test. The instrument apparatus can incorporate one or more optical sensors where these sensors can be scanned along a row of test wells to allow a multitude of measurements to be recorded for each test well using one or more different sensors.

Optionally, the instrument controller may be located remotely from the physical body of the apparatus such as on a remote server, and manage and control the operation of the apparatus over a communication network such as the internet.

Optionally one or more of the sensors is a coaxial fluorescence sensor where optically filtered emissions from a light emitting diode, or laser illumination of a selective wavelength range is emitted from the sensor lens. This illumination causes optical excitation of the sample in the test well and the same lens also captures florescence emission from the sample at a different shifted wavelength. This sample fluorescence emission is measured and forms a measurement used in determining the diagnostic test result.

Optionally, one or more of the sensors will detect fluorescence within the sample contained within each test well using a separated excitation illumination source to optically excite the test sample and a separated sensor to measure the resulting fluorescence emission.

Optionally, one or more of the sensors uses reflectance or transmission of specific optical illumination wavelength ranges to measure optical reflectance or absorption within the test sample contained within each test well.

Optionally, one or more of the sensors measures light emission from the test sample, where this emission is caused by luminescence or bio-luminescence within the test sample.

Optionally, the sensors are scanned at constant speed past all of the wells, and a multitude of measurements acquired. Subsequent processing of this data set of measurements determines the measurement values to assign to each test well. This analysis considers such characteristics as the relative position or the acquisition time of each measurement and local peaks with an interpolated curve encompassing the acquired measurements.

Optionally, the instrument apparatus incorporates one or more ultraviolet light sources, where this ultraviolet illumination can be turned on or off by the instrument controller.

Optionally, the instrument apparatus incorporates one or more reference targets within the field of view of the fluorescence or optical absorption sensors.

Cartridge

The diagnostic test cartridge includes one or more diagnostic test reservoirs also referred to herein for convenience as 'test tubes' close coupled with a separating wall to a sample preparation reservoir within the cartridge. The sample preparation reservoir is fully sealed from the coupled test tubes, and is typically supplied pre-filled with a volume of sample preparation fluid and a removable closure.

In use, the test cartridge is supported and heated within the test apparatus, and the removable closure is removed to add a sample. The sample can be any biological or chemical sample for which a suitable diagnostic test and test display chemistry reagents are incorporated within the coupled test tube(s).

The test cartridge is supplied with an additional cap with an attached dispensing mechanism. This additional cap incorporates a dispensing mechanism and is fitted after the initial cap has been removed and the sample added. As the additional cap and dispensing mechanism is inserted and the cap is closed by an action such as screwing it closed, the dispensing mechanism perforates the base of the sample chamber and dispenses a measured volume of prepared sample fluid into the one or more test tubes. This cap then closes and seals the sample within the cartridge assembly Alternatively, the first cap, once removed, can have the dispensing mechanism fitted to it, in a separate operation, to forming the additional cap with an included dispensing mechanism ready to be refitted to operate a dispense function and close the cartridge.

Optionally, after the sample is added, the dispensing mechanism itself is directly inserted and then a cap is fitted and the action of closing this cap, such as screwing the cap closed, operates the dispensing mechanism and close the cartridge.

Cartridge Operation a test cartridge with a removable closure or cap to allow addition of a test sample, where the cartridge incorporates a sample preparation reservoir containing a sample preparation fluid such as a buffer or lysis solution to assist with preparation of the sample and can include separation of target DNA material from within the sample cells. The sample preparation fluid reservoir section of the cartridge is a closed volume to reliably retain the sample preparation solution until such time as a sub-volume is dispensed through perforations in the otherwise sealed wall between the reservoir and the coupled test tubes.

A test instrument that supports a metallic or otherwise thermally conductive block in contact with the diagnostic test reservoir(s), a controlled temperature under electronic control using a single or multitude of feedback temperature sensors mounted on the block. This heated block is configured to heat and control the temperature of the fluid contents of the diagnostic test reservoir(s) through the plastic well wall for the purposes of obtaining a sample chemical or enzymatic reaction on material within the sample to expose target DNA.

Optionally, a metallic or otherwise thermally conductive block is in contact with the cartridge fluid volumes provides a controlled temperature under electronic control using a single or multitude of feedback temperature sensors mounted on the block. This block os configured to heat the internal test fluids through the cartridge walls to a known temperature for the purposes of sample preparation and cell lysis prior to flow into the test wells.

Optionally, the temperature sensors can include one or more Infrared emission non-contact temperature sensors, where these sensors are configured to read the block temperature or the actual temperature of the fluid in the reaction test wells.

A metallic or otherwise thermally conductive block in contact with a diagnostic test reservoir or 'test well' or optionally a plurality of test wells provides a controlled temperature under electronic control using a single or multitude of feedback temperature sensors mounted on the block. This heated block is configured to heat and control the temperature of the fluid contents of the test wells through the plastic well walls for the purposes of obtaining a test reaction including iso-thermal or PCR nucleic acid, DNA amplification.

UV Illumination

Ultraviolet illumination is used to decontaminate and denature the contents of the test cartridge including the contents of the test wells at the completion of a test.

Optionally, the ultraviolet illumination is used to denature and breakdown genetic nucleic acid products, including the products of nucleic acid amplification within each test well, at the completion of the test. This denaturing and breakdown of genetic DNA material by ultraviolet illumination to prevent any contamination of the system or its environment by amplicons if the cartridge is subsequently damaged, or leaks and to prevent this material inadvertently being introduced into a subsequent test and causing an erroneous test result.

Optionally, the ultraviolet illumination is carried along with the detection sensors on a carriage that can mechanically scan along a plurality of test wells. This arrangement allows a single focused ultraviolet source to illuminate each well in turn during a controlled decontamination scan.

Optionally, the ultraviolet source is made up of one or more ultraviolet light emitting diodes.

Optical Measurement

Optionally, a set of optical measurement sensors can view the test well contents through an optical widow or port in the test well and its surrounding heater block to produce measurements of optical absorption, florescence or bioluminescence.

Optionally, the optical sensors are mounted on carriage that that can be moved linearly along the test wells to scan and provide an optical measurement for each well in a set of wells.

Optionally, the linear scan is performed by the carriage at a constant speed, and the peak reading or an average of readings associated with each test well is assigned as that the optical reading for the well.

Optionally, the carriage moves on a linear slide arrangement that can be driven by a stepper motor to provide accurate position and motion control under software control and electrical interface to the instrument controller.

Optionally, a set of reference samples are mounted within the instrument such that the sensors used to acquire well measurements can also acquire measurements of the reference samples.

Optionally, a specific set of sensor measurements acquired when measuring the reference samples are saved to a non-volatile memory location within the instrument controller, such that these saved readings can be used in the future to confirm that subsequent readings are within a given tolerance range of the saved readings for each respective sensor and reference sample.

Optionally, the capability to compare the sensor readings of the reference materials mounted within the instrument against previously saved readings for the same sample for the purposes of the instrument controller performing an instrument self test.

Imaging Sensor and Image Analysis

Optionally, code marks or a barcode or a two-dimensional code, such as a QR code is provided on the surface of the cartridge assembly.

Optionally, the coded marks are printed by laser marking, laser discoloration or laser etching on a plastic surface of the cartridge.

Optionally, the image or camera sensor incorporated within the instrument in combination with the illumination incorporated within the instrument acquires an image of a printed code on the cartridge and through a process of image analysis in software, extract the encoded information.

Optionally, the information encoded within the printed code includes one or more of following data: the test identification, details of the test sequence and temperatures to be applied to run the cartridge, a unique cartridge serial number, the manufacturing batch number for the cartridge, batch specific calibration parameters, the manufacture date of the cartridge and an expiry date after which the cartridge should not be used.

Optionally, the image sensor is used to confirm the sequence progression and correct release and flow of test reagents within the cartridge such that the integrity of the test can be confirmed by the software and used to improve the reliability and safety of the test result. The image sensor is used by the controller to observe internal fluids and the mechanism parts within the cartridge and calculate a control interpretation through the use of image analysis software within the apparatus controller.

Optionally the image sensor confirms the operation and position of the dispensing mechanism to confirm incomplete or correct and complete operation of the cartridge and prompt the user to either complete the operation or at completion, automatically progress to the next step in the apparatus process to acquire the final test result.

Optionally, the liquid reagent is coloured by a visual dye and the test output is a fluorescent signal, such that the reagent colouring does not interfere with the test output but this colour can be used to visually track flow and dispensed levels within the cartridge.

Optionally, the image sensor within the instrument captures images of the coloured reagent within transparent sections of the cartridge and confirms in software image analysis that particular flow requirements have operated correctly.

Optionally, the image data acquired by the image sensor and in subsequent image analysis is used by the software controller to determine the levels of the dispensed sample fluid in each of the test tubes and uses this level to determine that the sample fluid dispensing process has completed correctly. The software controller within the instrument can also use the level of the fluid within test tubes to compensate the test result for tolerances in the dispensing operation. Within the software, the level of the fluid with each test chamber is converted to a volume by using a mathematical model of the tube or by using a look up table. The volume of dispensed fluid can influence the concentration of the test regents within the diagnostic test reservoirs once they have dissolved into the dispensed fluid. By measuring the volume of the dispensed sample fluid, the concentration of reagents within each test tube is calculated. This test result impact can be determined from a series of previously conducted experiments or from a model of the test reactions the effect of test reagent concentration on the test result and the interpretation of the time series measurements of the test to interpret the result can be adjusted or compensated for within the apparatus software.

Optionally, details of the diagnostic test progress steps confirmed by the apparatus sensors including the image sensor and image analysis are included within the associated electronic record or the printed record for the test to provide this information to subsequent test result reviewer and improve confidence and evidence of the correct operation of the test.

Optionally, the cartridge incorporates the chemical and biological reagents required for sample preparation and nucleic acid amplification, genetic sequence binding and optical output using iso-thermal nucleic acid amplification methods.

Optionally, the cartridge incorporates the chemical and biological reagents required for sample preparation and nucleic acid amplification and genetic sequence detection using polymerase chain reaction, PCR, nucleic acid amplification methods.

BRIEF DESCRIPTION OF THE DRAWINGS

Some embodiments of the present invention are hereinafter described, by way of example only, with reference to the accompanying drawings, wherein:

FIG. 12 is an exploded view of the instrument of FIG. 11, showing components of the instrument, including a housing, electronic display module, cartridge interface core with upper and lower heater modules and detection sensors and a base assembly with integrated electronic controller;

FIG. 34 is a flow diagram of a workflow of the instrument;

FIG. 36 is a drawing illustrating fluid flow through and around the dispenser insert of FIGS. 4 to 9, inducing mixing as the dispensing mechanism is pressed into the cartridge;

FIG. 37 is a drawing of the dispense insert in isolation;

FIG. 39 is a cross-sectional side view illustrating a further alternative embodiment of a dispense insert wherein the sample fluid can only flow through an internal bore of the insert as the assembly is pressed into the cartridge; the sample fluid cannot bypass the insert barrel as this region is blocked, and the insert includes a magnet around the bore to collect and concentrate DNA and RNA captured on the surface of magnetic beads.

DETAILED DESCRIPTION

Figure 1:
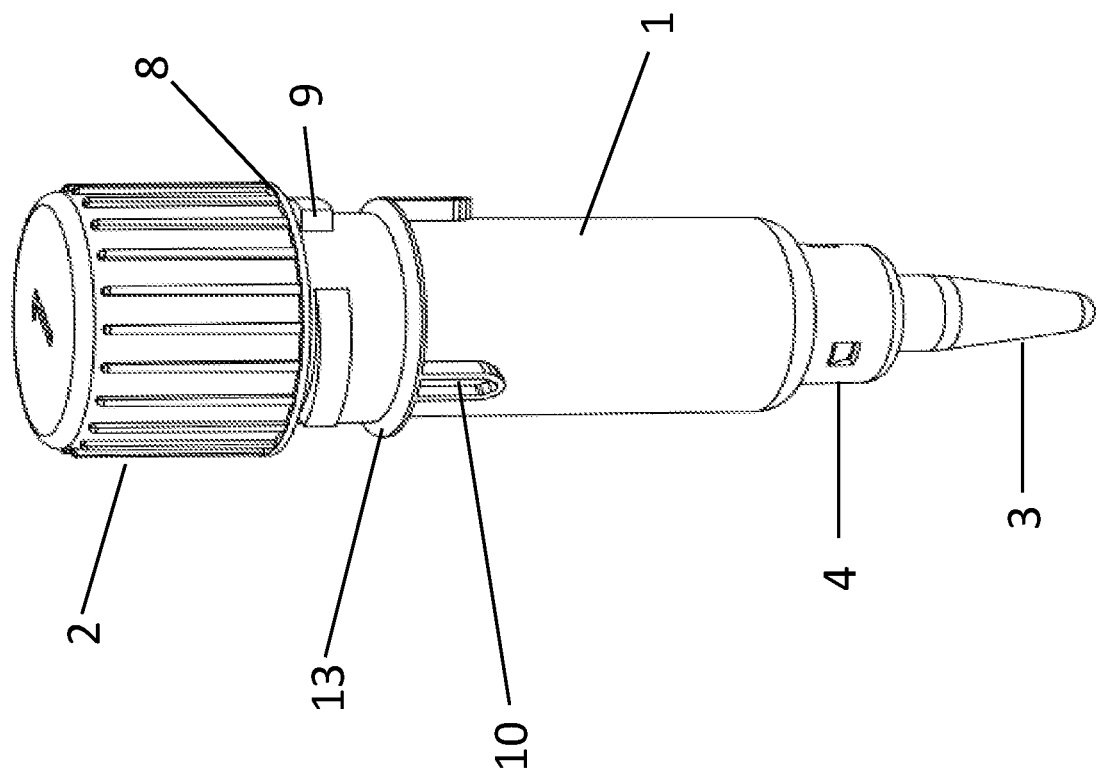
FIG. 1 is an illustration of a diagnostic test assembly or cartridge in accordance with an embodiment of the present invention, with shipping cap fitted.

Embodiments of the present invention include a diagnostic test system, including a diagnostic test apparatus (referred to as 'instrument'), and a diagnostic test assembly (also referred to herein for convenience of reference as a 'cartridge') for use with the diagnostic test instrument to perform a diagnostic test on a biological or environmental sample. As described herein, the cartridge and instrument are easy for a user to operate without requiring the facilities of a general test laboratory.

In the described embodiments, the diagnostic test assembly is provided in the form of a disposable diagnostic test cartridge that is produced prior to a diagnostic test, and already incorporates all of the precursor chemical components (i.e., reagents) to run a specific set of one or more diagnostic tests. The diagnostic test assembly/cartridge is configured so that it can be safely handled without contamination from the environment, or causing contamination of the user or the environment with the test materials, or causing interference with these chemical components or otherwise affecting the subsequent operations of the cartridge, which require interactions with the diagnostic test instrument.

Details of the cartridge and the diagnostic test instrument in accordance with some embodiments of the present invention are described below. By pre-loading specific sample preparation, amplification and marker reagents into the cartridge, the diagnostic test system can be configured to run a specific predetermined set of one or more diagnostic tests, and provide at least one indication of the test outcome(s) to a user. Different versions of the cartridge with the same physical configuration but different loaded reagents can be produced to cover a wide range of test types and diagnostic applications. In some embodiments, the instrument can automatically determine the type of diagnostic test to be performed from an identifier of the cartridge (visual or otherwise), perform the determined diagnostic test(s) and, at the completion of the diagnostic test(s), provide the diagnostic test result(s) to the user by displaying it/them on the user interface display, and/or providing it/them in the form of one or more electronic records or other form of electronic data via any of a number of communications interfaces of the instrument.

To assist with closure removal, warm-up, sample addition, sample preparation, sample dispensing, cartridge closure and test result measurement, the cartridge is supported by, aligned with, heated by and measured by the diagnostic test apparatus/instrument. In some embodiments, the instrument includes separate heater regions for independent temperature control of sample preparation and diagnostic test reservoirs within the cartridge. In a typical test sequence, the cartridge with contained sample preparation fluid is inserted into the instrument, and the instrument detects the presence of the cartridge and begins warming the sample preparation fluid. When the sample preparation fluid has reached the desired temperature, the instrument then prompts the user to add the biological or environmental sample to be analysed. The heating of the sample preparation fluid can be useful to assist with rapid and efficient sample preparation, but might not be necessary for some sample types.

A user of the diagnostic test system wishing to conduct a diagnostic test on a biological or environmental sample introduces the sample into the cartridge. With its closure removed, at this step the cartridge provides an open volume that is free of obstructions, by which is meant that a swab carrying the biological or environmental sample can easily be used to stir the sample preparation fluid in the sample preparation reservoir and to wash the biological or environmental sample from the swab into the sample preparation fluid without encountering obstructions that would impede this step. However, although this characterises the open volume within the cartridge, it will be apparent to those skilled in the art that it is not necessary that a swab be used at all, and samples in any suitable form can be added to the sample preparation fluid by any suitable means.

In the case of biological samples, the step of adding the sample to the sample preparation fluid within the sample preparation reservoir initiates a specific biological and chemical process of sample dilution and cell lysis to prepare the sample material, including its included RNA or DNA nucleic acid, for testing. However, the system is not limited to biological tests, and can, for example, be used to detect the presence of or measure the amounts of trace elements in any type of sample. Other suitable types of diagnostic tests will be apparent to those skilled in the art in light of this disclosure.

Subsequently, or when prompted by the instrument, the user then applies a closure to the sample preparation reservoir, and the action of operating the closure not only seals the sample and sample preparation fluid within the cartridge, but also actuates a dispensing mechanism within the sample preparation reservoir to deliver a sub-sample of predetermined volume into one or more diagnostic test reservoirs within the cartridge.

The instrument then controls the temperature of the one or more diagnostic test reservoirs and the sample fluid and reagents contained within them. This temperature control can be to maintain a fixed temperature, or to follow a predetermined time varying temperature profile, for example, or in the case of a PCR reaction, subjected to thermal cycling with heating and cooling between different fixed temperatures. In any case, a cycle series or a time series of optical measurements of the contents of the test tubes is acquired by the instrument. The instrument can process these measurements to determine a test result which can then be displayed or otherwise provided as an output to a user.

The cartridge protects the reagents in transport and storage prior to running a test, and supports the test process while the diagnostic test is underway. The test reagents, amplification genetic products and contaminants are retained within the cartridge at all times, including at the completion of the test. The sealed cartridge can be removed for disposal at the completion of a test, and the instrument is protected from fluids and contamination at all times.

After the biological sample is added to and then sealed within the cartridge, the user is protected from the biological or chemical hazards of the sample during the subsequent test process and after the cartridge is removed for disposal.

Figure 2:
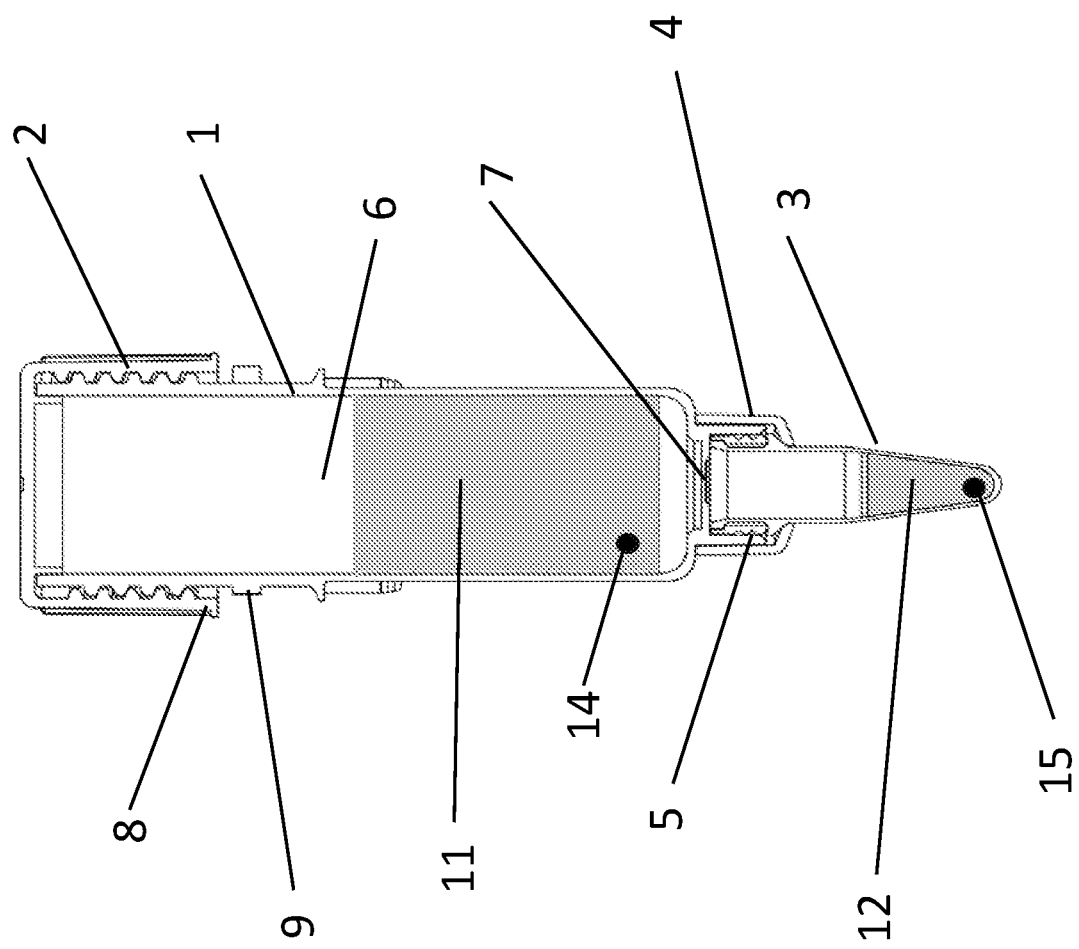
FIG. 2 is a cross-sectional side view of the cartridge of FIG. 1.

As shown in FIGS. 1 and 2, a diagnostic test assembly or 'cartridge' includes a sample reservoir or chamber 1, at least one test reservoir or chamber (also referred to herein as the amplification reservoir or chamber) 3, and at least one seal between the sample preparation reservoir and the at least one diagnostic test reservoir to prevent fluid movement between the sample preparation reservoir and the at least one diagnostic test reservoir. In the described embodiments, the sample reservoir or chamber 1 is in the form of a cylindrical cartridge body 1, and the amplification reservoir or chamber 3 is in the form of an amplification tube coupled to the cartridge body by a securing ring or clip 4 and an elastomer seal 5. The elastomer component 5 provides a seal between the amplification tube 3 and the molded body of the cartridge 1 such that the contents of the amplification tube 3 will not be influenced by environmental contamination prior to use, and cannot escape during and after use. Other coupling and sealing arrangements and configurations will be apparent to those skilled in the art in light of this disclosure, and may be used in other embodiments.

The cartridge is shown in FIGS. 1 and 2 in its shipping configuration prior to use, wherein the sample reservoir or chamber 1 is sealed with a transport cap 2, and is partially filled with a sample preparation or reagent fluid 11, and the amplification tube 3 is partially filled with nucleic acid amplification and associated detection probe reagents 12. These reagents 11, 12 may be in liquid, gel, dried or lyophilised form.

Typically, the sample reagent 11 will be in a liquid form, and will provide the aqueous solution to dilute and expose the test sample DNA or RNA into solution and provide the fluid to dissolve or re-suspend the lyophilised or dried reagents once some of the sample reagent fluid 11 is added to the amplification tube 3. The amplification reagents may be dried or lyophilised or in a gel or liquid format to best suit preparation, loading, storage and transport.

The sample preparation fluid 11 and the amplification and detection reagents 12 are loaded and sealed within the cartridge at the time of manufacture prior to use.

In the shipping configuration prior to use, as shown in FIGS. 1 and 2, the cap 2 has a shorter length such that its lower edge 8 does not contact the molded latching cams 9 on the body of the cartridge. This configuration of the shipping cap 2 allows it to seal the sample preparation liquid reagents 11 within the cartridge body 1, but for the cap 2 to be removable by the user to start a test.

The cartridge body 1 has alignment features 10 that align and engage with mating slots in the instrument to prevent rotation of the cartridge when it is in place in the instrument. This anti-rotation feature allows the user to easily remove the shipping cap and later fit a test cap, all in single handed operation.

The cartridge body 1 contains the sample preparation fluid 11 as it includes a seal on its base at location 7, such that with the cap 2 fitted, it forms a sealed container or reservoir with no fluid communication to the test reservoir or tube 3.

As shown in FIG. 2, in the described embodiment the amplification tube 3 is fitted into a recess molded onto the base of the cartridge body 1 and is sealed with an elastomer seal 5, and retained by the retaining ring 4 that is fixed in place by latch features, friction fit or by use of adhesive or plastic welding. In some embodiments, the amplification tube 3 also incorporates an additional membrane seal over its top, such as a welded plastic membrane or heat sealed foil membrane. This additional seal on the top of the amplification tube 3 is used to retain the amplification reagents 12 prior to assembly onto the cartridge, and facilitates loading and sealing of the amplification tube in a separate manufacturing operation and subsequent assembly onto the cartridge body 1. This seal also provides additional protection of the amplification tube contents against moisture diffusion through the wall of the upper sample reagent chamber of the cartridge.

In some embodiments, the amplification tube 3 is supplied in separated packaging and is only clipped or screwed into place onto the cartridge body 1 just prior to starting the test.

To run a test, the cartridge is inserted into the instrument such that cartridge body 1 is supported and the anti-rotation features 10 are engaged with the instrument.

Figure 11:
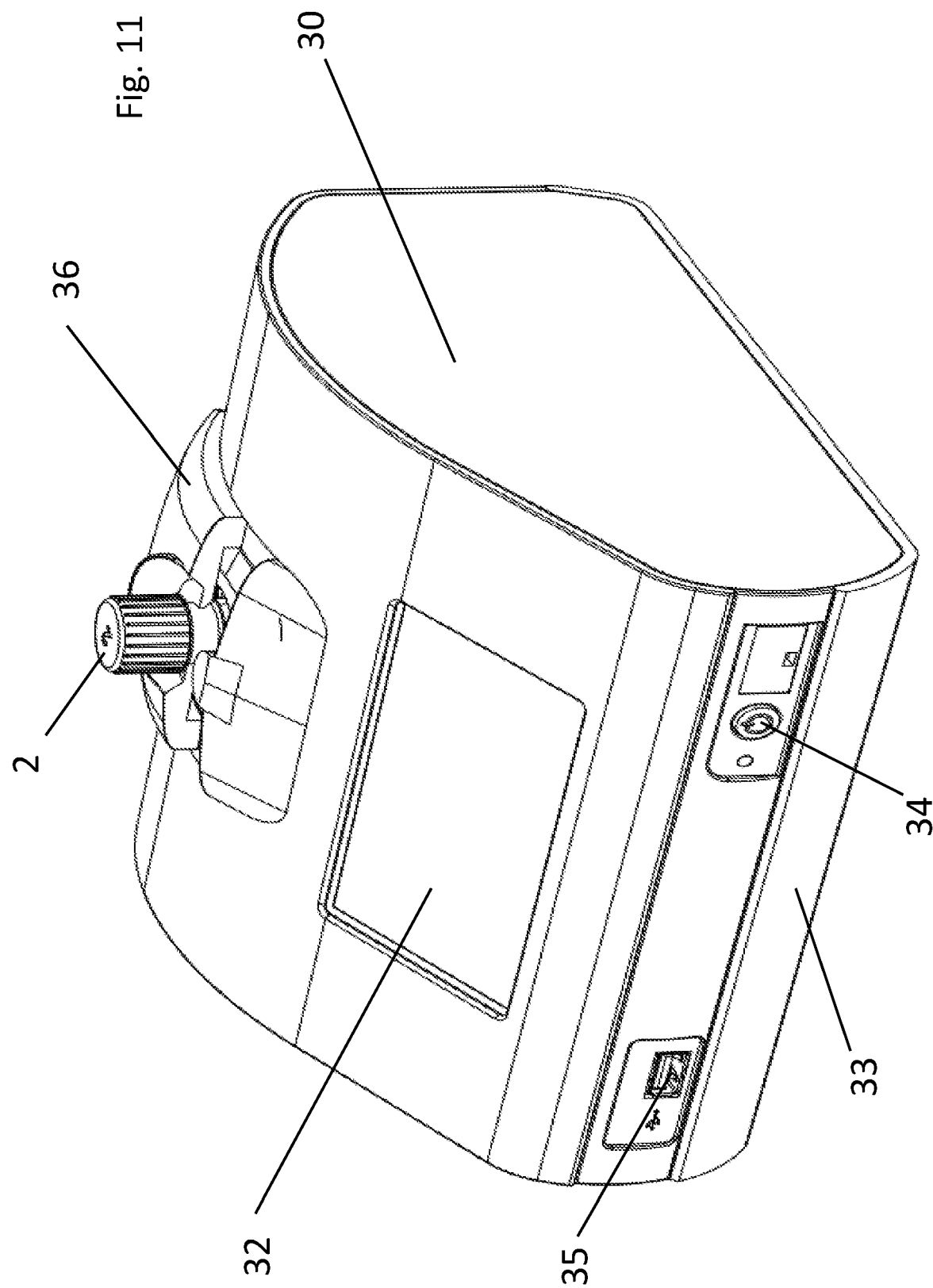
FIG. 11 shows a diagnostic test system with the cartridge in place, aligned and supported in a diagnostic test instrument.

FIG. 11 shows the cartridge in place within the instrument body 30, and locked in place by a spring-loaded sliding cover 36 that slides over and around a retaining collar 13 of the cartridge.

In this configuration, the shipping cap 2 is exposed and available to the user, and is removed to start the test.

The cartridge is retained and heated within the instrument during the following test functions, but only the cartridge is shown in FIGS. 3 through 9 to assist in illustrating and explaining the cartridge functions.

Figure 3:
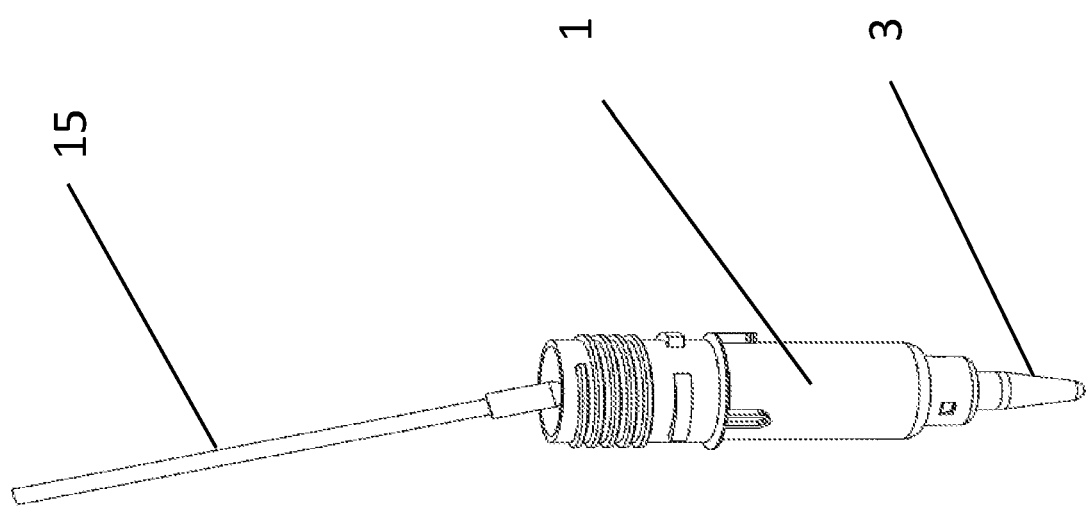
FIG. 3 shows the cartridge with the shipping cap removed, and a swab being inserted into the open volume of a sample preparation reservoir of the cartridge to deposit sample material therein.

FIG. 3 shows the cartridge with the shipping cap 2 removed prior to the start of a test. The user is prompted by software functions and the user display on the instrument to remove the cap 2 and add the sample to be tested. This prompt can follow a stage of heating of the sample chamber 1 to raise the temperature of the sample preparation fluid 11 prior to addition of the sample.

The sample can be one of many types, and may be included into the sample preparation fluid 11, by any suitable methods, including but not limited to pipette addition or droplet addition of a fluid sample, addition of a small tissue sample or a body fluid or environmental, veterinary, food or agricultural sample. As the test uses nucleic acid amplification, it can be very sensitive, and only a small amount of sample material it is required to be effective in testing.

FIG. 3 shows a sample collection swab 15 being introduced into the open cartridge. In the case of a sample collection swab 15 being used, it is introduced into the sample chamber 1 by a user and washed in the sample preparation fluid 11. The sample preparation fluid 11 is configured to wash the sample material from the swab 15, and may contain salts, dilution fluid or detergents that separate cells and cause the lysis of cell walls to expose nucleic acid components of the sample material, including DNA or RNA target material, into the sample chamber solution so that it will be suitable for subsequent nucleic acid amplification.

Other sample collection methods or sample types can be applied to the test cartridge as alternatives to a swab 15.

These sample collection and sample addition methods may include but are not limited to:
(i) use of pipette and add a sample fluid;
(ii) use of a whole blood droplet directly from a finger prick; and
(iii) use of an absorbent pad or membrane to collect a fluid sample such as whole blood and add it to the sample conditioning wash fluid 11.

Following addition of the sample, the instrument display, under control of the instrument software, prompts the user to wait for a period of time to allow the sample preparation and cell lysis process to have sufficient time to be effective.

Once the sample preparation time period has completed, the user is prompted to insert the dispensing cap assembly. This dispensing cap assembly is shown in FIG. 4 as consisting of a cap 20 attached to a sample dispensing mechanism, the latter including a dispense rod 21 and a dispense insert 22.

In the described embodiment, the dispensing cap assembly is supplied fully assembled in a protective packet, and is removed and inserted by the user, but this need not be the case in other embodiments. For example, in some embodiments the sample dispensing mechanism can be attached to the removed transport cap 2 by the user in order to form the cap assembly, and in some other embodiments the dispensing mechanism can be disposed within the sample preparation reservoir, and a cap (either the removed transport cap 2 or a different cap) coupled to the dispensing mechanism by the act of applying the cap to the sample preparation reservoir 1.

In any case, the sample dispensing mechanism is operable to rupture or otherwise disrupt or open the at least one seal to allow sample fluid to enter the at least one diagnostic test reservoir 3 from the sample preparation reservoir 1, and to dispense a predetermined sub-volume of the sample fluid from the sample preparation reservoir into the at least one diagnostic test reservoir 3 for diagnostic testing and detection therein while preventing further fluid movement between the sample preparation reservoir 1 and the at least one diagnostic test reservoir 3.

Figure 4:
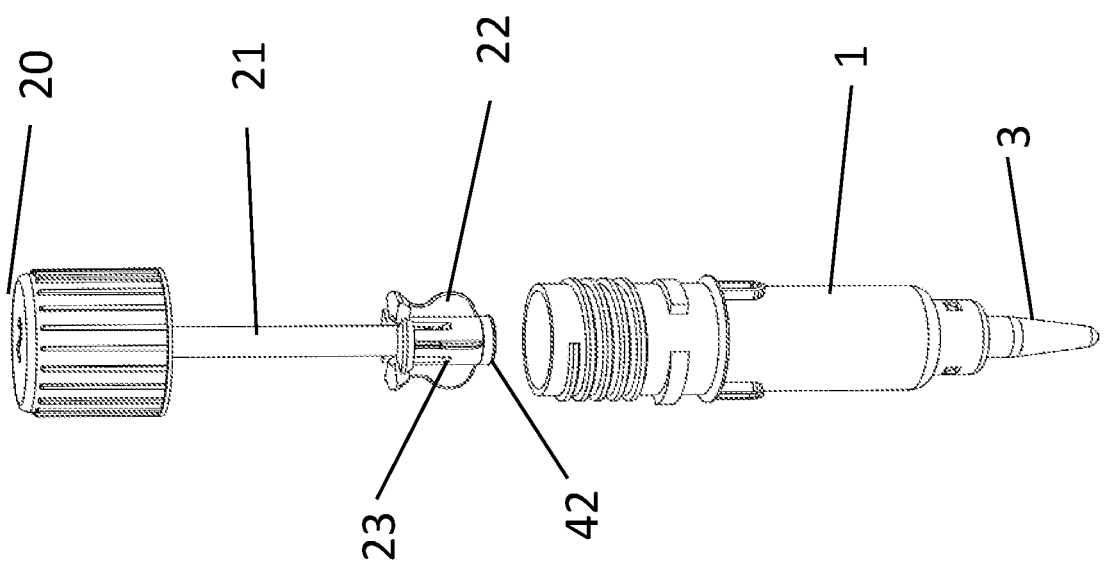
FIG. 4 shows a dispensing cap assembly including a cap and a dispensing mechanism about to be inserted into the sample preparation reservoir.

In the described embodiment, as shown in FIG. 4, the dispense insert 22 is mounted to one end of the dispense rod 21. The dispense rod 21 incorporates a flange 42 that constitutes a plunger or piston once it is inserted into a cylindrical bore or 'cylinder' of the dispense insert 22. In some embodiments, the piston forms a sliding seal by close fit with the cylindrical bore, but in other embodiments incorporates an elastomer seal to improve the seal. In the embodiment shown in FIG. 5, an "O" ring 24 is used to improve the seal for the piston as it slides within the cylindrical bore of the dispense insert 22.

As shown in FIG. 4, the dispense insert 22 incorporates openings in the form of slots 23 in its upper section. These slots 23 are arranged such that, in the initial configuration of the dispense rod piston as the assembly is inserted into the cartridge, the internal o-ring is positioned above the base of the slots 23, and the slots 23 extend out to the outer diameter of the insert 22 such that fluid can flow both past the outside of the cylindrical bore of the insert 22 and also through its cylindrical bore as the insert 22 is pressed further into the sample preparation reservoir. This configuration prevents pressure build up, and assists mixing of the sample fluid during insertion. Other suitable forms of the openings and configurations will be apparent to those skilled in the art, such as holes or grooves, for example, to achieve this function, where the insert 22 does not form a seal with the internal wall of the sample preparation reservoir, and thus it can easily be moved through the sample fluid retained within the sample preparation reservoir 1. The outer diameter and form of the dispense insert 22 allows it to be positioned and aligned centrally within the sample preparation reservoir 1 as it is pressed in, also to easily move down into the sample preparation reservoir as it is inserted (i.e., without significant resistance from the sample fluid). This allows the base of the dispense insert 22 to be accurately aligned with a mating recess 54 in the base of the sample preparation reservoir 1.

Figure 5:
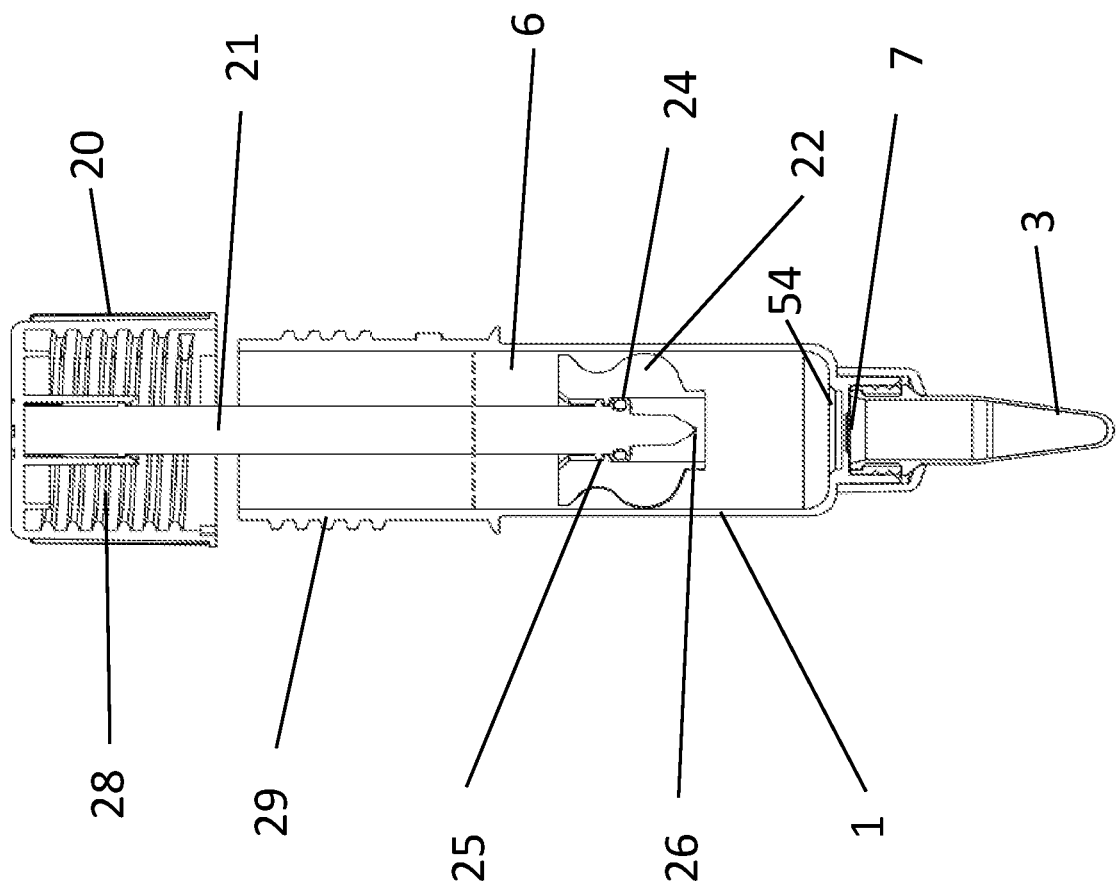
FIG. 5 is a cross-sectional side view of the cap assembly during insertion into the sample preparation reservoir.

FIG. 5 shows the dispensing mechanism part way inserted into the sample preparation reservoir 1. The dispense rod 21 includes a piston flange 42 with a sealing "O" ring 24 and also a seal perforation tip 26 at the end of the dispense rod 21.

Once the dispense assembly is sufficiently inserted, the internal threads 28 in the cap 20 engage with the external thread 29 on the body of the cartridge.

Once these threads 28, 29 have mutually engaged, the user is prompted to and can progressively screw the cap 20 closed. The action of screwing the cap 20 closed provides a mechanical advantage that facilitates the travel of the dispense assembly through the sample preparation reservoir 1 to engage the internal components, perforate the seals at the base of the sample preparation reservoir 1, and dispense a sub-sample volume of sample fluid from the sample preparation reservoir 1 into the diagnostic test reservoir 3.

Figure 6:
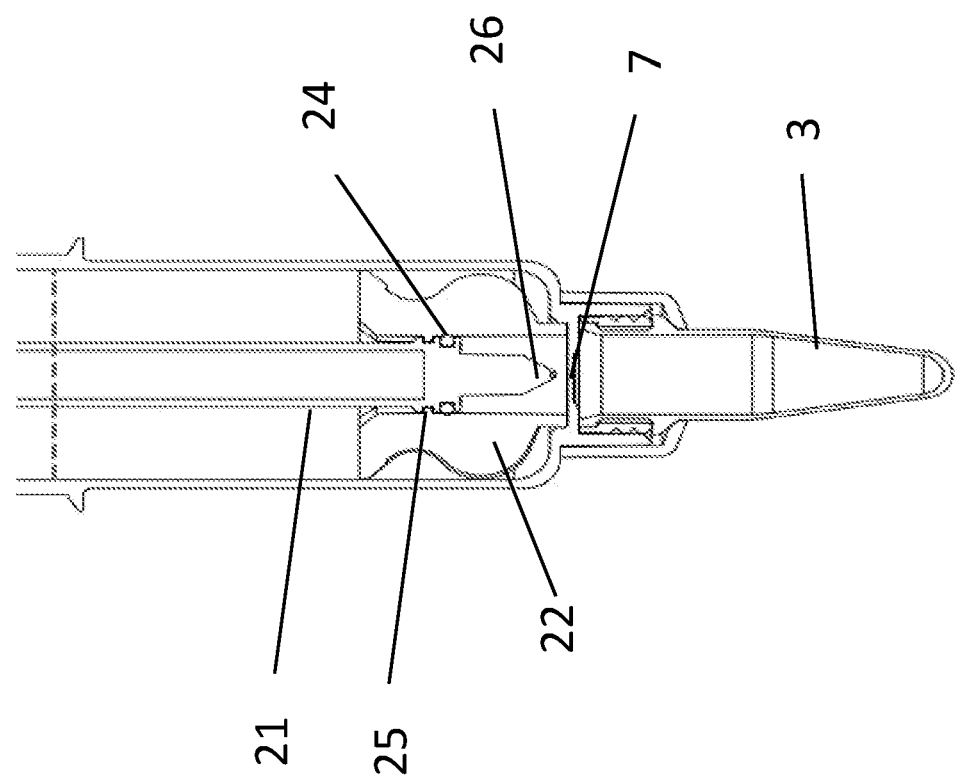
FIG. 6 is a cross-sectional side view showing a dispense insert of the dispensing mechanism after contacting an internal base of the sample preparation reservoir to form a seal therewith as a user applies a screwing action to the cap.

FIG. 6 shows the dispense insert 22 after it has made contact with the base of the cartridge body 1. In this position, the dispense insert 22 is retained on the dispense rod 21 in such a way that some additional force is required before the dispense rod 21 can move further into the bore of the dispense insert 22. This additional force allows the base of the dispense insert 22 to be pressed under friction or snapped into place into a mating or surface feature in the recess 52 at the base of the sample preparation reservoir 1, forming a fluid seal therewith. In some embodiments, a small elastomer seal is included either on the dispense insert or the sample tube to assist the formation of this seal. However, in the simplest embodiment, the injection moulded form of the base of the dispense insert 22 and the mating feature in the sample preparation reservoir are sufficient to form a fluid seal under the compression force applied as these parts come into mutual contact. FIG. 6 shows a detent formed by a circular groove 25 in the dispense rod 21 and a corresponding annular ring on the dispense insert 22. This detent provides the initial break-away force to lock and seal the dispense insert into place in the base of the sample preparation reservoir prior to the completion of the dispense operation once the detent resistance is overcome and the dispense rod 21 starts to travel through the dispense insert 22 under the continued rotational action of the screw cap 20. Other arrangements for providing the dispense insert sealing force are available, and will be apparent to those skilled in the art in light of this disclosure.

Figure 7:
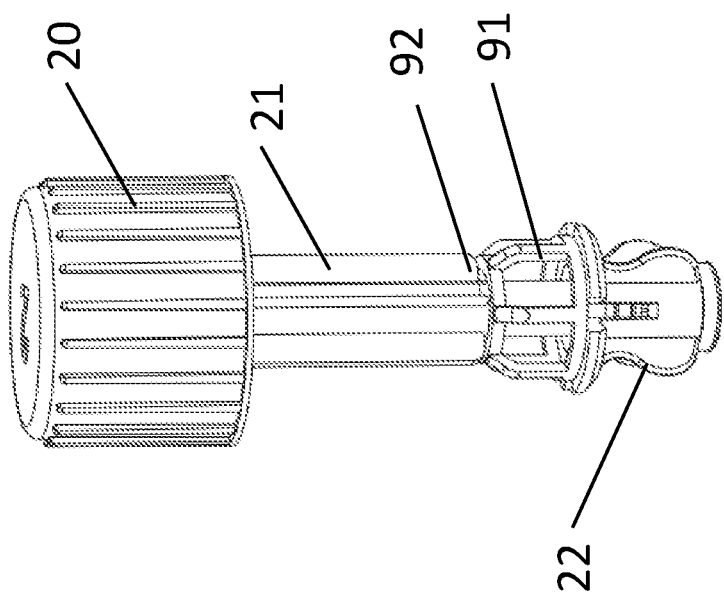
FIG. 7 shows an alternate form of dispensing cap assembly wherein a dispensing mechanism includes a collapsible spacer to provide force sequencing and ensure that the dispense insert forms a seal with the internal base of the sample preparation reservoir.
Figure 8:
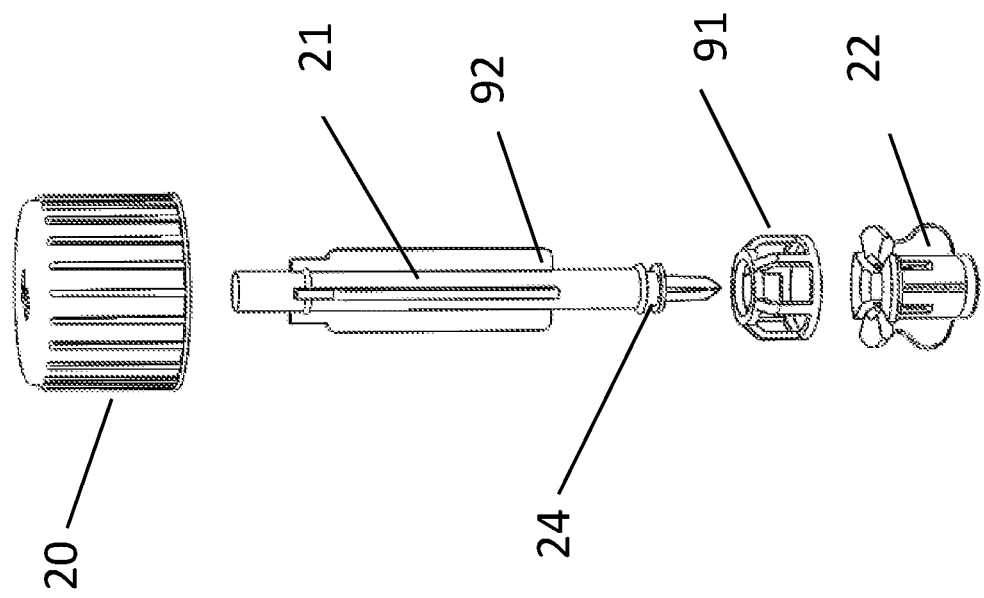
FIG. 8 is an exploded view of the dispensing cap assembly of FIG. 7.
Figure 9:
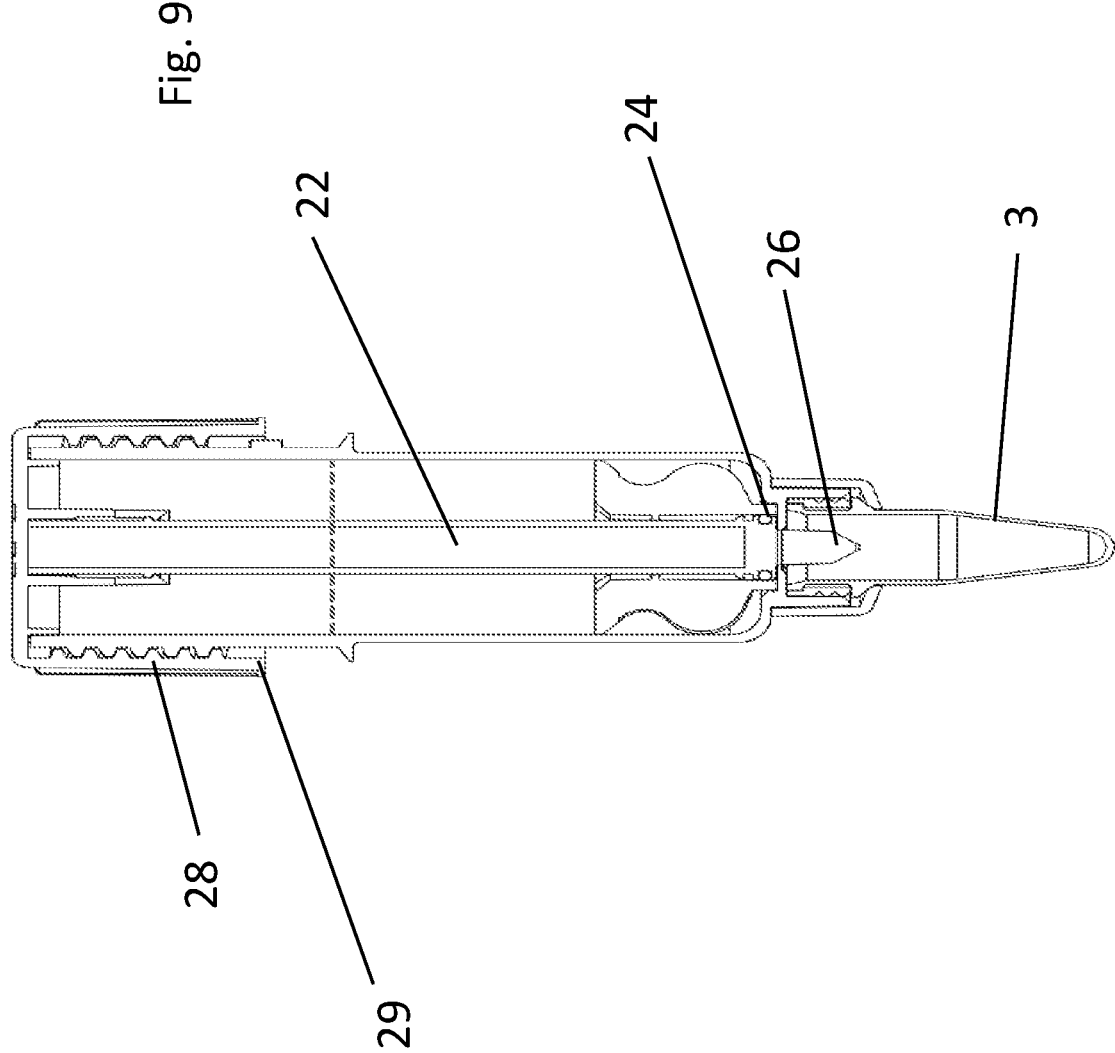
FIG. 9 is a cross-sectional side view showing a dispense rod of the dispensing mechanism after the screw cap has been fully engaged by the user, causing perforation of seals between the sample preparation reservoir and a diagnostic test reservoir of the cartridge and dispensing of sample fluid from the sample preparation reservoir into the diagnostic test reservoir.
Figure 10:
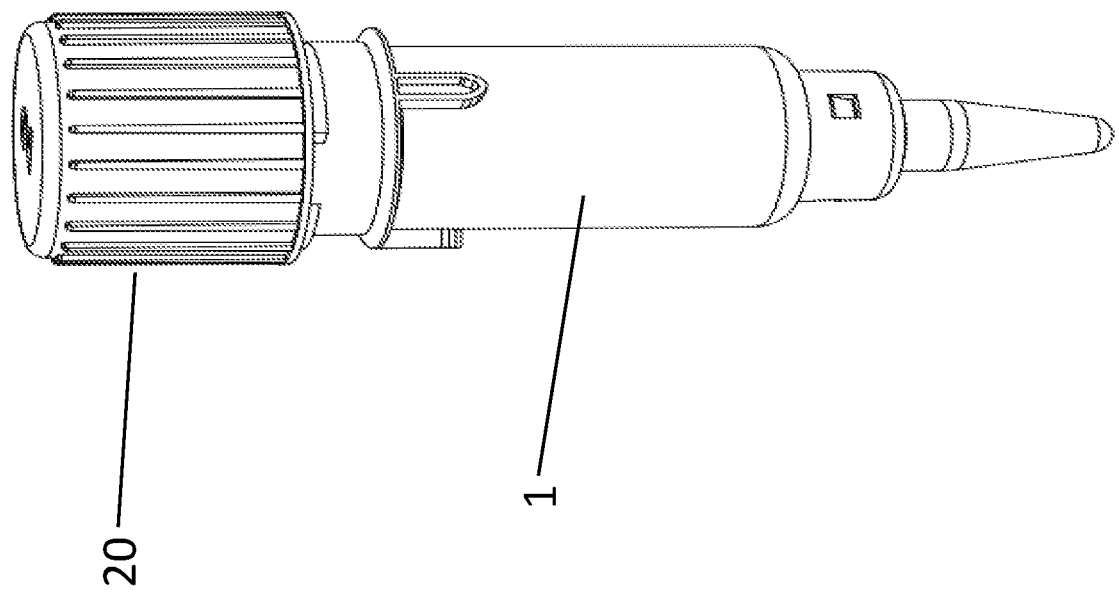
FIG. 10 is an external view of the cartridge after fully engaging the cap assembly as per FIG. 9.

FIG. 7 shows an alternative construction of the dispenser cap and the dispense mechanism. In this embodiment, insert 22 is fitted onto the dispense rod 21 with a collapsible or crushable spacer component 91 captured between both the dispense insert and an engagement feature 92 extending from the dispense rod. FIG. 8 shows this same dispensing cap assembly in an exploded parts view.

As the dispensing cap assembly is pressed into the cartridge by the screw cap action, the dispense insert makes contact with the base of the cartridge sample chamber. The collapsible spacer 91 allows the screw action to apply a force to engage the sealing action wherein the base of the cylindrical bore of the dispense insert is pressed into the mating feature in the base of the cartridge.

As the cap screw action applies additional force and travel, the spacer 91 is configured to collapse in a controlled manner to press the dispense insert into place and then allow the "0" ring plunger on the dispense rod 21 to enter the tubular bore section of the dispense mechanism.

In the arrangements above, after the dispense insert is held or locked in place, the "0" ring plunger on the dispense rod 21 is caused to enter the tubular section of the dispense mechanism and form a piston and cylinder or syringe.

As the "0" ring plunger traps a fluid volume into the dispense tube, the piercing tip 26 of the dispensing rod 21 perforates the plastic section in the cartridge at the base of the tube in the dispense insert 22. This perforation action punches a hole through the plastic section and also through the foil or plastic membrane over the top of the amplification tube 3. Continued travel of the plunger then dispenses the trapped fluid volume into the amplification tube 3.

The fluid trapped in this cylindrical section is a fixed and predetermined volume of the sample fluid that is dispensed through the perforation in the base of the sample chamber into the amplification tube 3 mounted below.

The dispense action forces the fixed volume of sample fluid into the amplification tube and the tube contents are pressurised by the addition of the dispensed fluid. This modest pressurisation of the amplification tube 3 is suitable for most test applications, and does not interfere with typical chemical, immunoassay tests or with PCR or isothermal amplification. However, as an alternative to pressurisation of the amplification tube 3, in some embodiments the dispense rod 21 shown in FIG. 6 is hollow and includes a vent 27 (not shown) from the perforation tip 26 to an internal channel 22 within the dispense rod 21. The internal channel 22 of the dispense rod 21 is in communication with the air at the top of the sample fluid chamber 1. This vent equalises the pressure between the air volume at the top of the amplification tube 3 with the air pressure above the sample fluid in the sample preparation reservoir 1. This venting arrangement is advantageous in some applications because it reduces the risk that tube amplicons may leak into the environment assisted by internal pressure.

Multiple Tube Cartridge Embodiment

Amplification tests within a single amplification tube 3 can be multiplexed in that more than one DNA or RNA target sequence and a control channel can be detected within a single amplification tube 3. Where the system uses fluorescence as the detection method, the different targets can be detected with probes that emit at different florescence wavelengths, referred to in the art as detection channels. In the instrument described herein, two channels of detection are included. Using the single tube cartridge described above and a two channel detection instrument described herein, the system can provide detection of two different DNA or RNA targets. If additional targets are required to be multiplexed into the single diagnostic test from the same sample, additional amplification tubes can be provided in other embodiments. In this way, additional targets and control channels can be included while using the same number of detection sensors in the instrument. For example, in the case of an embodiment with two instrument sensor channels and two amplification tubes, the system is capable of 4 independent channels of DNA or RNA detection from a single sample that is prepared and dispensed from the cartridge body into the two amplification tubes.

Figure 18:
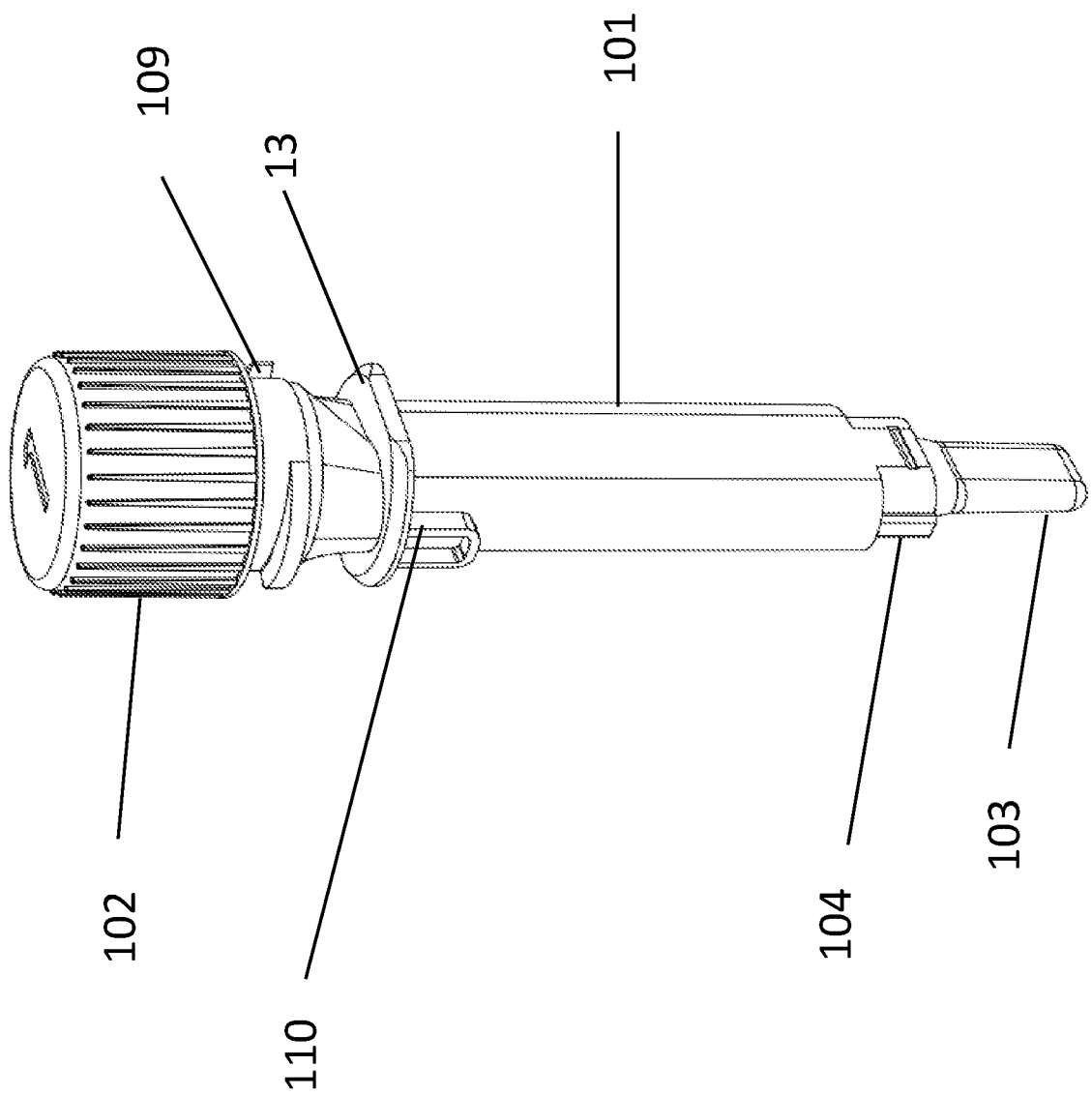
FIG. 18 shows an embodiment of a cartridge having two diagnostic test reservoirs.

FIG. 18 shows a two tube cartridge assembly in accordance with an embodiment of the present invention. The amplification tubes can be separate tubes connected to the body of the cartridge; however, in the example shown in FIG. 18, a moulded plastic tube component 103 incorporates two internal cavities that are equivalent to two independent amplification tubes connected to the cartridge body 101.

FIG. 18 shows the cartridge in its shipping configuration prior to start of test, where the shipping cap 102 does not contact the moulded latch features 109 and the cap 102 can be removed by the user at the start of a test.

Figure 19:
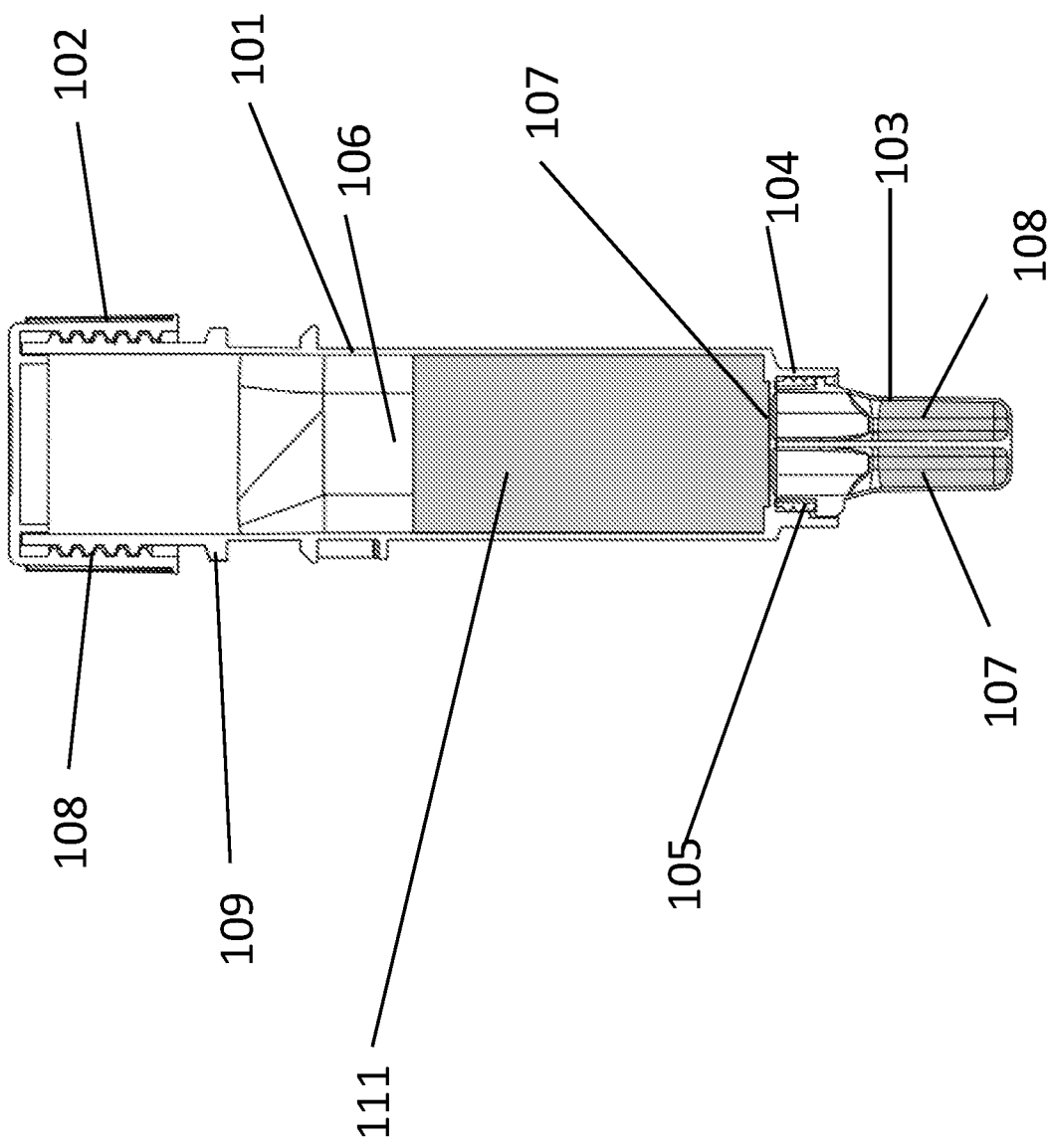
FIG. 19 is a cross-sectional side view of the dual test reservoir cartridge of FIG. 18.

FIG. 19 shows the same cartridge in cross section, where the tube component 103 incorporates two internal amplification tubes 107 and 108. These tubes carry the required precursor reagents for the DNA or RNA amplification and detection probes, typically in dried or lyophilised form. The reagents incorporated within each tube 107, 108 may be different for conducting different tests from the same sample, or may be identical reagents to provide a replicated, addition test confirmation. The tube component 103 is clipped into place within a mating recess feature 104 in the base of the cartridge body 101. An elastomer seal 105 is trapped between the base of the moulded cartridge body and the tube assembly and forms a seal to prevent leakage between the amplification tubes 107, 108 and the environment.

The cartridge body contains a sample preparation reagent 111, typically in a liquid form, and typically added during manufacture. It is an option to supply the sample reagent 111 in separate containers of one or more parts, and add these to the cartridge prior to the test when the cap is removed. The cartridge operates in a similar manner to that described above for the single amplification tube embodiment, where the sample preparation liquid 111 forms an aqueous solution to expose and carry the DNA or RNA from the sample once it is added, and to resuspend or dissolve the amplification reagents in the tubes 107, 108 at the base of the cartridge once a sub-volume of the sample dilution fluid is added by the dispense action into these tubes 107, 108.

To conduct a test, the cartridge is inserted into the instrument port to support and start heating the sample reagent fluids 111. This heating can assist, speed up or enable the sample preparation process, including cell lysis. The cartridge is supported and operated within the instrument, but for the purposes of illustration, the instrument components are not shown in the drawings of the cartridge shown in FIGS. 18, 19, 20, 21, 22, 23, 24, 25 and 26.

Figure 27:
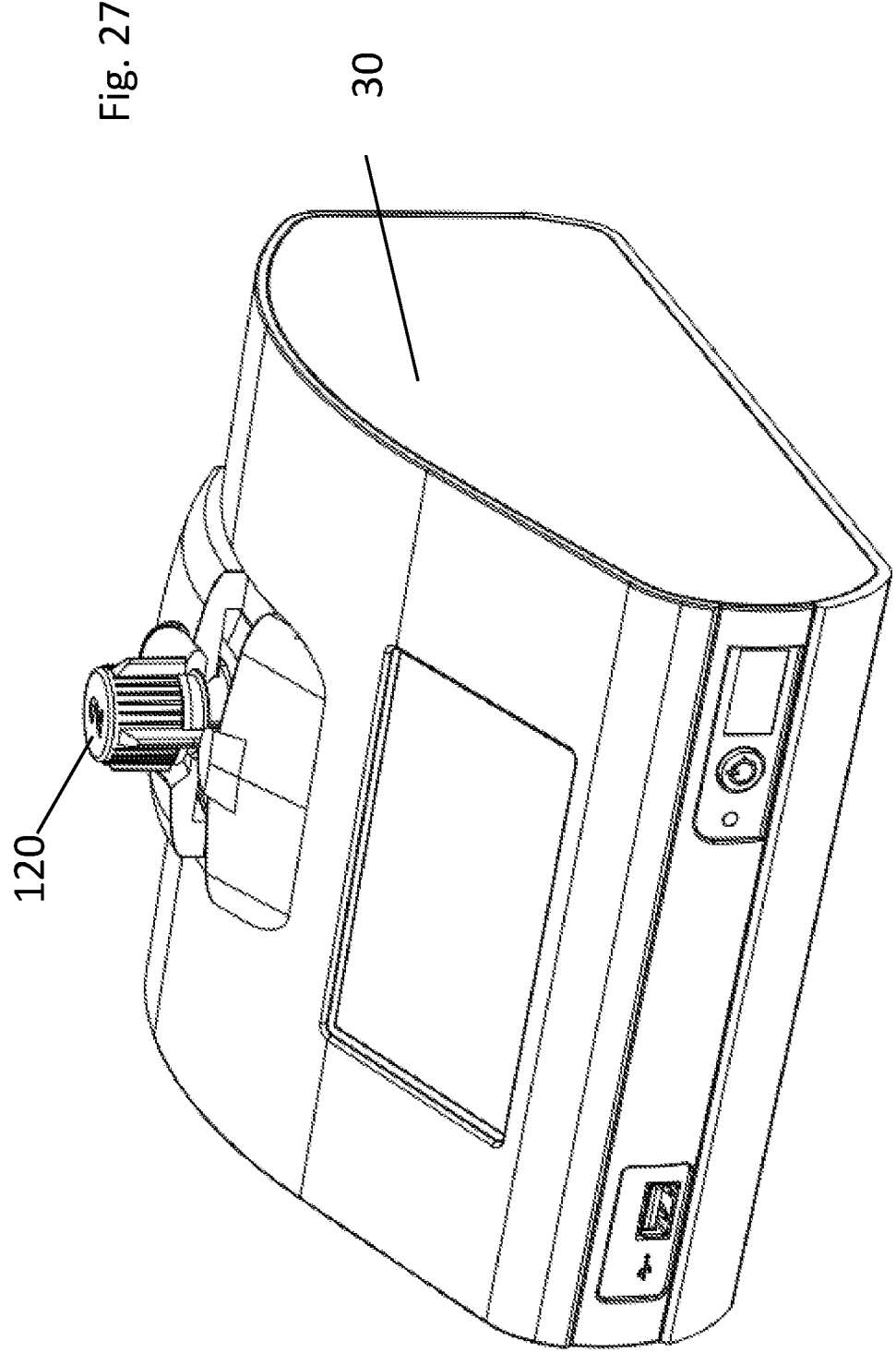
FIG. 27 is a drawing of an embodiment of the instrument configured for operation with the dual test reservoir cartridge and with the dual test reservoir cartridge in place therein.

FIG. 27 shows the cartridge fully inserted into the instrument with dispensing cap 120 available for the user to operate the cartridge by removal of the shipping cap, addition of the sample, application and screw closure of the dispensing cap 120.

Figure 20:
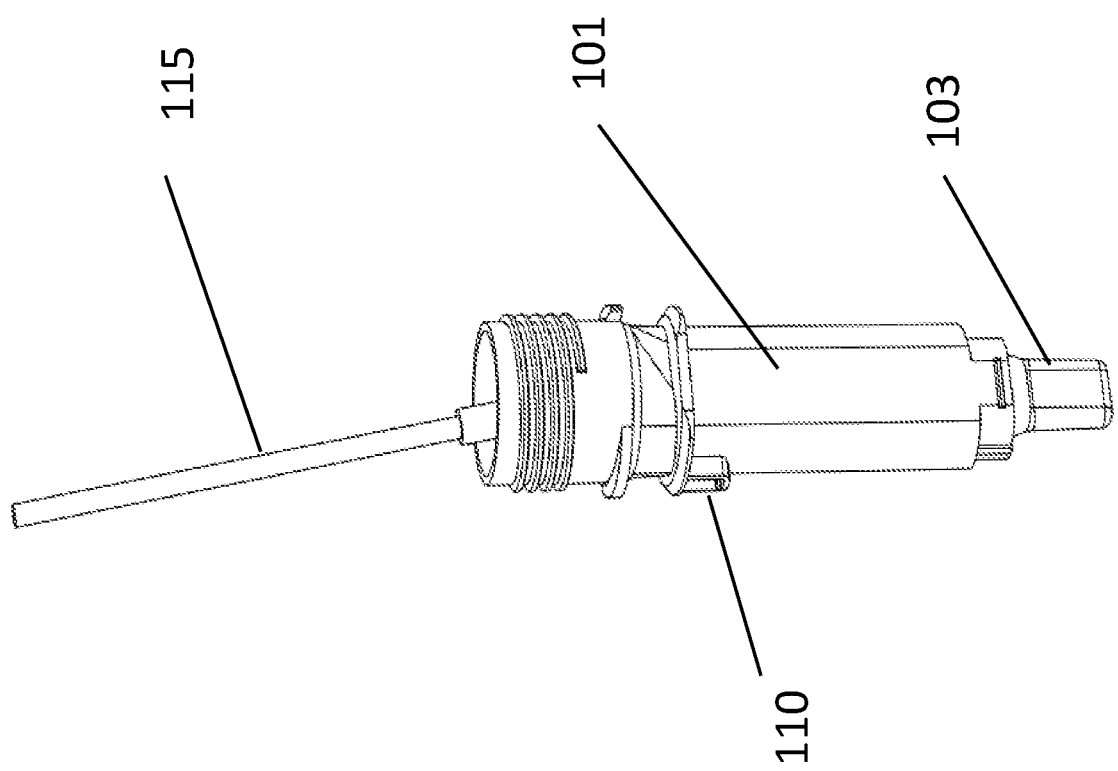
FIG. 20 shows the cartridge of FIGS. 18 and 19 with its shipping cap removed, and a swab being inserted into the open volume of a sample preparation reservoir of the dual test reservoir cartridge to deposit sample material therein.

FIG. 20 shows the two tube cartridge at the start of test with the cap removed and with a swab 115, being used to add sample material by washing the swab 115, in the sample reagent fluid 111 contained within the cartridge body 101.

Figure 21:
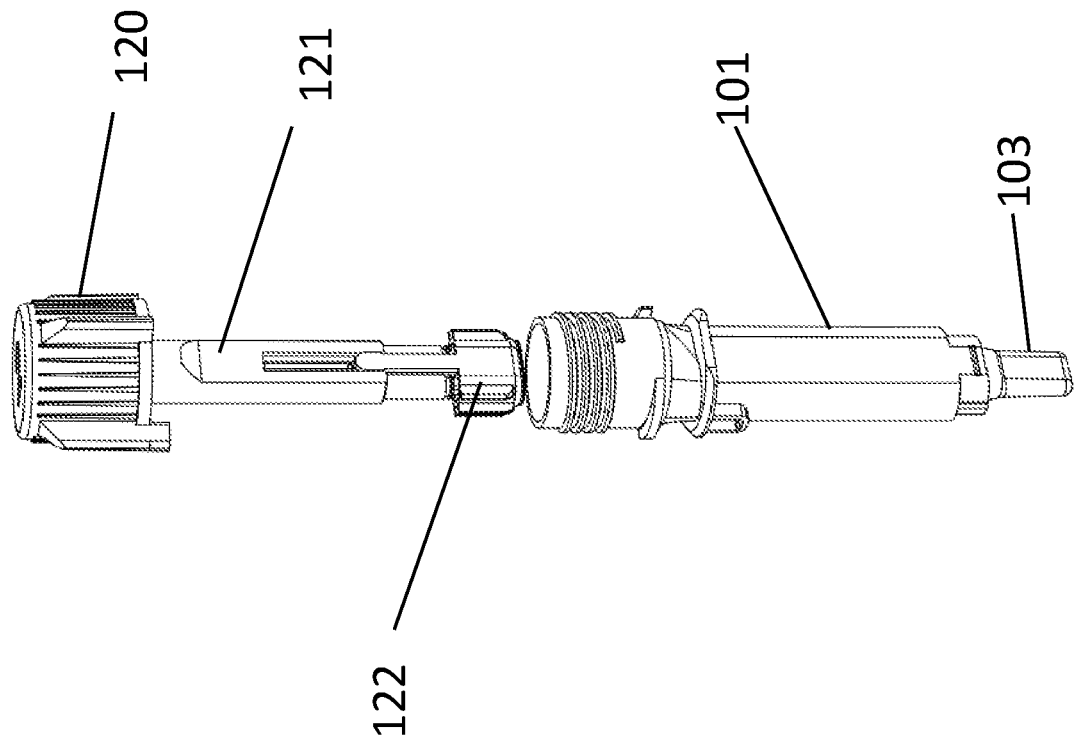
FIG. 21 shows a cap assembly including a cap and an embodiment of a dual test reservoir dispensing mechanism about to be inserted into the sample preparation reservoir of the dual test reservoir cartridge.

FIG. 21 shows the cap 120 and the dispense mechanism in position to be inserted by the user into the cartridge body 101. The assembly in this view is made up of the following visible components: the dispense cap 120, the dispense rod 121 and the dispense insert 122.

Figure 22:
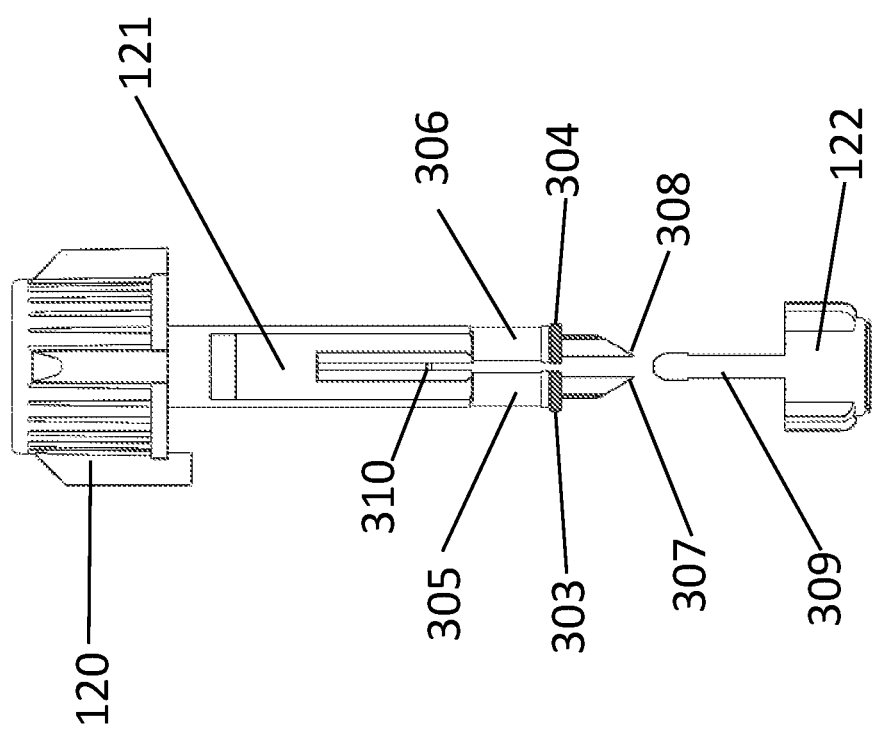
FIG. 22 shows the dual test reservoir dispensing mechanism with its dispense insert separated from its dispense rod.

FIG. 22 shows the dispense assembly in a disassembled view. At its top section, the two-tube cartridge is circular in cross section to allow the screw cap to fit; however in its lower section, the cartridge has flattened sides. The dispense insert 122 is a loose fit in the upper circular cross section of the cartridge, but is a close slide fit in the flattened cross section portion of the cartridge. This close slide fit is used to guide the dispense insert 122 into place such that it aligns with the mating feature at the base of the cartridge, and the two cylindrical bores align with the perforation points that allow the sample fluid to exit the cartridge body 101 into the two amplification tubes 103. The circular to flattened cross section transition is gradual with a twist in its form such that it naturally rotates and guides the dispense insert 122 into alignment as the dispense assembly is inserted. This circular to flattened transition in the form of the cartridge body 101 is shown in FIG. 18 in the body section between the lid location feature 13 and the cap locking feature 109.

The dispense assembly is shown in an exploded assembly view in FIG. 22. The dispense rod 121 is clipped into the cap 120 so that it can freely rotate to assist alignment of the dispense assembly 122 with its entry into the flattened cross section of the cartridge as the assembly is inserted. The dispense rod 121 has two projections 305 and 306. For each of these projections 305, 306, its lower section forms a corresponding piston with a corresponding O-ring seal 303, 304, and below each piston forms a corresponding sharp point 307, 308.

The points 307, 308 may be shaped in cross section to assist fluid flow past the points 307, 308 during perforation. For example, in the described embodiments, the points are V-shaped in cross section to allow each of the points 307, 308 to fold out a small triangular chad as they perforate the thin material section at the base of the cartridge to assist the flow of dispensed liquid past the points 307, 308.

When the dispense insert 122 is assembled onto the dispense rod 121, the perforating tips 307, 308 of the dispense rod projections 305, 306 project into the cylindrical bores of the dispense insert 122 but do not fill its volume. These bores are shown in cross section in FIG. 23. The dispense insert section has a slide 309, as shown in FIGS. 21 and 22, that fits closely and slides onto and between the projections 305, 306 of the dispense rod 121. When fitted, the dispense insert 122 slides up to contact with the small bridge 310 on the dispense rod. The contact with the small bridge 310 prevents further travel in normal handling prior to use, and the slide fit of the insert 122 onto the rod 121 retains and aligns the dispense insert 122 in a controlled manner and is a firm fit such that it will not come off with normal handling.

Figure 23:
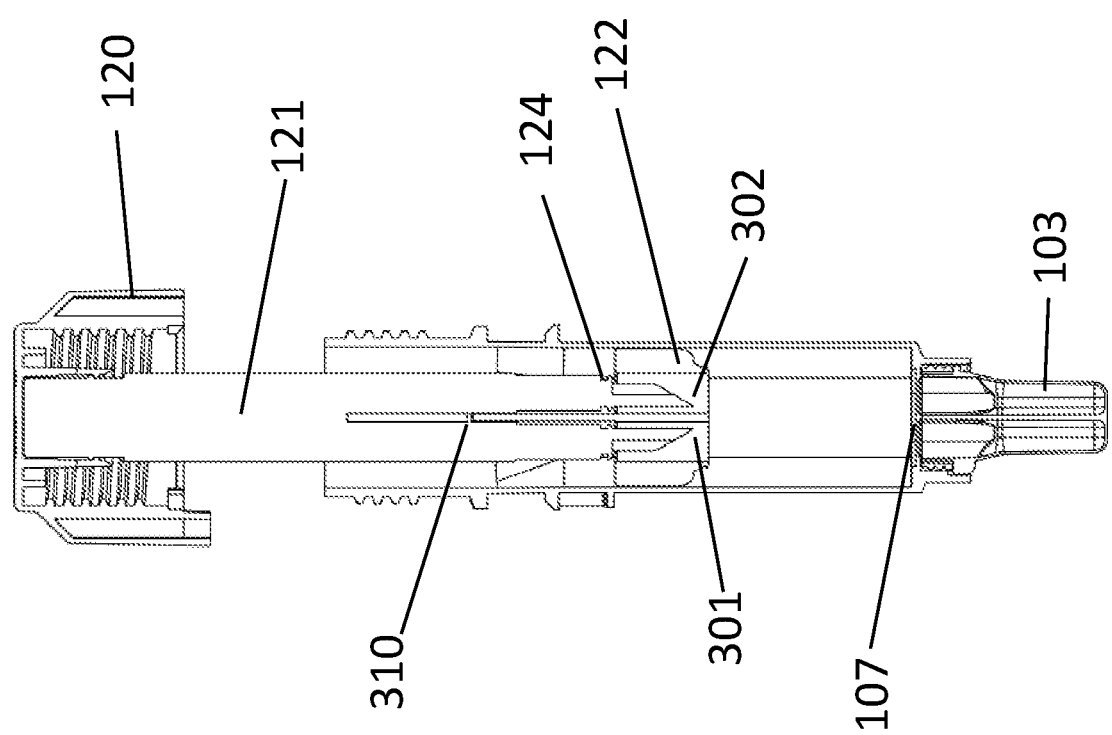
FIGS. 23 to 25 are cross-sectional side views of the dual test reservoir cartridge with its dispense mechanism respectively: (i) partially inserted, (ii) further inserted so that its dispense insert has seated against the base of the cartridge but prior to perforation and dispensing, and (iii) fully inserted so that the perforation and dispense actions have completed.

FIG. 23 shows in cross section the two-tube dispense insert 122 partially pressed into the cartridge assembly. The dispense insert 122 is a slide fit onto the rod 121 and is blocked from further travel by the small bridge 310. The dispense insert 122 incorporates the two open ended cylindrical bores 301, 302.

Figure 24:
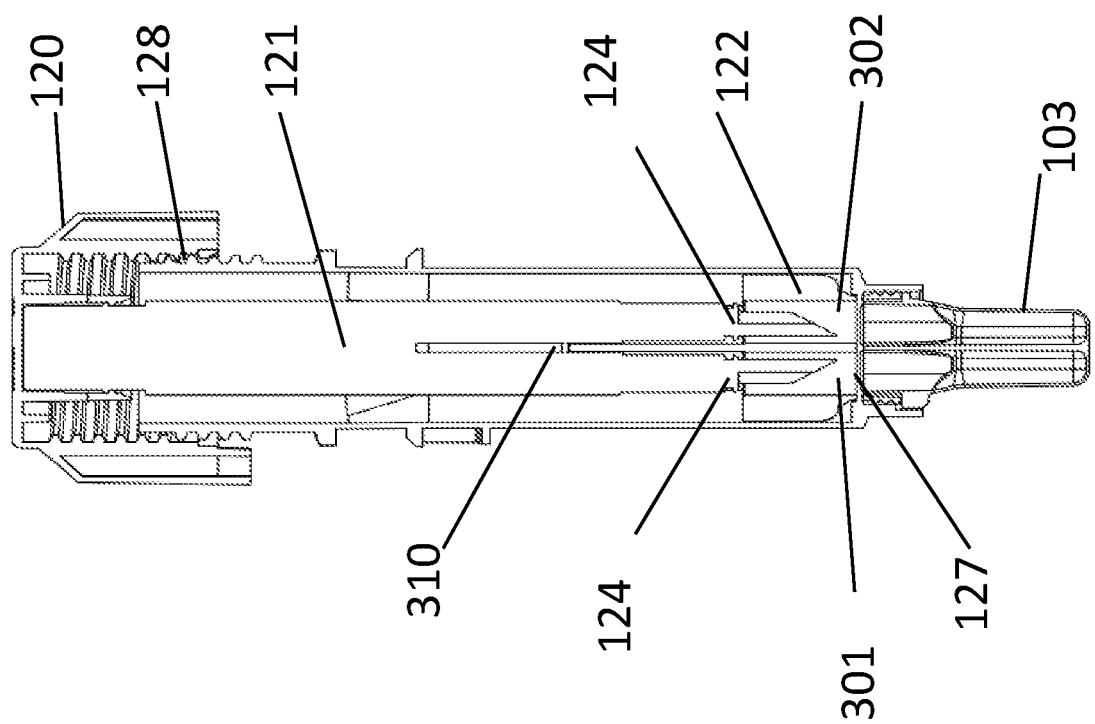

FIG. 24 shows in cross section the internal threads of the screw cap 120 engaged with the threads on the cartridge body and the dispense mechanism has progressed into the cartridge to the point where the base of the dispense insert 122 is just making contact with the thin material section at the base of the cartridge body 127. The base of the dispense insert 122 has features that mate and form a press fit with the base of the cartridge body, forming a fluid seal around the base of each of the cylindrical bores 301, 302. The bridge 310 on the dispense rod 121 has allowed the rod to apply sufficient force on the dispense insert to seat it firmly into the sealing feature at the base of the cartridge body. Once this part is seated, further progression of the cap threads caused by continued rotation of the cap 120 by the user, breaks away the small plastic bridge 310 to allow the dispense projections 305, 306 to progress further into the dispense insert 122.

At this point, the perforation points 307, 308 start to perforate the thin material section at the base of the cartridge body, and the piston or syringe features 303, 304 with "O"-ring seals progress to seal the tops of the two cylindrical bores 301, 302.

With further travel, as the screw cap 120 is further closed by the user, the projection 310 deflects or breaks away to allow the O-rings 303 and 304 on the projections 305 and 306 to seal the tops of the dispense barrels, forming closed volumes of fluid within the respective dispense bores 301, 302. As the user completes the cap closing action, the O-ring sealed pistons are forced by the action of the engaged threaded cap 120 and the dispense insert 122 being pressed into the cartridge body 101 to travel the full distance through the two dispensing insert bores 301, 302 to dispense the trapped sample fluid into each of the two amplification or test reservoirs 103.

In this embodiment, the cartridge body 101 will typically have around 1 to 3 millilitres of sample and sample dilution fluid 111 present, and the dispense action will dispense a small amount of this fluid, in the order of around 50 to 100 microliters, into each of the amplification tubes 103. Without change to the form of this embodiment, the scale of the parts used can be varied to vary the both the sample dilution volume and the volumes dispensed into each of the amplification tubes 103.

Figure 25:
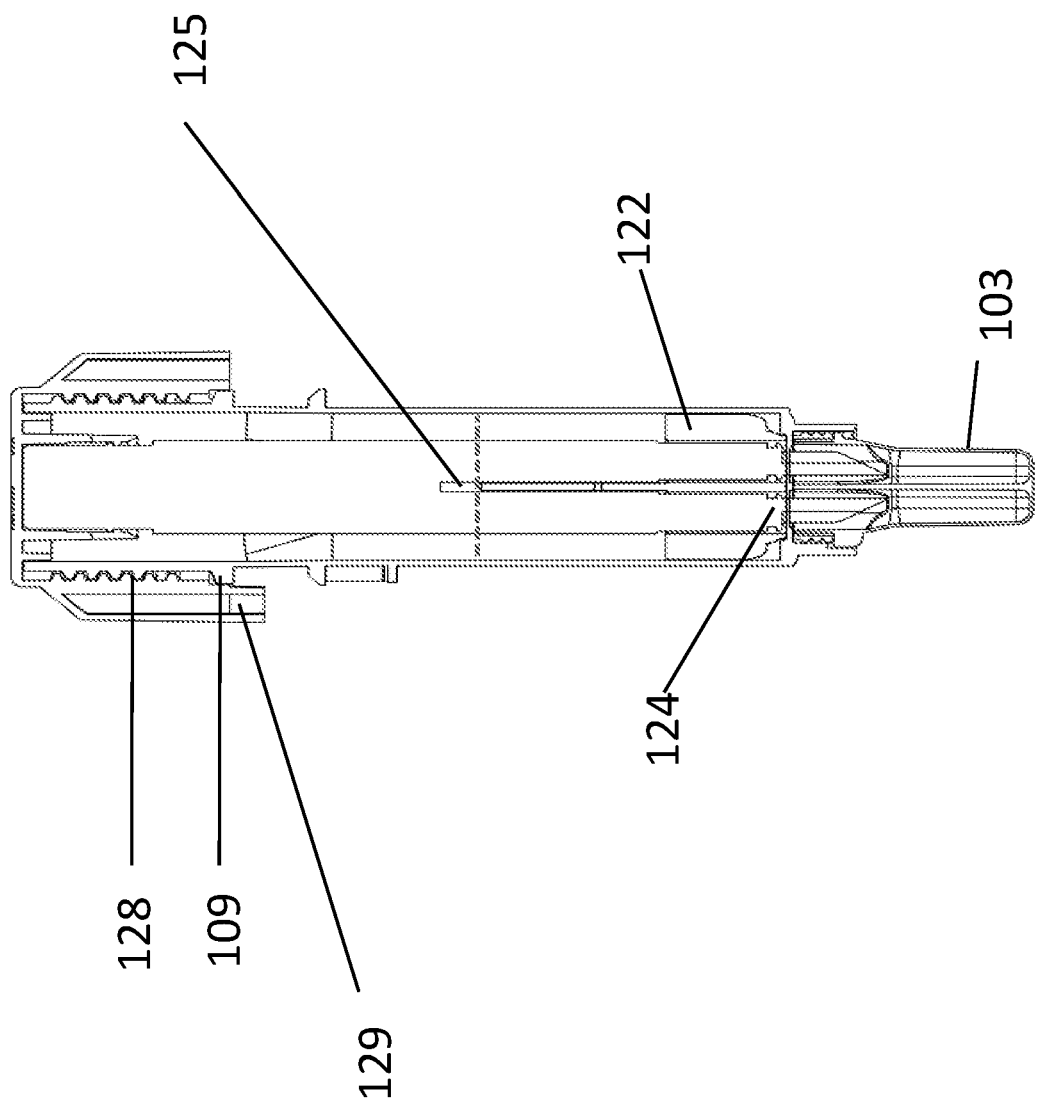

FIG. 25 shows the cartridge in cross section view, in the fully dispensed configuration. The dispense cap 120 is longer than the shipping cap, and its lower edge has alignment or anti-rotation features 129 that have latched over the moulded cam features 109 on the cartridge body 101. This prevents the cap 120 from being easily removed, and ensures that the test sample is fully sealed within the cartridge after it has been added and the dispense cap is fitted. This locking function has significant advantages for operator safety and test reliability, and protects against contamination of users and the test system during use and in subsequent removal, handling and disposal of the used cartridge assembly.

Figure 26:
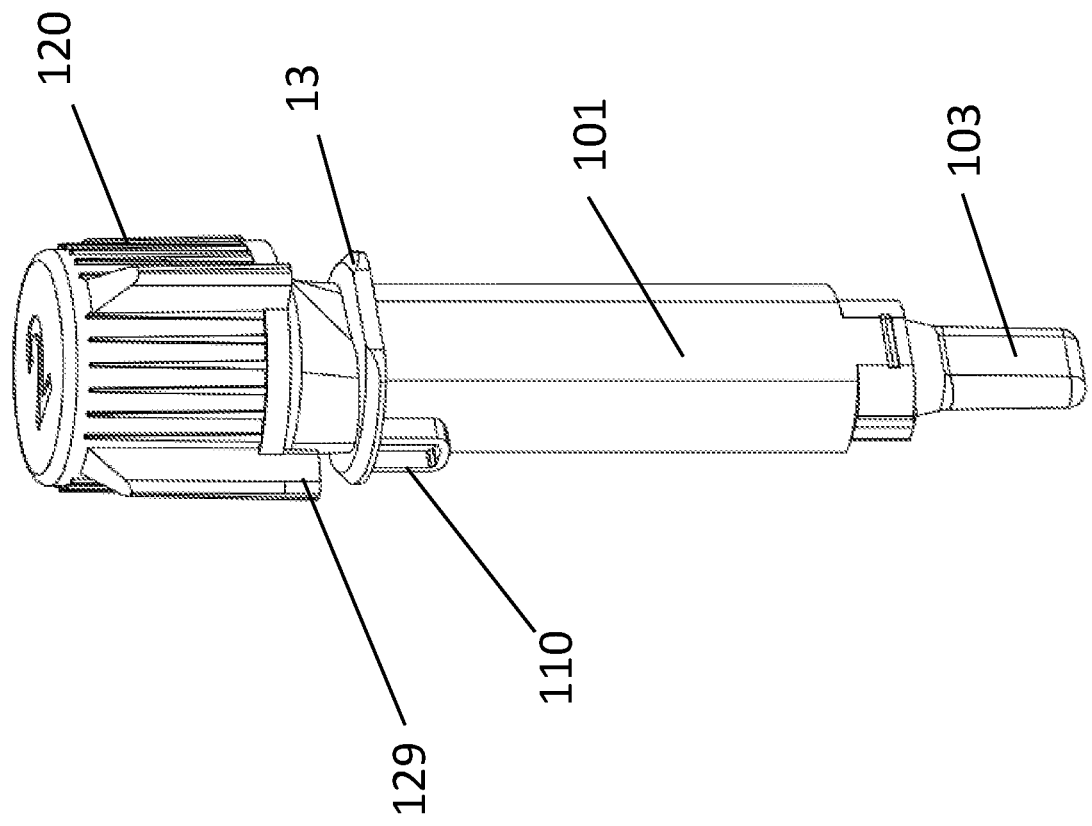
FIG. 26 is an external view of the dual test reservoir cartridge after fully engaging its cap assembly as per FIG. 25.
Figure 28:
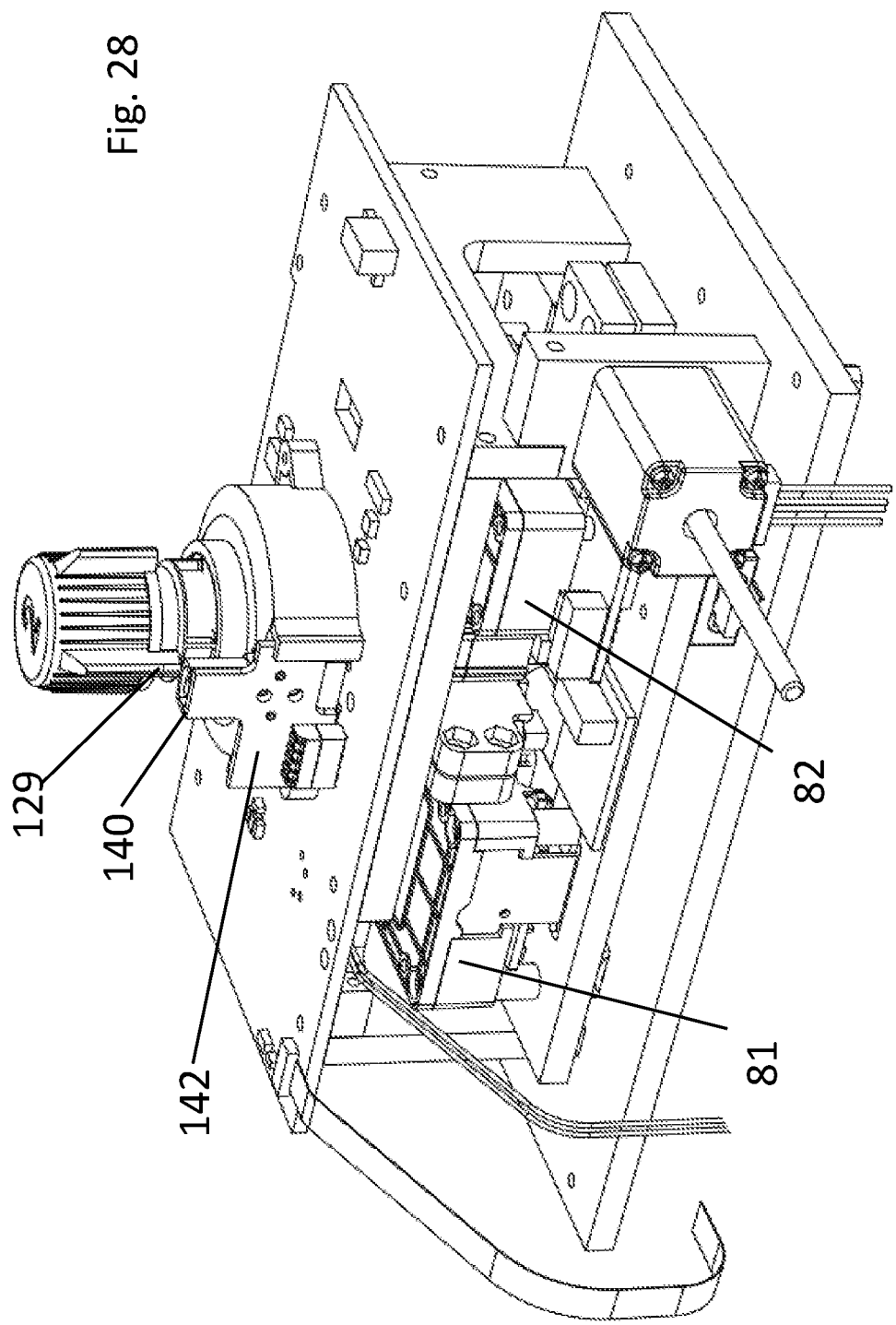
FIG. 28 is a drawing of the internal core of the instrument of FIG. 27.

FIG. 26 shows a full external view of the cartridge in the fully dispensed configuration with the dispense Cap 120 fully located and locked onto the cartridge body 101. The dispense assembly cap 120 has features in its form to assist rotation and handling, but it also includes a unique moulded feature 129 that projects further out and/or further down than any other features of the cap 120. The instrument incorporates a sensor that detects the position or proximity of this feature 129. This sensor output is used by the instrument controller and its controlling software to confirm that the cap 120 is fully closed and rotated around to the fully closed position. FIG. 28 shows the relationship between the cartridge and the instrument with the dispense cap in the fully closed position. In the fully closed configuration, the cap 120 has projection 129 in proximity of and detected by the electronic sensor 140 mounted on a circuit board 142. In the described embodiment, the sensor 140 is a retroreflective type optical sensor that incorporates both an infrared light emitting diode and a matching optical sensor. When the feature 129 is brought into close proximity, reflected illumination from the light emitting diode is detected by the nearby optical sensor 140. This signal is used by the instrument controller to confirm that the cap 120 is closed. In a typical instrument application workflow, the user is prompted to fit and close the dispense assembly cap 120 until such time as the cap fully closed feature 129 is detected as described above. The diagnostic test then only proceeds to amplification, detection and generation of a test result after this detection. If after an extended time the cap 120 is not detected, this can optionally be considered by the instrument to constitute a fault or misuse, and an error message displayed on the instrument LCD display or communicated to one or more of the data interfaces. This arrangement has the advantage that the test will only proceed to generate a diagnostic result if the cartridge is confirmed to be used correctly within a reasonable time and the dispense function fully completed. This confirmation provides self-checking by the instrument and improves confidence in the final test result.

Tests Other than Nucleic Acid Amplification Testing.

The test reagents contained within the cartridge prior to test can be configured for other types of testing not necessary utilising nucleic acid amplification. For example, direct chemical reaction detection can be used in some embodiments to detect the presence of trace elements or additives within a sample. Optionally, immunoassay detection methods can be used to directly bind to and provide detection of specific proteins within the sample material that has been diluted and dispensed into one or more test tubes.

Manually Operated, Visually Read, Non-Instrumented Cartridge Operation

In some applications, the cartridge can be used manually without an instrument, where the cartridge is held in one hand, and the first cap removed with the other hand, the sample added and the second (dispensing) cap fitted and screwed shut. In this case, where the test tubes are visually transparent, the dispensing of fluid into the test tubes can be visually observed, and a colour or turbidity change observed over time to provide a diagnostic test readout or display. This approach uses the advantages of operating with a fully sealed cartridge once the sample is added and internally dispensing a measured volume of diluted, prepared sample fluid into the test tube without the use of external fluid transfer steps.

Optionally, a simple stand may be provided to support the cartridge for the purpose of removing the first cap, adding the sample, and fitting and closing the dispensing cap and its associated mechanism.

Optionally, a simple heater block may be provided to provide temperature control of the sample and test tube chambers of the cartridge assembly, but the cartridge is manually withdrawn to observe the test result visible in one or more coupled test tubes.

Instrument

Figure 13:
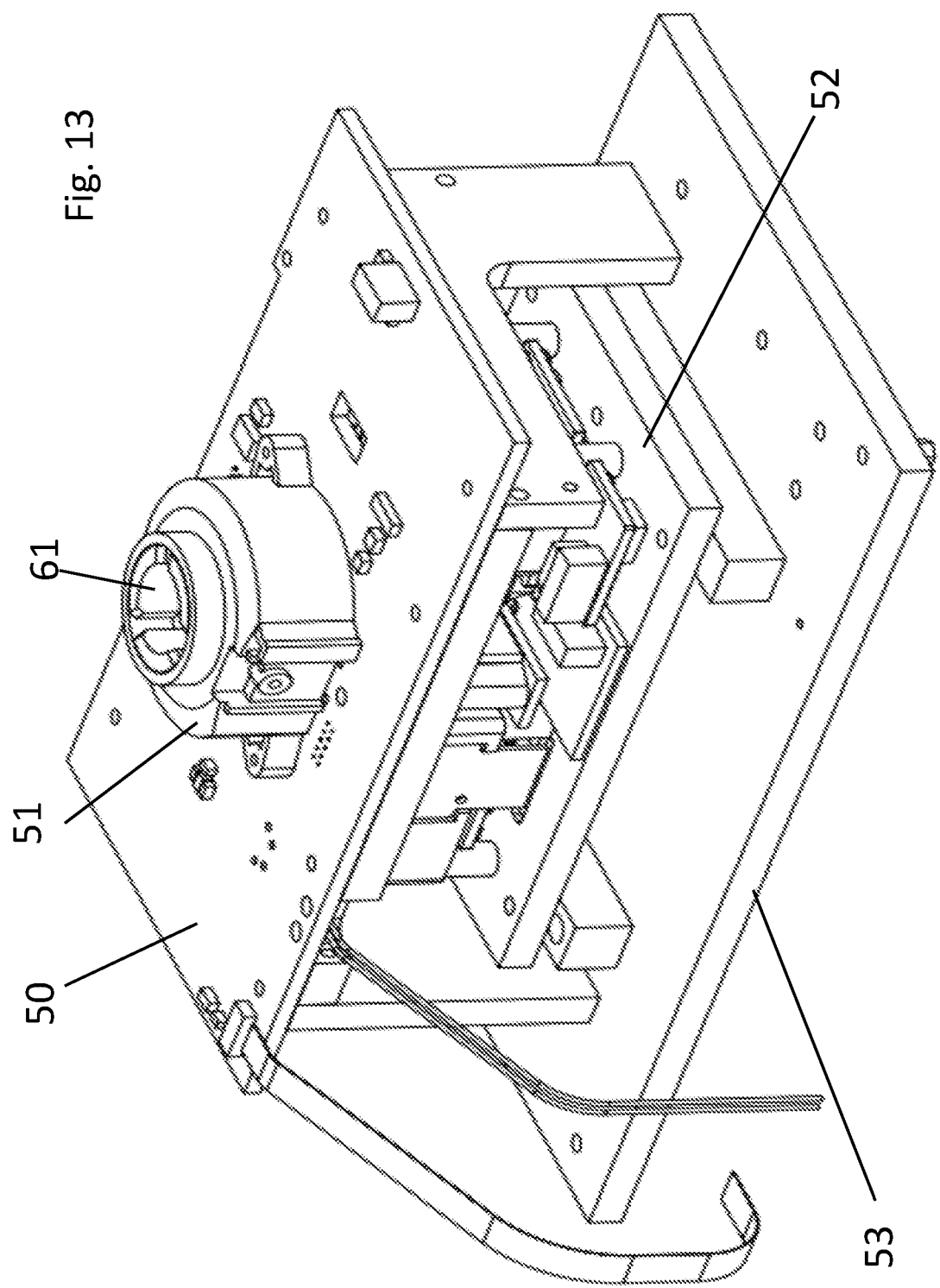
FIG. 13 shows the cartridge interface core of the instrument with upper and lower heater modules and detection sensors mounted on internal circuit boards and structural plates.

As described above, the cartridge can be operated within a diagnostic test apparatus or "instrument" to conduct a diagnostic test. The diagnostic test instrument 30 is shown in FIGS. 11 to 13, and includes a rigid enclosure or housing 31 and base 33, which may be constructed from moulded plastic or metallic sheet materials. Within this housing 31, a touch sensitive LCD display 32 is mounted. The instrument is operated by selecting touch sensitive controls on a user interface (not shown) rendered on the instrument display 32. However, in other embodiments the user interface may be implemented as physical controls or buttons to implement corresponding functions.

Instrument Controller

Figure 33:
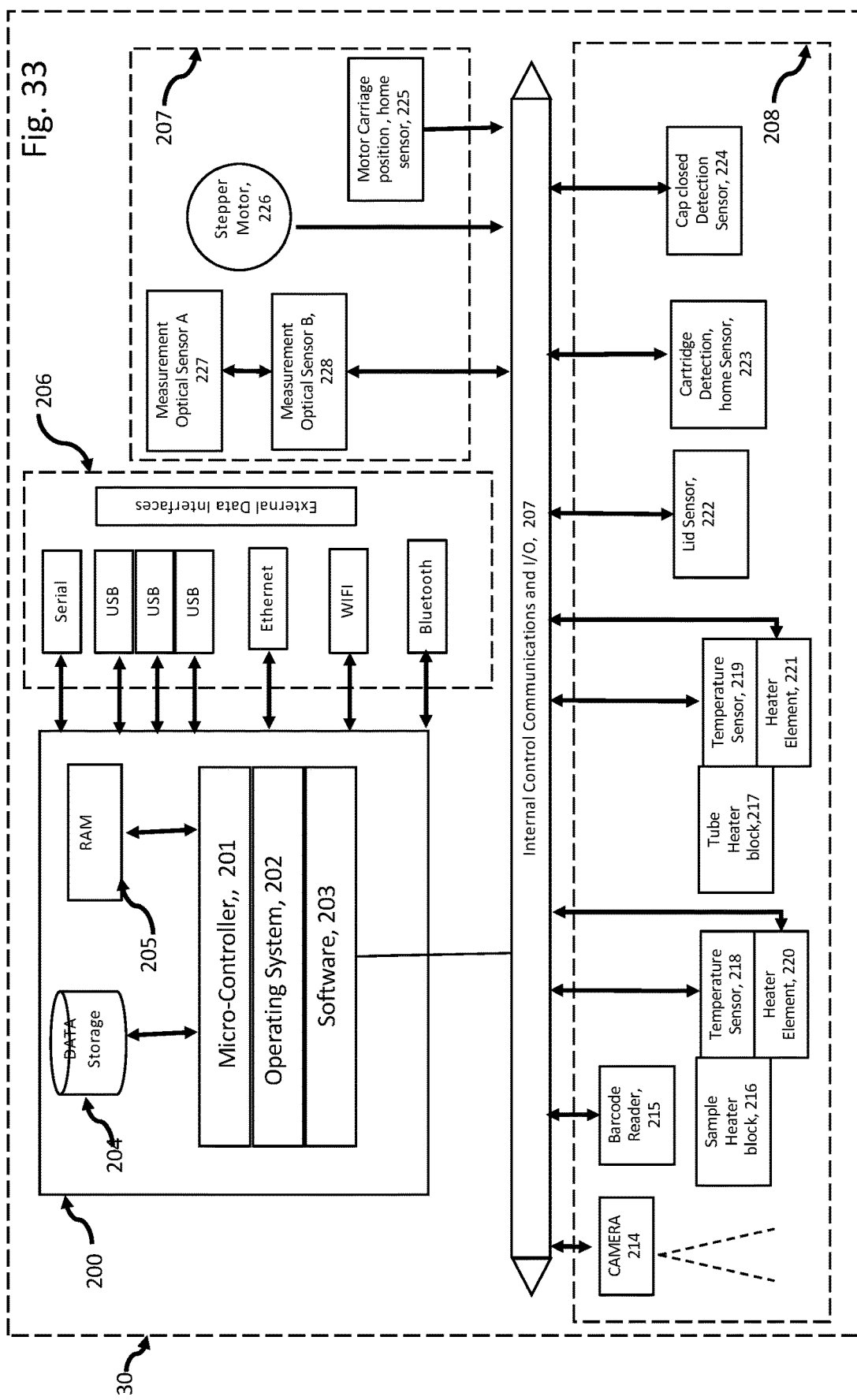
FIG. 33 is a block diagram of a control system of the instrument.
Figure 35:
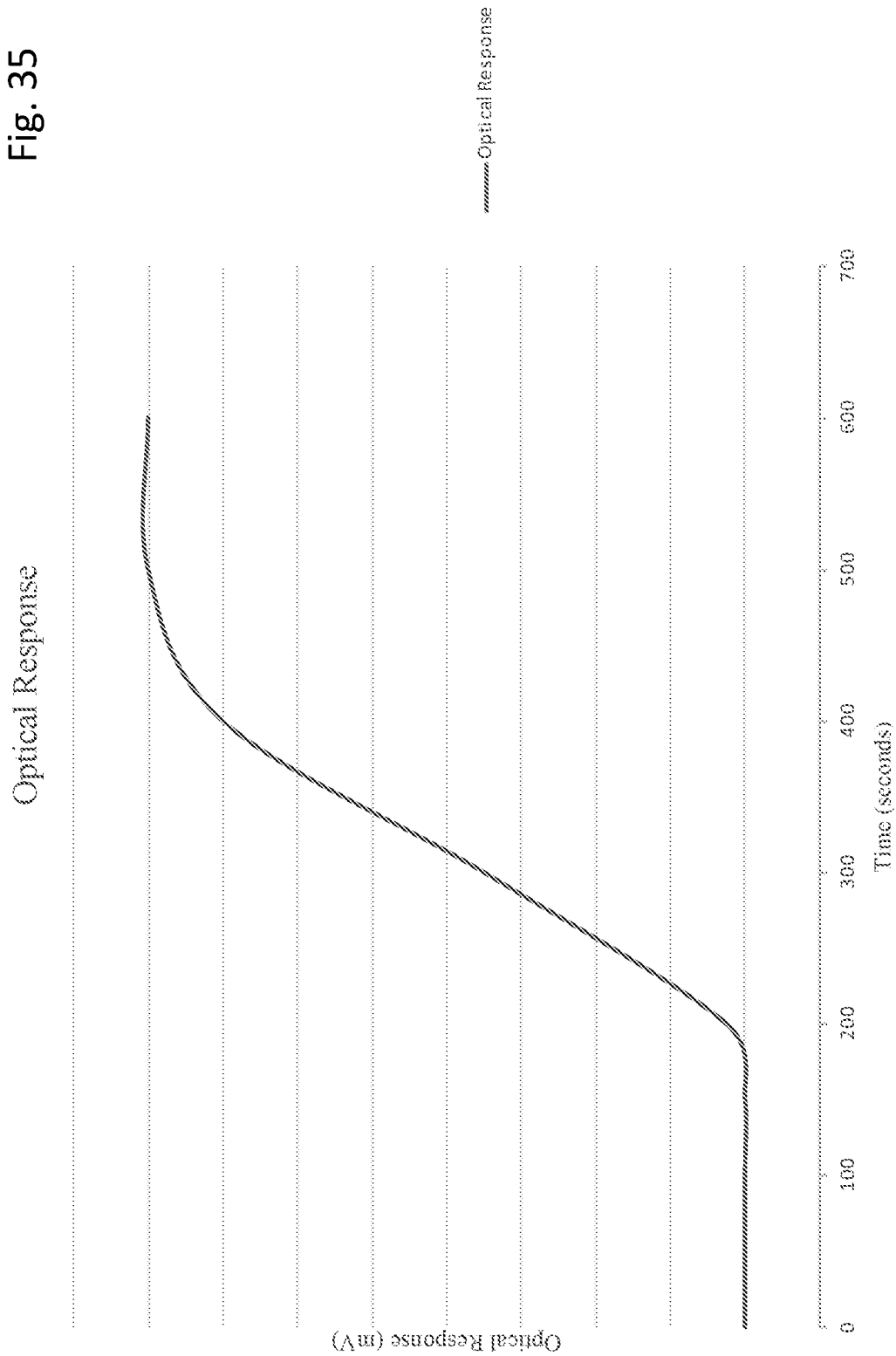
FIG. 35 is a graph of a typical amplification curve captured as a sequence of real-time measurements during PCT amplification within a test reservoir.

As shown in FIG. 33, the instrument 30 incorporates a microprocessor-based controller 201 configured to execute diagnostic test processes that control the sequencing and operation of the instrument's electrically operated functions. In the described embodiment, the microprocessor controller 201 is configured by way of an embedded operating system 203 and embedded software 203 stored in non-volatile memory 204 in communication with at least one external data interface processor 206 and the internal actuators, heaters, motors and sensors on data and control interface 207 as will be well understood by those skilled in the art. However, it will be apparent to those skilled in the art that some or all of the steps of the diagnostic test processes performed by the diagnostic test apparatus or instrument 104 can alternatively be implemented in other forms, such as configuration data for a field-programmable gate array (FPGA), or entirely in hardware form, such as an application-specific integrated circuit (ASIC), for example.

The non-volatile memory 204 also stores test results and instrument calibrations as data stored in one or more data files or in a database, and the information and data stored in the non-volatile memory 204 is retained, even when no power is provided to the diagnostic test instrument 30.

The instrument 30 also includes additional components external to and in communication with the controller 201, include, a lid sensor 222, a cartridge sensor 223, and a heater block 216 whose temperature is controlled by a heater element 220 and temperature sensor 218. All of these components are interfaced to the controller 201 by way of communications and control interfaces 208, via a shared bus 207 and I/O functions of an operating system 202.

The table below lists each component with manufacturer, part number and the part reference numeral in the block diagram of FIG. 33.

Figure 31:
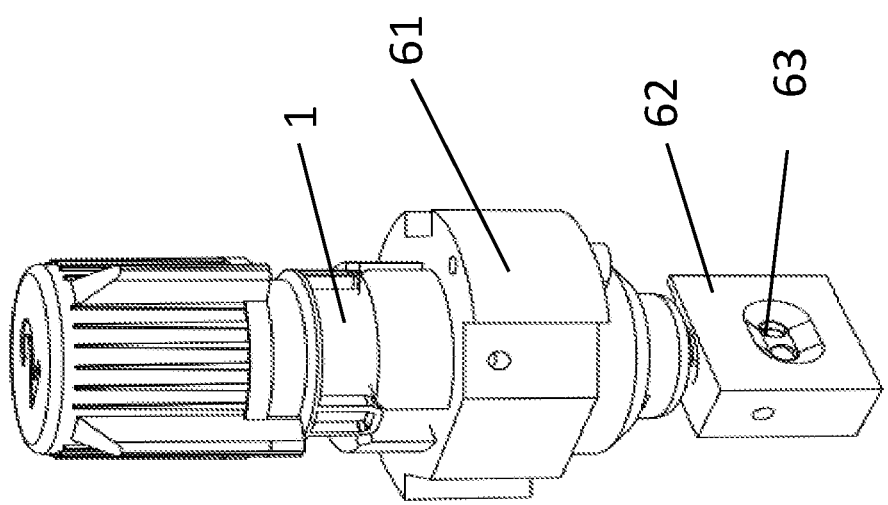
FIGS. 31 and 32 are drawings showing external and cross-sectional views, respectively, of the two heater blocks that surround the dual diagnostic test reservoir cartridge after it has been inserted into the dual diagnostic test reservoir instrument; an upper heater block provides temperature control of the sample preparation reservoir of the cartridge, while a lower block provides temperature control of the two test reservoirs; the lower block incorporates an optical port to allow the acquisition of optical measurements from the contents of the test reservoirs while they are under temperature control or temperature cycling; the lower heater block incorporates an optical port to allow optical excitation and fluorescence detection of the contents of the test reservoirs to be performed through the port while the contents of the test reservoirs are maintained at a controlled temperature or temperature profile.

| Item | Manufacturer | Part number | FIG. 31 Reference Numeral |
|---|---|---|---|
| Microprocessor | Microchip | PIC32MX695F512L-80V/PT | 201 |
| RAM | Within the Microcontroller | As above | 205 |
| EEPROM FLASH Memory | Microchip | SST25VF064C-80-4I-S3AE(it is EOL, will be changed to SST26VF064B-104I/SM on MZ Board) | 204 |
| Lid Detect Sensor | Allegro MicroSystems, LLC, hall sensor: | A3213ELHLT-T | 222 |
| Motor carriage Position Home Sensor | TT Electronics | Optek Technology, Inc | OPB829CZ | 225 |
| SD Card | Sandisk | MicroSDHC 8 GB | 204 |
| Temperature Sensor | Texas Instrument | TMP275AIDGKT TMP102AIDRLR | 218, 219 |
| Non Contactremp Sensor | Melexis Technologies | MLX90615SSG-DAA | Alternative for 218, 219 |

| Item | Manufacturer | Part number | FIG. 31 Reference Numeral |
|---|---|---|---|
| Heater Element | Caddock Electronics Inc. | MP915 series Power resistor | 220, 221 |
| Camera Module | OmniVision | Ov5640 | 214 |
| Barcode reader module | Datalogic | DSE0420 2D scan Module | 215 |
| Measurement Sensor | Axxin Fluorescence Optical Module A and B, Incorporates band pass filters, dichroic mirror, Osram Golden Dragon LED and photodiode. | Instrument customised assembly Photo diode: S2387-33R from Hamamatsu | 227, 228 |
| Cartridge home position Detection Sensor | Optecal Technology, optical interruption LED and photodiode assembly. | OPB315WZ | 223 |
| Cap closed Sensor | Osram | SFH 9206 | 224 |
| Stepper Motor | Ametek/Haydon Kerk - Non-Captive, Linear Actuator, 2.5 V, NEMA 8 | 21F4AC-2.5 | 226 |

Lid Function and Lid Detection

The instrument 30 shown in FIG. 11 includes a spring loaded sliding cover or lid 36. This cover 36 can be pushed back by the user, typically with the thumb of one hand. In pushing back the cover 36, a port in the top of the instrument is exposed that allows the user to insert the cartridge at the start of the test. The action of pushing back the cover 36 activates an internal electrical switch or sensor such that software application running on the instrument controller is aware that a test is starting and provides suitable prompts and feedback to the user. The cartridge as shown in FIG. 1, for a single tube embedment and in FIG. 18 for a two tube embodiment incorporates an annular moulded feature 13 on the cartridge body. This feature is engaged by the instrument lid 36 such that the lid 36 surrounds and slides over a section of this feature 13 when the lid 36 closes back against the installed cartridge. The tapered surface of this moulded feature 13, on the cartridge and action of lid 36, sliding over it acts to retain the cartridge within the instrument and secures the cartridge with some downward pressure such that the cartridge is positively located and the amplification tubes 3, 107, 108 are held in close thermal contact with the lower heater block.

This arrangement with the spring-loaded sliding cover 36 shown in FIG. 11, allows the cartridge to be securely retained with the lid 36 pressed against the cartridge under spring pressure but still allows free access by the user to the cartridge cap and cap threaded section of the cartridge to remove and fit the caps required to add and process a sample. The cartridge cannot be easily or inadvertently withdrawn by the user without the additional intentional action of pushing back the spring-loaded cover 36 to release the cartridge and then withdrawing the cartridge.

In other implementations, the lid 36 may be electrically actuated such as by use of an electric motor driving a pinion gear against an internal rack gear in the lid 36, the lid 36 sliding within linear guides. In the case of an electrically actuated lid 36, it is opened and closed under the control of the instrument controller 201 and software responding to user commands or parts of the test sequence where the cartridge is inserted or removed at the completion of a test.

Cartridge Detection

When the instrument lid 36 is opened, the cartridge can be inserted into the instrument port. Once inserted, the cartridge is detected by the instrument controller 201. This allows the instrument to provide prompts to the user to start a test and to identify the required test or the cartridge type. The instrument 30 shown in FIG. 11 includes a switch or sensor incorporated within the cartridge port that provides detection of the cartridge once it has been inserted and is in place.

In one implementation, this sensor is formed by an LED light emitting diode forming a narrow beam across the cartridge port, and an associated photoelectric sensor that receives and detects the beam. The presence of an inserted cartridge breaks this beam and allows the instrument and its controller and software to detect the presence of the cartridge. Other suitable sensors include those that rely on detection of optical reflection from the surface of the cartridge, or the use of a switch that is activated by the cartridge insertion or the use of a camera and associated image analysis in software to confirm the presence or absence of the cartridge.

Cartridge Identification

The diagnostic test system can be configured to process different test types, where these different tests can have different reagent contents, different intended target diagnostic test results and require different test processing conditions. Different cartridge test types can be identified by the user by entry on the instrument user interface, or can be identified automatically by the instrument through the detection of machine identifiable marks or labels on the cartridge assembly. These identifying makings can include features such as such as linear barcodes or 2D (e.g., QR) codes printed or etched onto the surface of the cartridge or applied on a printed label mounted either on the cartridge body or on the shipping cap.

Typically, each cartridge code identifies the cartridge type and the corresponding diagnostic test process and analysis to be applied in processing the cartridge. It also typically allows the instrument to read the batch or lot number and the expiry date of the particular cartridge. This data can be used to apply lot-specific calibrations, and to exclude expired cartridges from being used in tests. This information is also included as metadata in the test result data generated by the controller 201 during the diagnostic testing.

The instrument can incorporate a barcode sensor and image sensor to allow the imbedded controller 201 to read the cartridge type and identify its associated test method from a barcode mounted on the body of the cartridge or cap. This code may be a linear barcode, a 2D code type such as a QR code or Datamatrix, or a propriety set of markings or symbols. Alternatively, an integrated image sensor or camera can by the use of image analysis within the instrument controller 201 decode the contents of a barcode, 2D code or identifying marks on the cartridge or its cap. Alternatively, the user can be prompted to use a manually operated commercial barcode or 2D code reader connected to one of the external communications ports on the instrument to acquire the data contents of a code applied to the cartridge body or the cartridge cap. If the code is on the top of a shipping cap, the code can be read easily after the cartridge is inserted and detected within the instrument port, prior to removing the cap. Alternatively, the user can be prompted to enter the cartridge ID or type it into text field in the user interface, or to select the test type or cartridge from a drop-down list on the user interface.

Sample Reagent Heating Prior to Amplification.

The instrument incorporates two independent temperature control zones that surround and provide independent heat input to the sample fluid reservoir section of the cartridge and to the test or amplification tubes 3, 107, 108. The zones can be heated air chambers or heater blocks or the instrument may use another method of directly or indirectly heating or cooling the fluids in the sample chamber region of the cartridge and within the separated test tubes 3, 107, 108.

Figure 14:
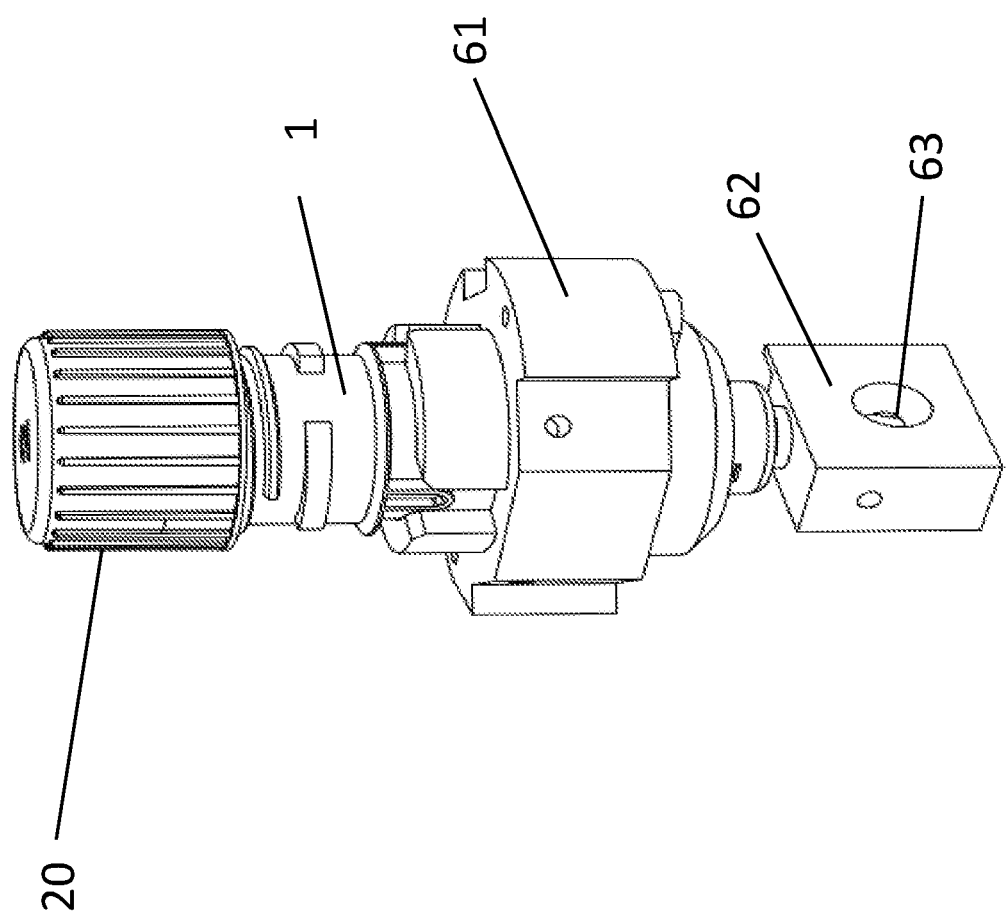
FIG. 14 shows a single test reservoir cartridge within the upper and lower heater blocks of the instrument, with other components of the instrument not shown.
Figure 15:
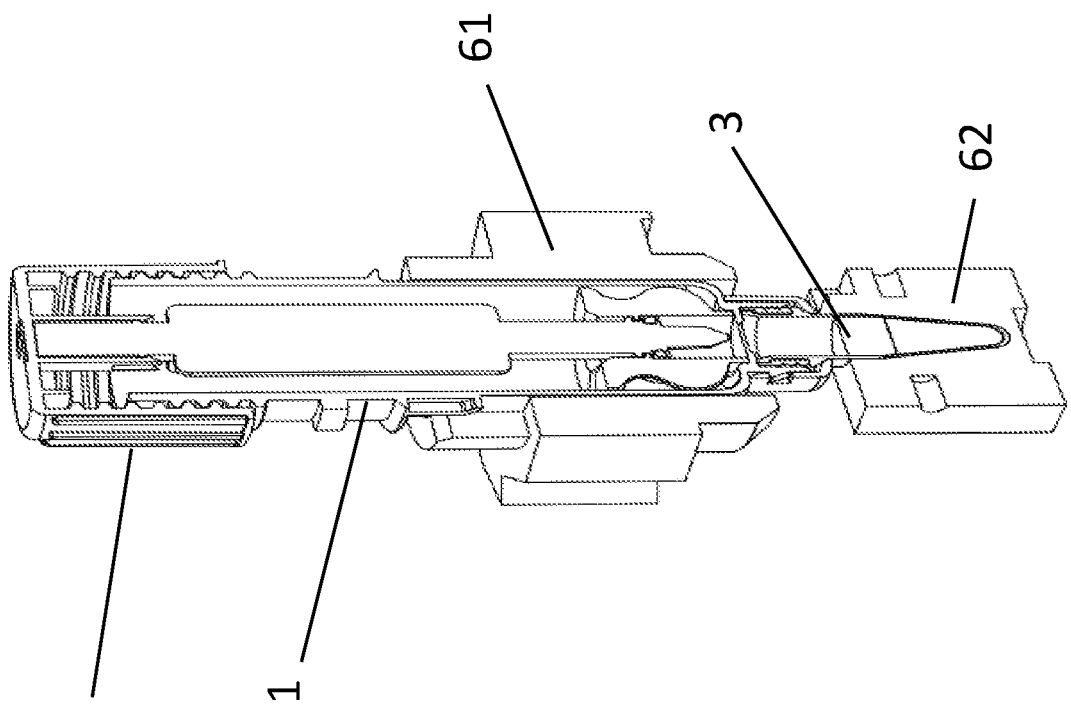
FIG. 15 is a cross-sectional view of the components shown in FIG. 14.

FIG. 14 shows an instrument configuration of the heater zones for a single amplification tube cartridge. In this example, electrically heated aluminium blocks 61, 62 are used to provide heat input into the inserted cartridge 1. The two blocks 61, 62 are heated and controlled separately, and are sufficiently insulated within the instrument that they can operate at different temperatures. The upper block 61 is electrically heated and controlled such that its temperature is under the control of the instrument controller 201. The feedback sensors are mounted on the aluminium block and temperature control of the aluminium block is used by the instrument controller 201 to heat and predict the temperature imparted to the fluids within the cartridge. In another implementation, the temperature sensors are of a non-contact type such as infrared temperature emission sensors, and they are used to directly measure the temperature of the internal cartridge fluids as the walls of cartridge are constructed from materials with suitable transmission at the wavelengths needed to undertake this direct internal temperature measurement.

In a typical application, the sample heater operates from 40 degrees Celsius to 95 degrees Celsius, dependent on the type of sample to be processed and the cell types and cell lysis required.

In a typical isothermal amplification application, the amplification heater block 62 operates at a fixed temperature such as 65 degrees Celsius. In a typical PCR application, the amplification heater block heats and cools in steps between set temperatures over a typical range of 50 degrees Celsius to 95 degrees Celsius. The amplification heater block 62 in FIG. 14 incorporates a port hole 63. This hole 63 allows optical detection of the tube contents to allow both real time and endpoint detection, and determination of a qualitative or a qualitative test result.

FIG. 13 shows the internal structure of the instrument and in this view the integration of the upper, sample heater block 61 is shown. The sample heater block 61 is mounted on its controlling circuit board 50 such that the cartridge port is presented at a top surface of the instrument. In this view, the heater block 61 is encircled by a plastic insulating cover 51 to prevent excessive loss of heat from the heater block 61 once it is at temperature.

Figure 32:
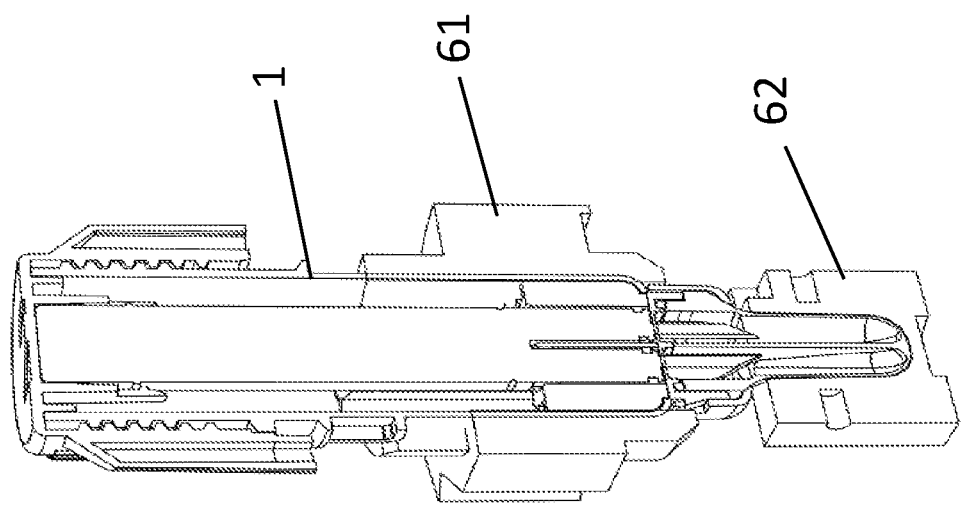

The two tube implementation of the instrument has the same general arrangement of heater zones. This arrangement of temperature control blocks that surround sections of the cartridge is shown in FIG. 31, with the sample heater block 61 and the amplification heater block 62. In this implementation, the amplification heater block 62 has two port holes 63 on each side of the block 62 for each of the internal amplification tubes 107, 108. These ports 63 allow each of the sensors to move to position and acquire optical test measurements from each of amplification tubes during the test. FIG. 32 shows the cartridge assembly and the two heater blocks 61, 62 in cross section.

Temperature Control or Temperature Cycling.

The amplification test tube 3 or plurality of test tubes 107, 108 mounted at the base of the cartridge enter a corresponding heating zone when the cartridge is placed into the instrument port.

This heating is achieved by insertion into the temperature controlled zone, including by direct contact or close proximity to a temperature controlled heating and cooling block 62.

In an alternative implementation, an air cavity maintained at a fixed temperature by recirculation within a cavity that envelops the test tubes is used to control the temperature in the test tubes. Using either of these temperature control implementations, the test wells 3, 107, 108 are either maintained at a fixed temperature for isothermal DNA amplification, or are cycled between different temperatures for PCR type DNA or RNA amplification.

Sample Chamber and Test Tube Mixing

In some diagnostic testing, mixing of the contents of either the sample preparation reservoir or the test/amplification reservoirs is necessary for the test to run correctly, or to improve the test reliability or accuracy. To achieve mixing, magnetic inserts such as small steel or ferrite balls can be included in either the sample preparation reservoir or the test/amplification reservoirs 3, 107, 108 during reagent loading of the cartridge during its initial manufacture. By way of example, this is shown in FIG. 2 for a single amplification cartridge.

In FIG. 2, a steel ball 14 is included in the sample chamber section of the cartridge body 1, and a steel ball 15 is included in the amplification test tube 3.

Within the instrument, permanent magnets are fitted to an actuator or to the moving sensor carriage such that, as the carriage traverse passes each of the test wells, a magnet fitted high lifts the particles 14, 15 and they subsequently fall back to the base of the well under gravity after the carriage has passed. This ball movement within the amplification tube fluid induces a fluid mixing action.

In an alternative implementation, high and low magnets are fitted to pull the mixing particles or balls 14, 15 to alternate positions in each well as the carriage passes. This alternating or reciprocating movement of the mixing ball 14, 15 within each well also induces mixing in the well fluid. This arrangement also has the advantage that it can be configured to pull the included particles or ball 14, 15 to a preferred position when each sensor is close to the well, such that these particles 14, 15 do not interfere with the optical measurements of the well contents.

A similar approach of applying an external magnetic field by moving a permanent magnet or plurality of magnets into proximity to induce movement of the magnetic particles or steel balls 14, 15 can be applied to the sample preparation reservoir to induce mixing within the sample fluid. Mixing within the sample preparation reservoir can be used to mix introduced sample material with the sample preparation fluid to dilute and prepare the sample material for amplification. This preparation mixing can also improve cell lysis and the extraction and preparation of the target DNA or RNA nucleic acid material within the sample. In an alternative to physically moving a permanent magnet, one or more electromagnets can be activated by an applied electric current under control of the instrument controller. These induced changing electromagnetic, magnetic fields can be used to cause movement of the magnetic beads or steel balls 14, 15 within either the sample preparation reservoir 1 or the test/amplification reservoirs/tubes to cause fluid mixing in either of these zones in the cartridge.

Fluid Fill Detection, Image Analysis

One or more image sensors 214 incorporated within the instrument can capture digital images of the cartridge and the progression of the dispensing mechanism components and the state and progress of the fluids contained within the cartridge. These digital images are processed by software image analysis within the instrument controller to provide control and status outputs. The digital output from the one or more image sensors 214 can be used to confirm the sequence progression and confirm the correct release and flow of test reagents within the cartridge such that the integrity of the test can be confirmed by the controller 201 and used to improve the reliability and safety of the test result. The image sensor 214 can be used by the controller 201 to observe internal fluids and the mechanism parts within the cartridge, and to calculate a control interpretation through the use of image analysis by the instrument controller.

The image sensor 214 can confirm the operation and position of the dispensing mechanism to confirm incomplete or correct and complete operation of the cartridge and prompt the user to at completion or automatically progress to the next step in the apparatus process to acquire the final test result.

The image data acquired by the image sensor 214 and in subsequent image analysis can be used by the controller 201 to determine the levels of the dispensed sample fluid in each of the test tubes 3, 107, 108 and to use this level to determine that the sample fluid dispensing has completed correctly. The level of the fluid dispensed into each of the one or more test tubes 3, 107, 108 within the cartridge can be used to compensate the test result for tolerances in the dispensing operation. The level of the fluid with each test tube can be converted by the controller 201 to a volume by using a mathematical model of the tube 3, 107, 108 or by using a look up table. The volume of dispensed fluid can influence the concentration of the test regents within the test chamber fluid once they have dissolved into the dispensed fluid. By measuring the volume of the dispensed sample fluid, the concentration of reagents within each test tube 3, 107, 108 can be calculated. From a series of previously conducted experiments or from a model of the test reactions, the effect of test reagent concentration on the test result and the interpretation of the time series measurements of the test to interpret the result can be known and adjusted or compensated for within the apparatus.

The fluid sample preparation reagent stored in the cartridge can be coloured with a dye. If the final amplification test is detected using fluorescence, the fluid reagents such as the sample lysis buffer stored in the cartridge sample chamber can have a coloured, non-fluorescent dye added. This dye can be used by the image sensor 214 to visually image coloured or contrasting fluid flow into the cartridge test tubes 3, 107, 108 to confirm the dispensing action and confirm the dispense volume. The addition of a coloured dye to the fluid improves contrast in the resulting images, but does not adversely affect the fluorescence excitation and emission from the tube contents. As an alternative use of the approach, image analysis of an image of the fluid dispensed into one or more of the coupled test tubes 3, 107, 108 can be used to measure the volume within the tube 3, 107, 108, and this measurement can be used to compensate the test result calculation for the amplification volume. This compensation can be of particular significance for a quantitative test result where the concentration of reagents in the test tube 3, 107, 108 can influence the measurements and reaction response.

Instrument Sensors.

Figure 16:
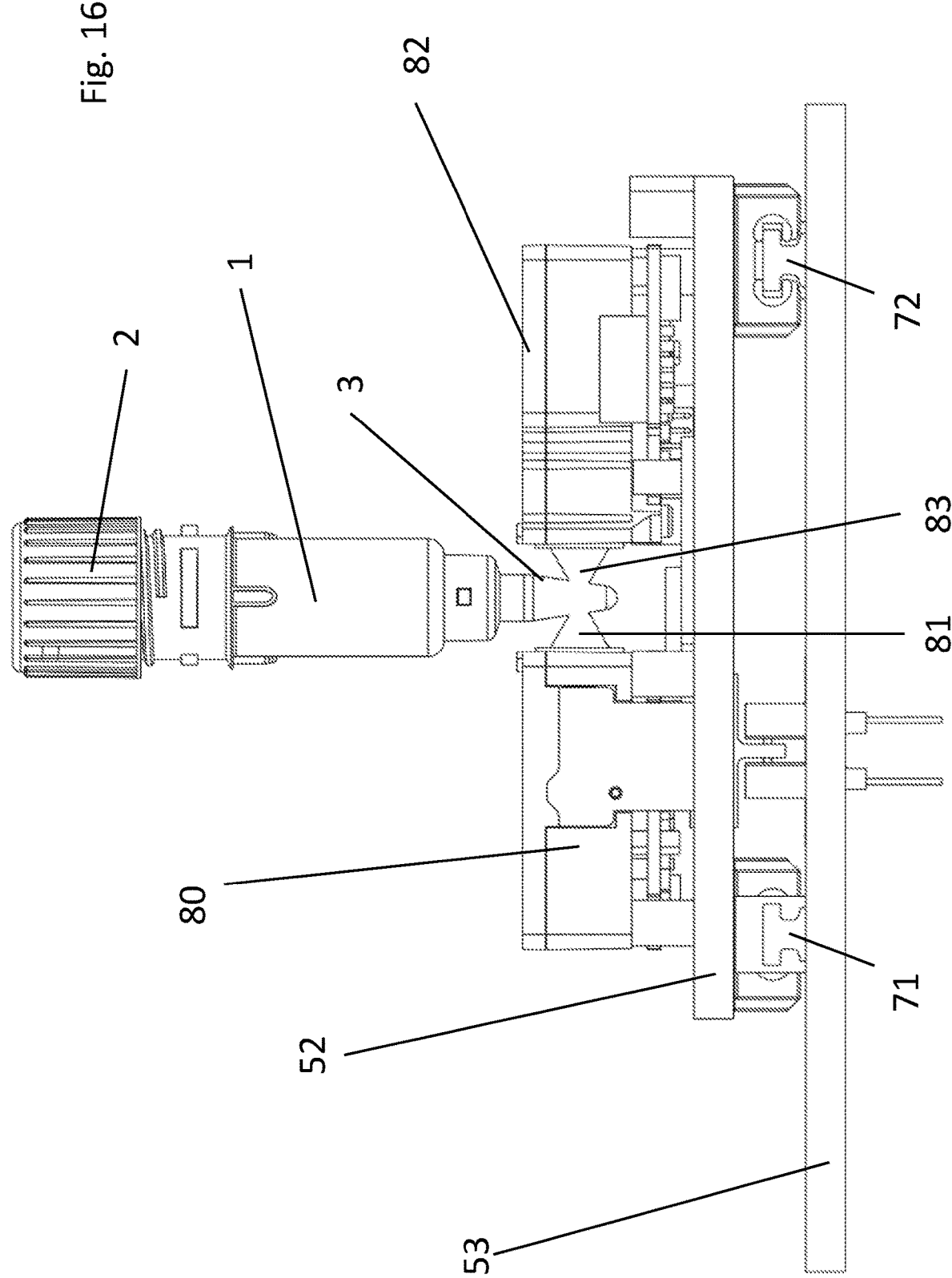
FIGS. 16 and 17 show the single test reservoir cartridge and the relationship of the diagnostic test reservoir to optical sensors mounted within the instrument, with many other components of the instrument not shown; the optical focal cones that represent the field of coaxial excitation and light collection to and from the exit lens of the sensor for the example of fluorescence detection are included to illustrate the acquisition of optical measurements from the test reservoir.
Figure 17:
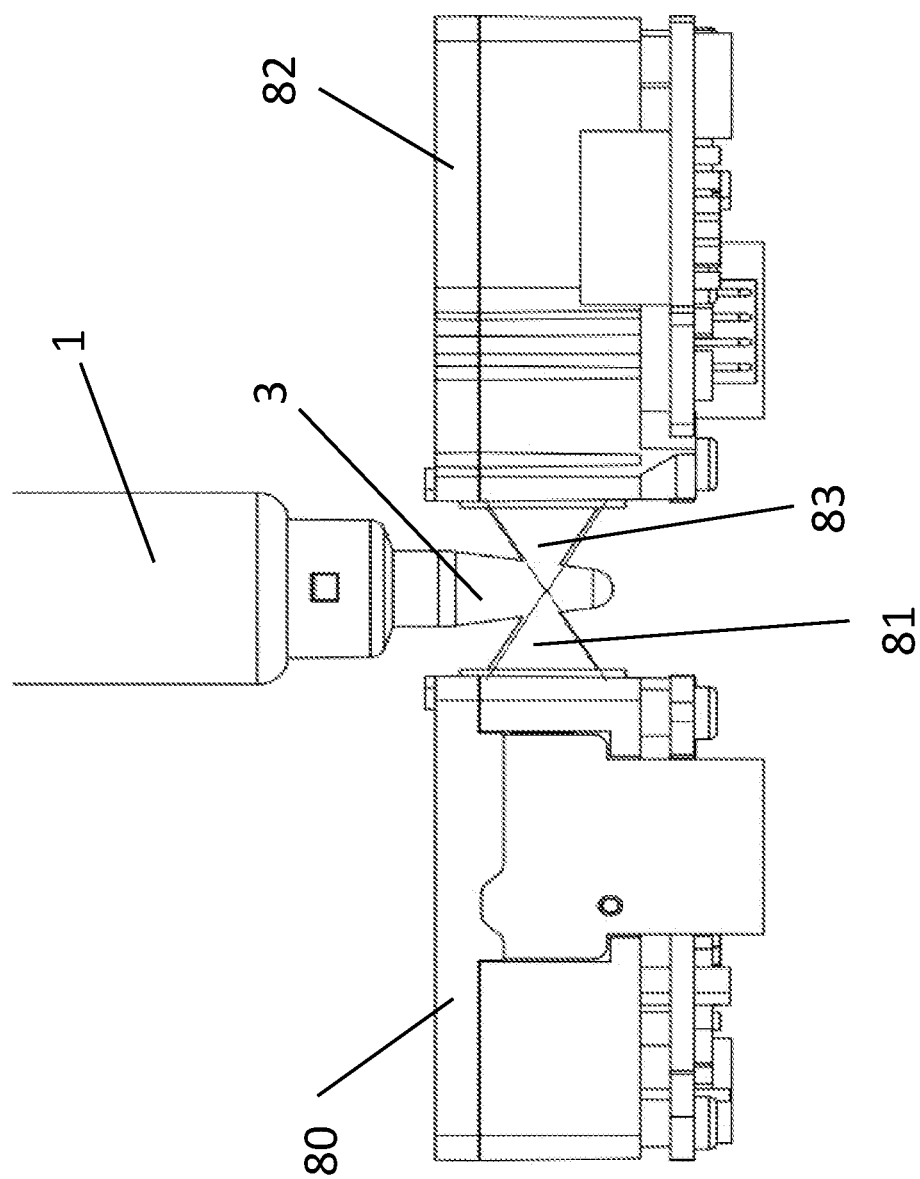

FIG. 16 shows the arrangement of the optical sensors within the instrument. Two independent optical sensors 80, and 82 are shown. The optical focal cone 81 of one sensor 80 is shown schematically, as is the optical focal cone 83 of the other sensor 82. This is shown with the same item numbers in more detail in FIG. 17. FIG. 17 shows how the optical sensor focal cones 81 and 83 can each excite and acquire optical fluorescence signals from the amplification tube 3. In these figures, the amplification heater block 62 is not shown for clarity; however, in the fully assembled instrument, these optical measurements are acquired through ports in the side of the heater block 62 that surrounds the amplification tube 3.

FIG. 16 shows the optical sensors mounted on plate 52 that can travel linearly on rails and linear bearing blocks 71 and 72, where these rails and blocks are shown in cross-section in this view. The position motor 70 provides the capability for the instrument controller 201 to accurately position the sensors with respect to the tube 3 to acquire measurements that represent the DNA or RNA detection probe emissions within the tube 3.

In the case of single amplification tube cartridge, the sensors can both be positioned in line with the tube 3 and in a fixed arrangement such that the bearings, linear rails 71 and 72 and the position motor 70 are not required. However, the use of the linear motion arrangement and position motor allows the sensors to also be moved to self-test reference locations and to park the sensors away from the tube location when not used, which can have advantages in some applications.

Internal Reference Regions.

The instrument can be configured with one or more optical reference regions within the field of view of the detection sensors or within the scanning path of these sensors. These reference regions can be configured either by their material or surface coating properties to have a known optical reflectance, absorption or fluorescence suitable as a reference test for the intended detection mode of the sensors. These regions can include a plain reference background with a known stable reflectivity, absorption or fluorescence. For example, in the case of fluorescence detection sensors, the reference regions can be localised plastic components with inorganic or organic additives to tune their fluorescence response to be a within a suitable test range for the sensors.

Self Test Confirmation of Calibration.

The inclusion of reference regions or reference locations within the instrument allows the instrument to confirm the operation and accuracy of its imaging calibration within a self test function. Alternatively, the instrument can prompt the user to insert a test cartridge with known optical output or response from the test tube locations, where the cartridge is reference cartridge configured for the purpose of allowing the instrument to conduct a self test or a calibration function. This capability provides improved confidence and user safety in using the system with the potential to have an incorrect reading or false test result.

Test Readings.

While the amplification is running, test readings are taken by optical sensors. These sensors are configured to have an optical path that incorporates the contents of the amplification test tubes through holes, optical ports or window 63 in the lower amplification heater block 62 and corresponding optically transparent sections on the test tubes. Where detection is required at one or more amplification tubes 3, 107, 108 and also at reference self-test regions, a scanning approach is used to move the sensors across these multiple detection points and provide measurements at each point of interest for the diagnostic test. These measurements can use optical absorption, florescence emission or bioluminescence emission to detect specific biological or genetic sequence markers in the test tubes 3, 107, 108.

Figure 29:
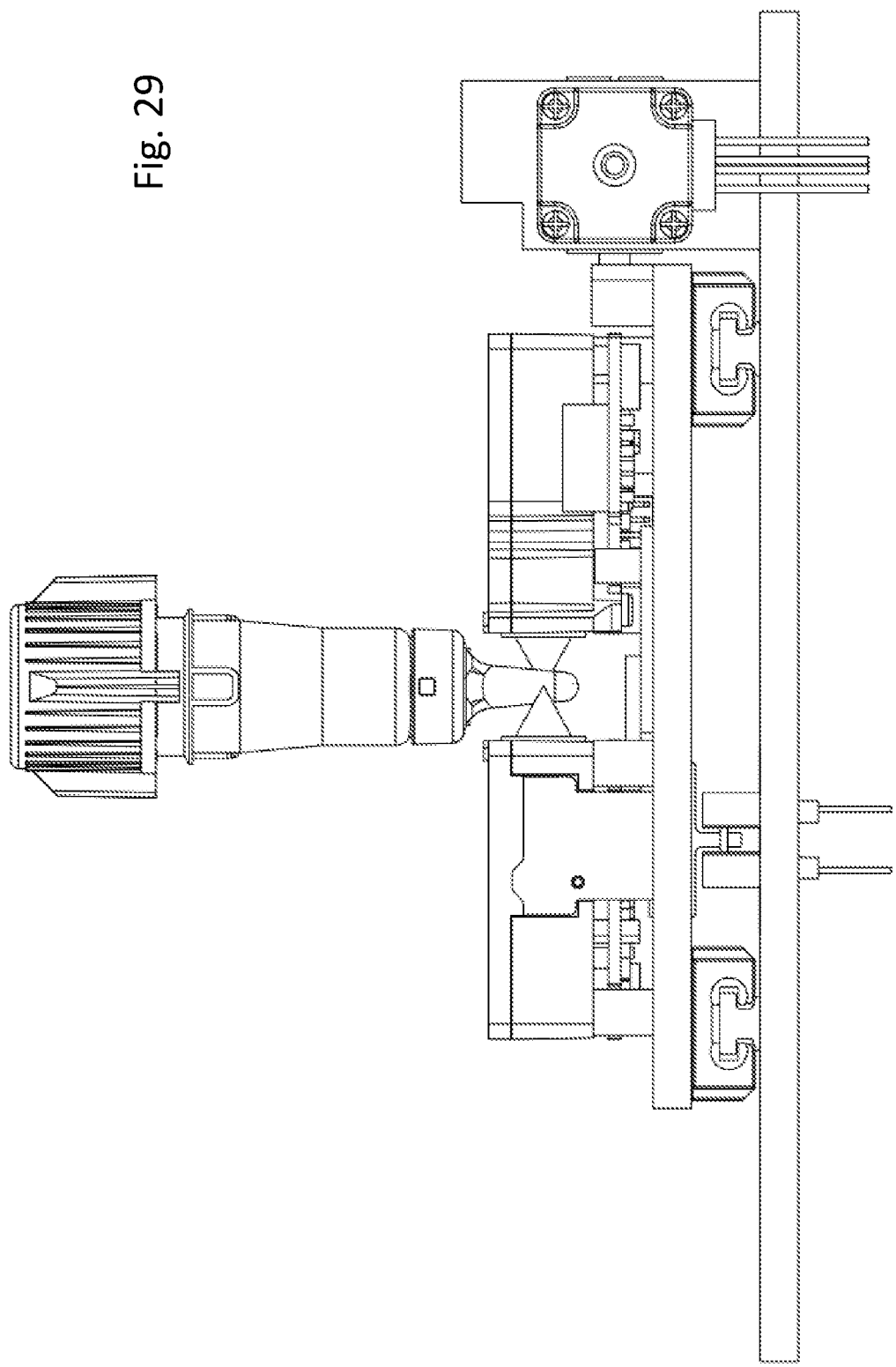
FIGS. 29 and 30 show the dual test reservoir cartridge and the relationship of its diagnostic test reservoirs to optical sensors mounted within the dual test reservoir instrument, with many other components of the instrument not shown; the optical focal cones that represent the field of coaxial excitation and light collection to and from the exit lens of the sensors for the example of fluorescence detection are included to illustrate the acquisition of optical measurements from the test reservoirs; to allow readings from the two test reservoirs, the sensors are mounted on a moving plate, where the linear bearings and the stepper motor that controls the scanning movement of the sensors are shown in end view in FIG. 29; the sensors are mounted on plate that is itself mounted on linear bearings and attached to a motor driven lead screw, allowing the instrument to acquire optical measurements from each sensor for each of the two diagnostic test reservoirs in the cartridge.
Figure 30:
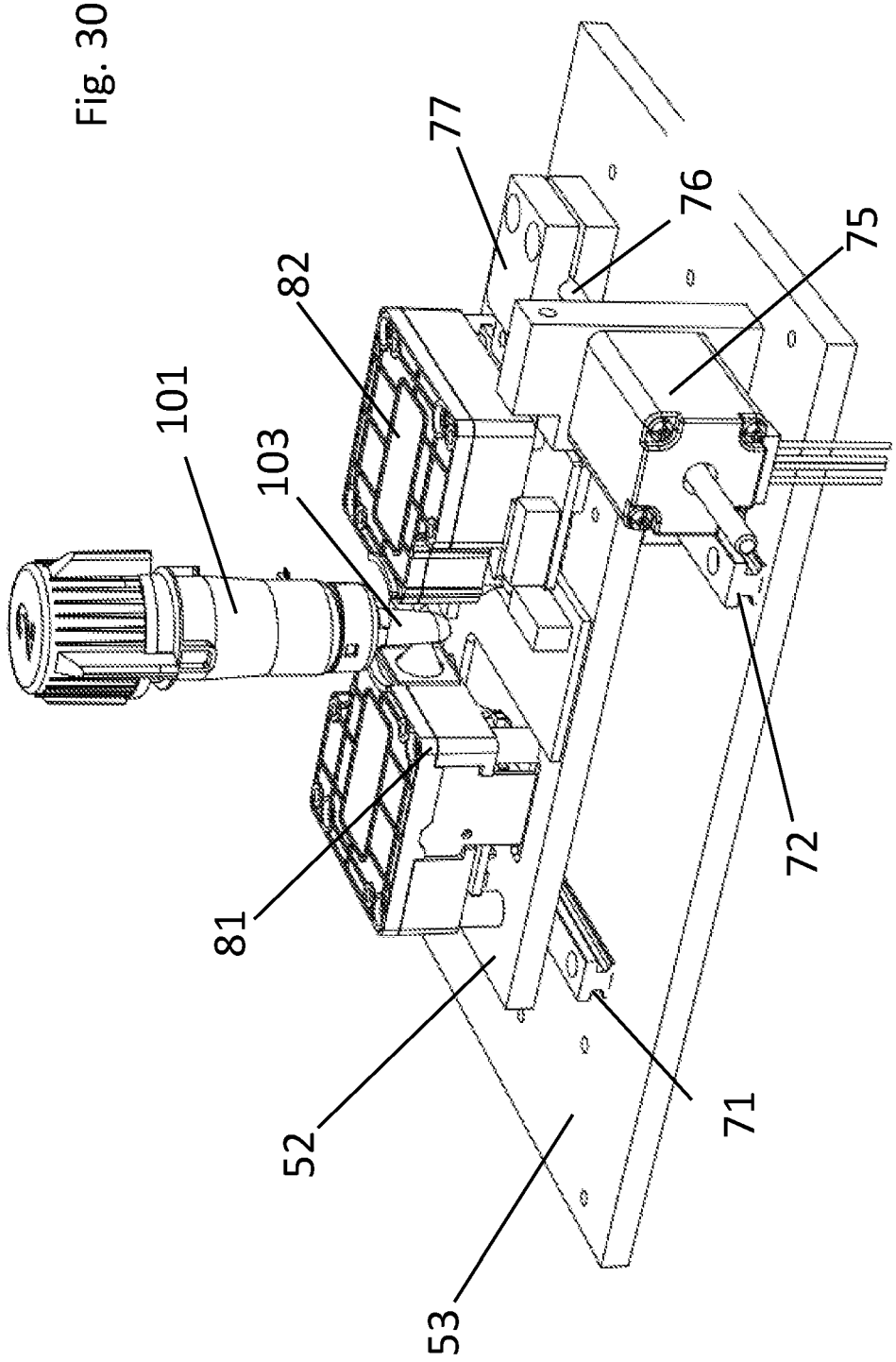

The measurement arrangement is shown in FIG. 16 for the single amplification format cartridge, and in FIGS. 29 and 30 for the multiple amplification tube configuration. In FIG. 30, the optical sensors 61, 62 are mounted on a carriage 53. The carriage 53 is mounted on linear rails 71 and 72, such that each of the sensors can move past each of the required optical detection locations.

The movable carriage 53 is attached to a lead screw, and this screw passes through a nut mounted within a hollow shaft position motor. In this example, the position motor 70 is a stepper motor under control of electronics and the controller 201. Other arrangements for providing position control of the carriage to provide optical scanning will be apparent to those skilled in the art, including linear motors, a belt drive or a rack and drive pinion gear arrangement.

This arrangement can move the sensors 61 and 62 such that they successively align with each test tube in the cartridge 101. This scanning movement can be used to acquire measurements for each sensor at each test well location. This scanning process can include a sequence of moves whereby each sensor is positioned and stopped in line with each test well in turn. At each position, a set of test measurements is taken. At the completion of a set of moves and measurements, the carriage is moved back to its starting position and the scanning process repeated.

An alternative sensor scanning arrangement is to move the carriage at a constant speed so that the carriage and the sensors it carries are moved across the sensing window of each of the test wells at a constant speed. A continuous series of measurements are then acquired during this constant speed scanning move.

This signal is made up of many measurements, and once these have been acquired, the controller 201 can locate the peaks that correspond with each test well 107, 108. These peak or maximum points correspond with the well optical signal, and are a similar measurement to that which would have been acquired if the sensor was accurately stopped at each well location with the sensor aligned with the optical window 63 through the heater block 62 and test well 3, 107, 108. The advantage of the moving acquisition method, without stopping to acquire measurements at each well location, is that the carriage does not need to stop for each measurement, and therefore the overall scanning time and measurement repetition rate for each test well can be much improved. This then allows a higher measurement sampling rate for each test well.

In many applications, the test outcome is determined by the dynamics of the reactions in the test well 3, 107, 108, and in such applications a series of measurements needs to be acquired at an adequate sample rate while the test is running to have the data needed for analysis and subsequent determination of the test outcome. FIG. 33 shows a typical amplification curve measured in real time as a sequence of measurements acquired during amplification from detection emissions from within the amplification tube 3, 107, 108. The form and amplitude of the curve, including its final level, gradient during its rise and the time after start that curve gradient occurs can be used to determine a test result by the instrument. The test result may be qualitative such as positive if the target nucleic acid is detected, and negative if it is not, or it may be quantitative and expressed as a level such as parts per million, or for example as the percentage of the DNA within the DNA of the sample material.

Alternative Measurement Methods

Although the description above refers to optical measurements of the test well to determine a test result, it is recognized that sensors with alternative measurement methods can operate in the same diagnostic test apparatus/instrument and with the diagnostic test cartridges described herein. These sensors can use magnetic, electrical, atomic or physical properties of the test fluids to acquire measurements suitable to determine a test result.

UV Denaturation

The diagnostic test system can also incorporate a source of ultraviolet (UV) illumination mounted within the instrument assembly and operated under control of the instrument controller 201 such that it can be turned on and off when required. This light source may be a suitable UV globe or a UV light emitting diode (LED) and can include optical components such as lenses to focus the UV into a region that is appropriate to illuminate the amplification tube contents with UV light.

This illumination can be a larger fixed illumination source to illuminate the whole of the amplification tube(s) 3, 107, 108 and the cartridge volume as a whole, or can alternatively be implemented as a localised light source within the scanning carriage to denature the amplified contents of the test wells as the scanning arrangement moves past the test wells 3, 107, 108. In any case, this UV illumination is controlled such that, at the completion of a test, and prior to the user being prompted to remove the cartridge, it can be turned on to denature and sterilize the contents of the amplification tubes and cartridge, in particular to denature any genetic, nucleic acid material.

This ultraviolet LED can also include focusing optics to focus the UV light onto each test well 3, 107, 108 (and during scanning if scanning is used). The carriage can be scanned as a continuous movement, or it can move and stop at each well 3, 107, 108. By either method, high intensity UV illumination is applied to each test well in sequence. The UV illumination level and the exposure duration is configured by the controller to ensure that the DNA genetic amplicon contents of each well are completely denatured and will not undergo further amplification in the event that the test well contents were to be released and introduced into another test.

This denaturing of the test well contents can also be achieved or enhanced by operating the test well heater at an elevated temperature such as 100° C. for a period of time sufficient for the genetic material in the test wells 3, 107, 108 to be broken up and denatured within the test well solution. The combination of increasing the temperature of the test wells 3, 107, 108 using the heater block 62 under instrument control and applying UV illumination can be used to increase the efficiency of the breakdown and destruction of the genetic nucleic acid material within each test well 3, 107, 108.

This function has the advantage that the risk that amplicons contained within amplification tubes escaping into the environment surrounding the instrument. These amplicons can contaminate the sample addition of future tests and cause false positive results. However, the primary protection against the release of amplicons is the sealed design of the cartridge such that the amplicons are retained within the amplification tubes 3, 107, 108 at the completion of the test. However destroying the amplicons or greatly reducing their number by use of heat or UV illumination at the completion of the test can further reduce this risk in the event that the cartridge seals are compromised or a used cartridge is damaged after removal from the instrument.

Optional Dispense Insert Fluid Functions.

As the dispense insert is inserted into the cartridge body 1, the sample fluid flows around it and through the open ended cylindrical dispensing bore, as shown in FIG. 36. FIG. 37 shows the dispense insert in an isometric view. The dispense insert 22 has fins with fluid paths past the outside of the cylindrical bore and also slots down only a portion of its length. Consequently, sample fluid that has entered the cylindrical bore can exit through the slots when the sealing plunger is not fully pressed into the solid or 'un-slotted' portion of the dispense insert 22. FIG. 36 shows typical fluid flow lines. This description applies equally to case of the dispense insert in multiple test tube cartridges such as the two tube insert 122 shown in FIG. 22.

Filter Function

Figure 38:
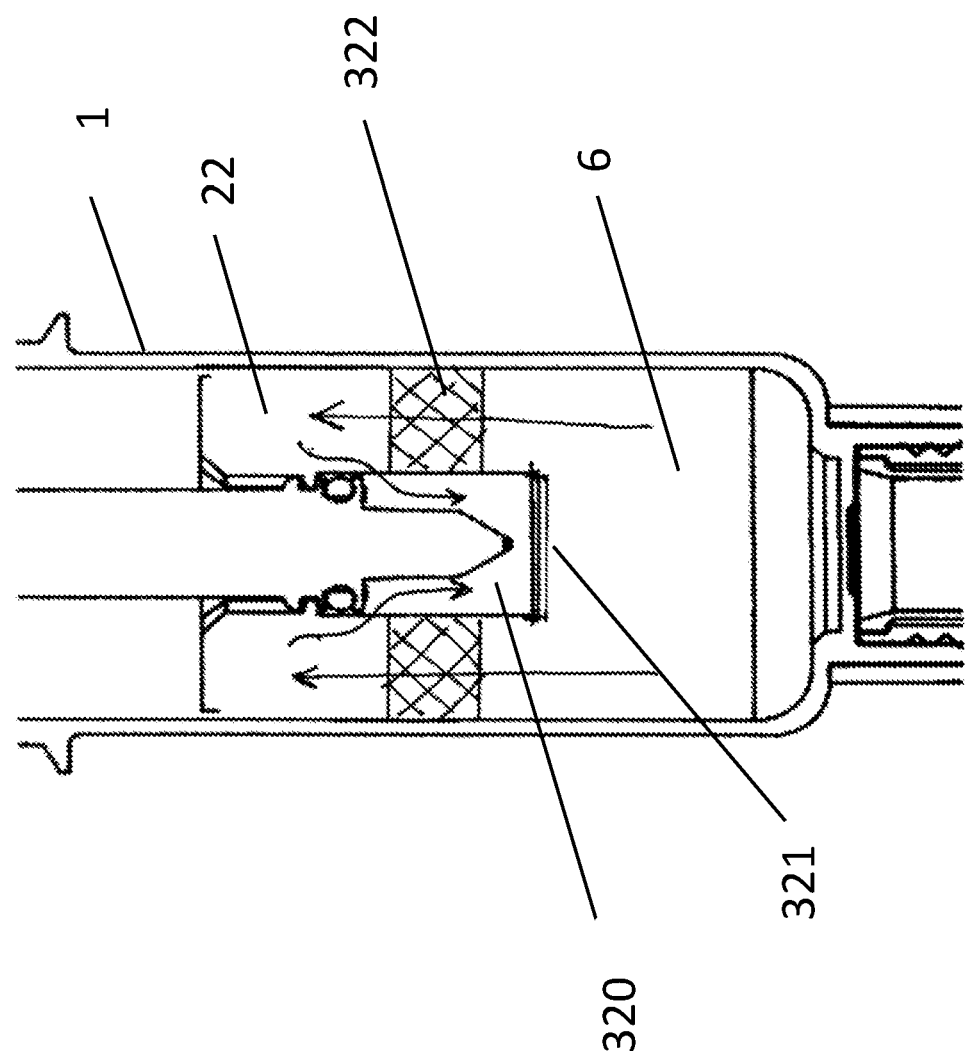
FIG. 38 is a cross-sectional side view illustrating an alternative embodiment of a dispense insert wherein the base of the insert bore is sealed, and the sample and sample reagent fluid can only flow through an outer bypass region of the insert as it is pressed into the cartridge, and then flows back into the top of the insert bore; the bypass region can include a filter or a porous material or fillers to remove or trap any particles within the sample fluid and prevent these from entering the test reservoirs(s)

FIG. 38 shows an alternative embodiment of the dispense insert 22 that allows a filter 322 to be included so that particles or inclusions in the sample fluid can be removed from the sample fluid that enters the dispense chamber and is subsequently dispensed into the coupled test reservoir or tube. In this embodiment, the dispense insert 22 has its underside entry to the cylindrical bore 320 closed by a membrane 321. As the dispense insert 22 is pressed into the cartridge assembly after the sample has been added, all of the displaced sample fluid must flow around the outside of the closed cylindrical bore 320 through the provided fluid paths. Within these fluid paths, one or more filter components 322 are included, as shown by crosshatching in FIG. 38. These filters 322 can be a fibre type material such as compressed glass fibre or a porous foam or porous plastic material. The one or more filter components 322 can be a single annular disk of material, or a number of smaller parts placed into each of the available fluid paths.

The filter components 322 physically capture and contain particles or material that would otherwise contaminate the sample fluid to be dispensed into the test reservoir. The filter components 322 can also incorporate biological or chemical components that bind to or capture components of the sample fluid that may otherwise inhibit or interfere with the test or amplification process. Fluid that has passed the filter components 322 will then fill the central cylindrical dispensing bore 320 from the top through the disperser slots as the part is submerged in the sample fluid. This filtered sample fluid is then available within the dispenser bore 320 for subsequent sealing and dispensing through perforations into the attached test tube.

Magnetic Bead Nucleic Acid Concentration

FIG. 39 shows an alternative configuration of the dispense insert 22 that allows a magnetic bead concentration function to be effected within the cartridge assembly. In this embodiment, the dispense insert 22 does not have any fluid path past the outside of the cylindrical bore 320, and all of the displaced sample fluid it is made to flow through the cylindrical bore 320 as the dispense insert 22 is inserted into the cartridge. In this embodiment, the sample preparation fluid contains magnetic particles, or these particles can be added as a test process step. The surface of the particles are coated or functionalised to bind with and capture at least one target species of interest in the sample material mixed into or in solution within the sample fluid. For example, a typical application is to bind nucleic acid, DNA or RNA material onto the functionalised surface coating of the magnetic particles as these particles mix within the sample fluid contained in the sample volume 6 of the cartridge 1. The magnetic particles can be very small, typically within the range of 0.5 micrometres to 10 micrometres. These magnetic particles mix freely and remain in suspension within the sample fluid, binding with and capturing target molecules onto their surface coatings.

The dispense insert or dispensing chamber is configured to have a sliding seal with the inside surface of the cartridge where a solid section of the insert 322 blocks fluid flowing past the outside of the central cylinder, such that all of the fluid in the sample chamber is forced to flow through the central cylindrical bore 320. Flow lines in FIG. 39 show the typical fluid path. In this embodiment, the dispense insert component incorporates one or more permanent magnets 331 captured within the moulded plastic of the component and located close to the inside surface of the cylindrical bore 320. A typical arrangement is to use a ring magnet 331 that surrounds the inside of the bore 320, where this magnet 331 is introduced into the moulding process at the time the insert 22 is injection moulded and is captured within the plastic structure of the part 22. As the sample fluid flows through the dispense cylinder, in proximity to the internal magnets 231, the magnetic particles are pulled against the side wall of the dispense cylinder by the magnetic field and retained within the cylindrical dispense tube 320 along with any captured DNA or RNA material.

Once the dispense component has been pressed into a seal at the base of the sample chamber, and the piston components engage with and seal the top of the chamber, the perforation component breaks through the thin material at the base of the sample chamber 1. During the dispense process, the magnetic beads magnetically held against the inside walls of the cylinder are wiped down the bore 320 by the O-ring sealed plunger, and are thus mixed back into the sample fluid trapped within the dispense cylinder and all of this fluid and magnetic beads are dispensed into the coupled test tube by the progressive travel of the piston into the amplification tube. This concentrates the DNA or RNA material within the sample fluid, and delivers it into the amplification tubes 107, 108. This has the advantage of concentrating and purifying the DNA or RNA nucleic acid material extracted from the sample resulting in a more sensitive and more reliable diagnostic test. The reagents within the test tube 3, 107, 108, once eluted by the added sample fluid, can react with the molecules selectively bound to the magnetic particles. The test tube reagents can contain salts, or chemicals or a pH suitable for release of the captured material from the surface of the magnetic particles within the test tubes 3, 107, 108 to assist with reaction and detection of these components.

End of the Test

Once a test has completed and the optional heat or ultraviolet post treatment completed, the instrument controller 201 can prompt the user on the front panel LCD display user interface, that the test is completed and that the cartridge can be removed from the instrument.

The removal of cartridge can be detected by the instrument controller 201 using feedback from the cartridge detection sensor 223 and the lid closed position sensor 222. Once the cartridge is detected as removed, the instrument controller 201 can complete self-test and setup the control sequence for the start of a new test, and prompt the user that the instrument is ready and to insert a cartridge to run a test.

The embodiments described herein are provided by way of non-limiting example only, and many modifications of the described embodiments will be apparent to those of ordinary skill in the art without departing from the scope of the invention.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The invention claimed is:

1. A diagnostic test system, including:
a diagnostic test assembly; and
a diagnostic test apparatus to receive and interact with the diagnostic test assembly to perform a diagnostic test on a biological or environmental sample therein;
wherein the diagnostic test assembly includes:
a sample preparation reservoir to receive the biological or environmental sample into a sample preparation fluid contained in the sample preparation reservoir for preparation of a sample fluid therefrom, the sample preparation reservoir initially providing an open volume free of obstructions such that a swab carrying the biological or environmental sample can be used to stir the sample preparation fluid in the sample preparation reservoir and to wash the biological or environmental sample from the swab into the sample preparation fluid;
a sample dispensing mechanism for insertion into the sample preparation reservoir after receipt of the biological or environmental sample therein;
a closure to seal the sample preparation reservoir after receipt of the biological or environmental sample and the sample dispensing mechanism therein;
at least one diagnostic test reservoir coupled to the sample preparation reservoir; and
at least one seal between the sample preparation reservoir and the at least one diagnostic test reservoir to prevent fluid movement between the sample preparation reservoir and the at least one diagnostic test reservoir;
wherein the sample dispensing mechanism is operable such that a single sustained screwing action applied to the closure relative to the sample preparation reservoir causes the sample dispensing mechanism to disrupt the at least one seal to dispense sample fluid from the sample preparation reservoir into the at least one diagnostic test reservoir and to dispense a predetermined sub-volume of the sample fluid from the sample preparation reservoir into the at least one diagnostic test reservoir for diagnostic testing and detection therein while preventing further fluid movement between the sample preparation reservoir and the at least one diagnostic test reservoir.

2. The diagnostic test system of claim 1, wherein the sample dispensing mechanism is attached to the closure so that an act of applying the closure to the sample preparation reservoir also effects the insertion of the sample dispensing mechanism into the sample preparation reservoir.

3. The diagnostic test system of claim 1, wherein the diagnostic test apparatus is configured to determine completion of the operation of the sample dispensing mechanism and, responsive to the determination, to proceed with diagnostic testing of the contents of the at least one diagnostic test reservoir.

4. The diagnostic test system of claim 1, wherein the closure includes a screw thread, and the diagnostic test apparatus includes at least one sensing component configured to determine a degree of rotation and/or thread progression of the closure, and the diagnostic test apparatus is configured to prompt a user to complete the closure operation if the at least one sensing component has determined that the closure operation is incomplete; and to automatically progress to a next stage of diagnostic testing if the closure operation has been determined as being complete.

5. The diagnostic test system of claim 1, further including a second closure that seals the sample preparation fluid within the sample preparation reservoir prior to use, and that is removed to allow the biological or environmental sample to be added to the sample preparation fluid contained in the sample preparation reservoir.

6. The diagnostic test system of claim 1, wherein the sample dispensing mechanism includes:
a dispensing chamber that forms a second seal against the at least one seal to trap the predetermined sub-volume of the sample fluid within the dispensing chamber;
a piercing member that disrupts the at least one seal by forming at least one opening therein; and
a plunger mechanism that forms a sliding seal with an internal surface of the dispensing chamber, wherein the sliding seal is configured to slide along the internal surface of the dispensing chamber to dispense the predetermined sub-volume of the sample fluid therefrom, through the at least one opening, and into the at least one diagnostic test reservoir.

7. The diagnostic test system of claim 6, wherein the dispensing chamber includes an outer surface having mutually spaced chamber locating features extending therefrom and configured to align the dispensing chamber centrally of the sample preparation reservoir and allow sample fluid to flow between the chamber locating features as the sample dispensing mechanism is inserted into the sample preparation reservoir.

8. The diagnostic test system of claim 6, wherein the sample dispensing mechanism is configured so that a single action performed by a user causes two stages of operation of the sample dispensing mechanism, including a first stage of operation that traps the predetermined sub-volume of the sample fluid within the dispensing chamber, and a second stage of operation wherein the sample fluid is dispensed from the dispensing chamber.

9. The diagnostic test system of claim 8, wherein the sample dispensing mechanism includes a force sequencing component that is reconfigured or broken to allow the second stage of operation.

10. The diagnostic test system of claim 9, wherein the force sequencing component includes a breakable component that is configured to break to allow operation of the sample dispensing mechanism to proceed from the first stage of operation to the second stage of operation.

11. The diagnostic test system of claim 9, wherein the force sequencing component includes a collapsible or crushable spacer that presses against and causes the dispensing chamber to seal in the first stage of operation, and in the second stage of operation is collapsed or crushed to maintain the seal, perform the perforation action, and operate the plunger to dispense the sample fluid from the dispensing chamber.

12. The diagnostic test system of claim 6, wherein the dispensing chamber is initially configured so that, as the sample dispensing mechanism is inserted into the sample preparation reservoir, the sample fluid is forced to flow around the outside of the dispensing chamber before it can flow into the dispensing chamber, wherein the fluid that flows around the outside of the dispensing chamber is caused to flow through a filter or porous filler material that retains and/or traps particles and debris and/or incorporates biological or chemical components that bind to or capture components of the sample fluid that may otherwise inhibit or interfere with the diagnostic test or amplification process.

13. The diagnostic test system of claim 6, wherein the sample preparation reservoir includes magnetic particles with the sample preparation fluid, the surface of the magnetic particles being coated or functionalised to bind with and capture at least one predetermined target species of the biological or environmental sample when the magnetic particles are mixed within the sample fluid, and the sample dispensing mechanism is configured so that, as the sample dispensing mechanism is inserted into the sample preparation reservoir, the sample fluid is forced to flow through the dispensing chamber, and one or more magnets are located in close proximity to the inside surface of the dispensing chamber so that magnetic particles contained within the sample fluid and have captured target species are attracted to and held against the internal surface of the dispensing chamber, such that the plunger mechanism that forms a sliding seal with the internal surface of the dispensing chamber collects the magnetic particles held against the internal surface and dispenses them into the at least one diagnostic test reservoir to provide an increased concentration of the at least one predetermined target species in the predetermined sub-volume of the sample fluid dispensed into the at least one diagnostic test reservoir.

14. The diagnostic test system of claim 1, wherein at least one of the closure and the sample preparation reservoir is configured to prevent or at least inhibit removal of the closure from the sample preparation reservoir so that the fluids remain sealed within the diagnostic test assembly.

15. The diagnostic test system of claim 1, wherein the at least one diagnostic test reservoir includes at least two diagnostic test reservoirs.

16. The diagnostic test system of claim 15, wherein the diagnostic test reservoirs contain different diagnostic test and/or detection reagents selected to perform respective different diagnostic tests and/or to detect respective different target entities.

17. The diagnostic test system of claim 1, wherein the sample preparation reservoir contains reagents for sample preparation including cell lysis, and at least one of the diagnostic test reservoirs is configured for nucleic acid amplification and binding of specific markers to enable an optical output that can be measured by the diagnostic test apparatus to determine a corresponding diagnostic test result.

18. The diagnostic test system of claim 1, wherein the at least one diagnostic test reservoir includes at least one diagnostic test reservoir that is transparent to enable a corresponding test result to be observed visually as a change in emission and/or absorption at one or more specific wavelengths and/or turbidity within the corresponding at least one diagnostic test reservoir.

19. The diagnostic test system of claim 1, wherein at least one of the at least one diagnostic test reservoirs is transparent, and the diagnostic test apparatus is configured to determine a test result in the at least one diagnostic test reservoir by detecting or measuring a change in emission and/or absorption at one or more wavelengths within the at least one diagnostic test reservoir, wherein the diagnostic test apparatus is optionally configured to illuminate the at least one diagnostic test reservoir to enhance or produce the detecting or measuring.

20. The diagnostic test system of claim 1, wherein the diagnostic test apparatus and the diagnostic test assembly include respective alignment and support features configured for mutual engagement to ensure that the diagnostic test assembly is received in a predetermined alignment with respect to the diagnostic test apparatus and to maintain the alignment when the closure is applied to the sample preparation reservoir after receipt of the biological or environmental sample and the sample dispensing mechanism therein.

21. The diagnostic test system of claim 1, wherein the diagnostic test apparatus includes one or more components configured to apply a changing and/or moving magnetic field to the diagnostic test assembly to cause corresponding movements of magnetic particles within at least one of the sample preparation reservoir and the at least one diagnostic test reservoir, and thereby cause mixing of the sample and sample preparation fluid therein.

22. The diagnostic test system of claim 1, wherein the diagnostic test apparatus and the diagnostic test assembly are configured to allow the diagnostic test apparatus to independently control the temperatures of the sample preparation reservoir and the at least one diagnostic test reservoir.

23. The diagnostic test system of claim 1, wherein the diagnostic test apparatus includes one or more image sensors configured to generate image data representing one or more images of at least a portion of the diagnostic test assembly, wherein the images represent at least one of:
   (i) fluid distribution within at least one of the at least one diagnostic test reservoir and the sample preparation reservoir, and the diagnostic test apparatus is configured to process the image data to monitor dispensing of the sample fluid, and to proceed to a next stage of diagnostic testing if the monitoring has determined that the dispensing is complete; and
   (ii) a fluid volume contained within the at least one diagnostic test reservoir, and the diagnostic test apparatus is configured to process the image data to allow compensation for the volume tolerances in the dispensed fluid to allow for improved test result determination.

24. The diagnostic test system of claim 1, wherein the diagnostic test apparatus includes one or more optical sensors mounted to a translation stage under control of a controller of the diagnostic test apparatus so that the optical sensors can measure optical absorption or emission or fluorescence from one or more selected diagnostic test reservoirs of the diagnostic test assembly.

25. The diagnostic test system of claim 1, wherein the diagnostic test apparatus includes at least one ultra violet (UV) emission source to denature samples contained within the diagnostic test assembly following a diagnostic test to inhibit contamination in the event of sample fluid escaping from the diagnostic test assembly.

26. A diagnostic test method, including the steps of:
   placing a diagnostic test assembly into a receiving port of a diagnostic test apparatus configured to perform a diagnostic test on a biological or environmental sample therein;
   adding the biological or environmental sample into a sample preparation fluid contained in a sample preparation reservoir of the diagnostic test assembly for preparation of a sample fluid therein;

after the adding step, inserting a sample dispensing mechanism into the sample preparation reservoir and applying a closure thereto;

operating the sample dispensing mechanism to disrupt at least one seal between the sample preparation reservoir and at least one diagnostic test reservoir of the diagnostic test apparatus to allow sample fluid to enter the at least one diagnostic test reservoir from the sample preparation reservoir, and to dispense a predetermined sub-volume of the sample fluid from the sample preparation reservoir into the at least one diagnostic test reservoir for diagnostic testing and detection therein while preventing further fluid movement between the sample preparation reservoir and the at least one diagnostic test reservoir.

27. The diagnostic test method of claim 26, wherein the sample dispensing mechanism is attached to the closure so that the applying of the closure to the sample preparation reservoir also effects the insertion of the sample dispensing mechanism into the sample preparation reservoir.

28. The diagnostic test method of claim 27, wherein a single action by a user causes the operation of the sample dispensing mechanism, the single action being a sustained screwing action applied to the closure relative to the sample preparation reservoir, wherein the screwing action causes operation of the sample dispensing mechanism and seals the sample preparation reservoir.

* * * * *